United States Patent [19]

Sadaki et al.

[11] Patent Number: 4,673,738

[45] Date of Patent: Jun. 16, 1987

[54] NOVEL INTERMEDIATES OF CEPHALOSPORINS AND PROCESS FOR PRODUCING 7-(SUBSTITUTED OR UNSUBSTITUTED AMINO)-3-SUBSTITUTED METHYL-$\Delta^3$-CEPHEM-4-CARBOXYLIC ACIDS

[75] Inventors: Hiroshi Sadaki; Hirokazu Narita; Hiroyuki Imaizumi, all of Toyama; Yoshinori Konishi, Takaoka; Takihiro Inaba, Namerikawa; Tatsuo Hirakawa, Toyama; Hideo Taki, Sagamihara; Masaru Tai, Toyama; Yasuo Watanabe, Toyama; Isamu Saikawa, Toyama, all of Japan

[73] Assignee: Handi-Pac Inc., Hermann, Mo.

[21] Appl. No.: 654,681

[22] Filed: Sep. 26, 1984

Related U.S. Application Data

[62] Division of Ser. No. 304,912, Sep. 23, 1981, Pat. No. 4,489,072.

[30] Foreign Application Priority Data

Sep. 25, 1980 [JP] Japan ................................ 55-132253
Nov. 12, 1980 [JP] Japan ................................ 55-158184
Dec. 13, 1980 [JP] Japan ................................ 55-175263

[51] Int. Cl.[4] ................ C07D 501/38; C07D 501/40; C07D 501/46
[52] U.S. Cl. .................................... 540/222; 540/226; 540/227; 540/221
[58] Field of Search ....................... 544/22; 514/202; 540/221

[56] References Cited

U.S. PATENT DOCUMENTS 3,821,206  6/1974  Cowley ........................ 544/28
3,859,282  1/1975  Cheng ......................... 544/16
4,143,166  3/1979  Takaya ........................ 544/26
4,148,997  4/1979  Haviv ......................... 544/26
4,317,907  3/1982  Saikawa ....................... 544/21
4,343,937  8/1982  Christensen ................... 544/16

FOREIGN PATENT DOCUMENTS 2537974  3/1976  Fed. Rep. of Germany .

OTHER PUBLICATIONS

Elderfield—I and II "Heterocyclic Compounds" vol. 7 and 8, pp. 456 and 457, 8 and 9, Wiley & Sons (1957).
Tetrahedron Letters, No. 30, 2625–2628, 1974.
J. Am. Chem. Soc., 62, 2385 (1940).
J. Am. Chem. Soc., 78, 2318 (1956).

Primary Examiner—Sidney Marantz
Assistant Examiner—Robert Benson
Attorney, Agent, or Firm—Oblon, Fisher, Spivak, McClelland & Maier

[57]  ABSTRACT

This invention relates to novel 7-(substituted or unsubstituted amino)-3-substituted methyl-$\Delta^3$-cephem-4-carboxylic acids in which a substituted or unsubstituted 1,2,4-triazolyl or 2-(1,2,3,4-tetrazolyl) group attaches to the exomethylene group at the 3-position of the cephem ring through a carbon-nitrogen bond. These cephalosporins are useful intermediates for producing various novel cephalosporins. Also, this invention concerns a process for producing a compound represented by the formula:

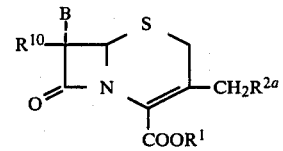

which comprises reacting a compound represented by the formula:

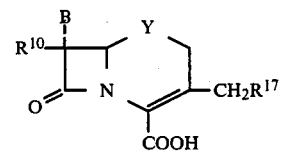

with an optionally substituted triazole or tetrazole in the presence of an acid or a complex of the acid in an organic solvent at 0° to 80° C.

5 Claims, No Drawings

NOVEL INTERMEDIATES OF CEPHALOSPORINS AND PROCESS FOR PRODUCING 7-(SUBSTITUTED OR UNSUBSTITUTED AMINO)-3-SUBSTITUTED METHYL-Δ³-CEPHEM-4-CARBOXYLIC ACIDS

This is a division, of application Ser. No. 304,912, filed Sept. 23, 1981, now U.S. Pat. No. 4,489,072.

This invention relates to novel cephalosporins, processes for producing said cephalosporins, intermediates for the production of said cephalosporins, and a process for producing the intermediates.

The present inventors have conducted studies with the aim of discovering compounds having a broad antibacterial spectrum, exhibiting an excellent antibacterial activity to gram-positive and gram-negative bacteria, being stable to β-lactamase produced by bacteria, having a low toxicity, being at the same time well absorbable upon oral or parenteral administration and having an excellent therepeutic effect on the human and animal diseases. As a result, it has been found that novel cephalosporins characterized in that a substituted or unsubstituted aryl, acylamino, aromatic teterocyclic, triazolyl or tetrazolyl group is attached to the exomethylene group at the 3-position of the cephem ring, said aromatic heterocyclic group being attached through a carbon-carbon bond and said triazolyl or tetrazolyl group being attached through a carbon-nitrogen bond, and the following group is attached to the amino group at the 7-position, have the above-mentioned excellent properties:

wherein A, $R^3$ and $R^4$ are as defined below.

It is objects of this invention to provide novel cephalosporins having the above-mentioned chemical structural characteristics features, to provide novel cephalosporins having a broad antibacterial spectrum, to provide novel cephalosporins stable against β-lactamase produced by bacteria, to provide novel cephalosporins having a low toxicity and being well absorbed upon oral or parenteral administration and to provide novel cephalosporins having an excellent therapeutic effect on the human and animal diseases.

It is further objects of this invention to provide a process for producing said novel cephalosporins, to provide intermediates for the production of said novel cephalosporins and to provide a process for producing said intermediates.

Other objects and advantages of this invention will become apparent from the following description.

The novel cephalosporins of this invention involve compounds represented by the formula [I] and salts thereof:

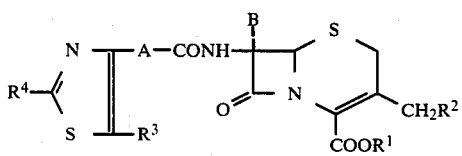

wherein $R^1$ represents a hydrogen atom or a carboxyl-protecting group; $R^2$ represents a substituted or unsubstituted aryl, acylamino, aromatic heterocyclic, triazolyl or tetrazolyl group, said aromatic heterocyclic group being attached to the 3-exomethylene group through a carbon-carbon bond and said triazolyl or tetrazolyl group being attached to the 3-exomethylene group through a carbon-nitrogen bond; $R^3$ represents a hydrogen or halogen atom; $R^4$ represents a hydrogen atom or an amino group which may be protected or substituted; A represents a group of the formula, —CH₂—, or a group of the formula,

in which $R^5$ represents a hydrogen atom or an alkyl group and the bolt ∼∼ represents syn or anti isomer or their mixture; and B represents a hydrogen atom or a lower alkoxy group.

In this specification, unless otherwise specified, the term "alkyl" means straight or branched chain $C_{1-14}$alkyl, for example, methyl, ethyl, n-propyl, iso-propyl, n-butyl, iso-butyl, sec.-butyl, tert.-butyl, pentyl, hexyl, heptyl, octyl, dodecyl and the like; the term "alkoxy" means O-alkyl having the alkyl group defined above; the term "lower alkyl" means straight or branched chain $C_{1-5}$alkyl, for example, methyl, ethyl, n-propyl, iso-propyl, n-butyl, iso-butyl, sec.-butyl, tert.-butyl, pentyl and the like; the term "lower alkoxy" means —O—lower alkyl having the lower alkyl group defined above; the term "acyl" means $C_{1-12}$acyl, for example, acetyl, propionyl, butyryl, benzoyl, naphthoyl, pentanecarbonyl, cyclohexanecarbonyl, furoyl, thenoyl and the like; the term "acyloxy" means —O—acyl having the acyl group defined above; the term "alkylthio" means —S—alkyl having the alkyl group defined above; the term "akenyl" means $C_{2-10}$alkenyl, for example, vinyl, allyl, isopropenyl, 2-pentenyl, butenyl and the like; the term "alkinyl" means $C_{2-10}$alkinyl, for example, ethynyl, 2-propynyl and the like; the term "cycloalkyl" means $C_{3-7}$cycloalkyl, for example, cyclopropyl, cyclobutyl, cyclopentyl, cyclohexyl, cycloheptyl and the like; the term "alkadienyl" means $C_{4-10}$alkadienyl, for example, 1,3-butadienyl, 1,4-hexadienyl, and the like; the term "cycloalkenyl" means $C_{5-7}$cycloalkenyl, for example, cyclopentenyl, cyclohexenyl and the like; the term "cycloalkadienyl" means $C_{5-7}$cycloalkadienyl, for example, cyclopentadienyl, cyclohexadienyl and the like; the term "aryl" means, for example, phenyl, naphthyl, indanyl and the like; the term "aralkyl" means arlower alkyl, for example, benzyl, phenethyl, 4-methylbenzyl, naphthylmethyl and the like; the term "heterocyclic group" means heterocyclic group having at least one hetero-atom selected from the group consisting of oxygen, nitrogen and sulfur, for example, furyl, thienyl, pyrrolyl, pyrazolyl, imidazolyl, thiazolyl, isothiazolyl, oxazolyl, isoxazolyl, thiadiazolyl, oxadiazolyl, thiatriazolyl, oxatriazolyl, triazolyl, tetrazolyl, pyridyl, 3-(2-methyl-4-pyrrolinyl), 3-(4-pyrrolinyl), N-(methylpiperidinyl), quinolyl, phenazinyl, 1,3-benzodioxolanyl, benzofuryl, benzothienyl, benzoxazolyl, benzothiazolyl, coumarinyl and the like; the term "heterocycle-alkyl" means a group consisting of a heterocyclic group as defined above and an alkyl group as defined above; and the term "halogen atom" means fluorine, chlorine, bromine and iodine atoms.

In the formulas described herein, $R_1$ is a hydrogen atom or a carboxyl-protecting group. The carboxyl-protecting groups which have conventionally been used in the penicillin and cephalosporin fields are available and include ester-forming groups which can be removed by catalytic reduction, chemical reduction or other treatments under mild conditions; ester-forming groups which can easily be removed in living bodies; and other known ester-forming groups which can easily be removed by treatment with water or an alcohol, such as organic silyl groups, organic phosphorus-containing groups, organic tin-containing groups, or the like.

Examples of typical carboxyl-protecting groups are:

(a) Alkyl groups;

(b) Substituted lower alkyl groups, at least one of the substituents of which is halogen, nitro, carboalkoxy, acyl, alkoxy, oxo, cyano, cycloalkyl, aryl, alkylthio, alkylsulfinyl, alkylsulfonyl, alkoxycarbonyl, 5-alkyl-2-oxo-1,3-dioxol-4-yl, 1-indanyl, 2-indanyl, furyl, pyridyl, 4-imidazolyl, phthalimido, succinimido, acetidino, aziridino, pyrrolidino, piperidino, morpholino, thiomorpholino, pyrrolyl, pyrazolyl, thiazolyl, isothiazolyl, oxazolyl, isoxazolyl, thiadiazolyl, oxadiazolyl, thiatriazolyl, oxatriazolyl, triazolyl, tetrazolyl, pyridyl, quinolyl, phenazinyl, benzofuryl, benzothienyl, benzoxazolyl, benzothiazolyl, coumarinyl, N-lower alkyl-piperazino, 2,5-dimethylpyrrolidino, 1,4,5,6-tetrahydropyrimidinyl, 4-methylpiperidino, 2,6-dimethyl-piperidino, 3-(2-methyl-4-pyrrolinyl), 3-(4-pyrrolinyl), N-(methylpiperidinyl), 1,3-benzodioxolanyl, alkylamino, dialkylamino, acyloxy, acylamino, acylthio, dialkylaminocarbonyl, alkoxycarbonylamino, alkenyloxy, aryloxy, aralkyloxy, alicycleoxy, heterocycle-oxy, alkoxycarbonyloxy, alkenyloxycarbonyloxy, aryloxycarbonyloxy, aralkyloxycarbonyloxy; alicycle-oxycarbonyloxy, heterocycle-oxycarbonyloxy, alkenyloxycarbonyl, aryloxycarbonyl, aralkyloxycarbonyl, alicycle-oxycarbonyl, heterocycle-oxycarbonyl, alkylanilino and alkylanilino substituted by halogen, lower alkyl, or lower alkoxy;

(c) Cycloalkyl groups, lower-akyl-substituted cycloalkyl groups, or [2,2-di(lower alkyl)-1,3-dioxolan-4-yl]methyl groups;

(d) Alkenyl groups;

(e) Alkinyl groups;

(f) Phenyl group, substituted phenyl groups, at least one of the substituents of which is selected from the substitutents exemplified in above (b); or aryl groups represented by the formula:

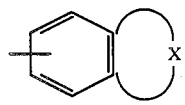

wherein X is —CH=CH—O—, —CH=CH—S—, —CH$_2$CH$_2$S—, —CH=N—CH=N—, —CH=CH—CH=CH—, —CO—CH=CH—CO—, or —CO—CO—CH=CH—, or substituted derivatives thereof, the substituents of which are selected from those exemplified in above (b), or the formula:

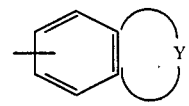

wherein Y is a lower alkylene group such as —(CH$_2$)$_3$— and —(CH$_2$)$_4$—, or substituted derivatives thereof, the substituents of which are selected from those exemplified in above (b);

(g) Aralkyl groups which may be substituted, at least one of the substituents of which is selected from those exemplified in above (b);

(h) Heterocyclic groups which may be substituted, at least one of the substituents of which is selected from those exemplified in above (b);

(i) Alicylic indanyl or phthalidyl groups or substituted derivatives thereof, the substituent of which is halogen or methyl; alicyclic tetrahydronaphthyl groups, or substituted derivatives thereof, the substituent of which is halogen or methyl; trityl group, cholesteryl group, or bicyclo[4,4,0]-decyl group.

(j) Alicyclic phthalidylidene-lower alkyl group or substituted derivatives thereof, the substituent of which is halogen or lower alkoxy group.

The carboxyl-protecting groups listed above are typical examples, and there may be used any groups selected from those disclosed in U.S. Pat. Nos. 3,499,909; 3,573,296; and 3,641,018, West German Offenlegungsschrift No. 2,301,014; 2,253,287; and 2,337,105.

Among them, preferable carboxyl-protecting groups are those which can readily be removed in living bodies such as 5-lower alkyl-2-oxo-1,3-dioxol-4-yl groups, acyloxyalkyl groups, acylthioalkyl groups, phthalidyl group, indanyl group, phenyl group, substituted or unsubstituted phthalidylidene-lower alkyl groups or groups represented by the formulas:

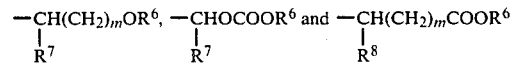

wherein $R^6$ represents a straight or branched chain substituted or unsubstituted alkyl, alkenyl, aryl, aralkyl, alicyclic, or heterocyclic group, $R^7$ represents a hydrogen atom or an alkyl group, $R^8$ represents a hydrogen atom, a halogen atom or a substituted or unsunstituted alkyl, cycloalkyl, aryl or heterocyclic group or —(CH$_2$)$_n$—COOR$^6$ wherein $R^6$ is as defined above and n represetns 0, 1 or 2, and m represents 0, 1 or 2.

The above-mentioned preferable carboxyl-protecting groups include specifically 5-lower alkyl2-oxo-1,3-dioxol-.4-yl groups such as 5-methyl-2-oxo1,3-dioxol-4-yl, 5-ethyl-2-oxo-1,3-dioxol-4-yl, 5-propyl-2-oxo-1,3,-dioxol-4-yl, and the like; acyloxyalkyl groups, such as acetoxymethyl, pivaloyloxymethyl, propionyloxymethyl, butyryloxymethyl, iso-butyryloxymethyl, valeryloxymethyl, 1-acetoxy-ethyl, 1-acetoxy-n-propyl, 1-pivaloyloxy-ethyl, 1-pivaloyloxy-n-propyl and the like; acylthioalkyl groups such as acetylthiomethyl, pivaloylthiomethyl, benzoylthiomethyl, p-chlorobenzoylthiomethyl, 1-acetylthio-ethyl, 1-pivaloylthio-ethyl, 1-benzoylthio-ethyl, 1-(p-chlorobenzoylthio)-ethyl and the like; alkoxymethyl groups such as methoxymethyl, ethoxymethyl, propoxymethyl, isopropoxymethyl, butyloxymethyl and the like; alkoxycarbonyloxymethyl groups such as methoxycarbonyloxymethyl, ethoxycarbonyloxymethyl, propoxycarbonylmethyl, isopropoxycarbonylmethyl, n-butyloxycarbonylmethyl, tert-butyloxycarbonylmethyl, 1-methoxycarbonyloxyethyl, 1-ethoxycarbonyloxy-ethyl, 1-propoxycarbonyloxy-ethyl, 1-isopropoxycarbonyloxyethyl, 1-butyloxycarbonyloxy-ethyl and the like; alkoxycarbonylalkyl groups such as methoxycarbonylmethyl, ethoxycarbonylmethyl and the like; phthalidyl group; indanyl group; phenyl group; and phthalididenealkyl groups such as 2-(phthalidylidene)-ethyl, 2-(5-fluorophthalidylidene)-ethyl, 2-(6-chlorophthalidylidene)ethyl, 2-(6-methoxyphthalidylidene)-ethyl and the like.

$R^2$ represents a substituted or unsubstituted aryl, acylamino, aromatic heterocyclic, triazolyl or tetrazolyl group, said aromatic heterocyclic group being attached to the 3-exomethylene group through a carbon-carbon bond, and said triazolyl or tetrazolyl group being attached to the 3-exomethylene group through a carbon-nitrogen bond. Herein, said acylamino group is represented by the formula, $R^9$CONH-, wherein $R^9$ is, for example, an alkyl, alkenyl, alkadienyl, cycloalkyl, cycloalkenyl, cycloalkadienyl, aryl, aralkyl, heterocyclic or heterocycle-alkyl group. Said aromatic heterocyclic group includes, for example, furyl, thienyl, pyridyl, benzofuryl, benzothienyl, quinolyl, isoquinolyl and the like. Said triazolyl or tetrazolyl group includes 1,2,3-triazolyl, 1,2,4-triazolyl and 1,2,3,4-tetrazolyl. Though these triazolyl and tetrazolyl groups have isomers, any nitrogen atom in their ring may be attached to the 3-exomethylene. All the cases are included in this invention. Specific examples thereof are 1-(1,2,3-triazolyl), 2-(1,2,3-triazolyl), 1-(1,2,4-triazolyl), 2-(1,2,4-triazolyl), 4-(1,2,4-triazolyl), 1-(1,2,3,4-tetrazolyl) and 2-(1,2,3,4-tetrazolyl).

Further, the aryl, acylamino, aromatic heterocyclic, triazolyl and tetrazolyl groups for $R^2$ may be substituted by at least one substituent such as halogen, alkyl, aralkyl, aryl, alkenyl, hydroxyl, oxo, alkoxy, alkylthio, nitro, cyano, amino, alkylamino, dialkylamino, acylamino, acyl, acyloxy, acylalkyl, alkoxycarbonyl, carbamoyl, aminoalkyl, N-alkylaminoalkyl, N,N-dialkylaminoalkyl, hydroxyalkyl, hydroxyiminoalkyl, alkoxyalkyl, carboxyalkyl, alkoxycarbonylalkyl, aralkoxycarbonylalkyl, sulfoalkyl, sulfo, sulfamoylalkyl, sulfamoyl, carbamoylalkyl, carbamoyalkenyl, N-hydroxycarbamoylalkyl, and the like. Among these substituents, hydroxyl, amino and carboxyl may be protected by an appropriate protecting group conventionally used in this field. As the protecting group for the hydroxyl group, there may be used all groups which can conventionally be used for the protection of hydroxyl group, specficially including readily removable acyl groups such as benzyloxycarbony, 4-nitrobenzyloxycarbonyl, 4-bromobenzyloxycarbonyl, 4-methoxybenzylocycarbonyl, 3,4-dimethoxybenzyloxycarbonyl, 4-(phenylazo)benzyloxycarbonyl, 4-(4-methoxyphenylazo)benzyloxycarbonyl, tert.-butoxycarbonyl, 1,1-dimethylpropoxycarbonyl, isopropoxycarbonyl, diphenylmethoxycarbonyl, 2,2,2-trichloroethoxycarbonyl, 2,2,2-tribromoethoxycarbonyl, 2-furfuryloxycarbonyl, 1-adamantyloxycarbonyl, 1-cyclopropylethoxycarbonyl, 3-quinolyloxycarbonyl, acetyl, trifluoroacetyl and the like, as well as benzyl, trityl, methoxymethyl, 2-nitrophenylthio, 2,4-dinitrophenylthio and the like. As the protecting group for the amino group, there may be used all groups which can conventionally be used for the protection of amino group, specifically including readily removable acyl groups such as trichloroethoxycarbonyl, tribromoethoxycarbonyl, benzyloxycarbonyl, p-toluenesulfonyl, p-nitrobenzyloxycarbonyl, o-bromobenzyloxycarbonyl, o-nitrophenylsulfenyl, (mono-, di- or tri-)chloroacetyl, trifluoroacetyl, formyl, tert.-amyloxycarbonyl, tert.-butoxycarbonyl, p-methoxybenzyloxycarbonyl, 3,4-dimethoxybenzyloxycarbonyl, 4-(phenylazo)benzyloxycarbonyl, 4-(4-methoxyphenylazo)benzyloxycarbonyl, pyridine-1-oxide-2-yl-methoxycarbonyl, 2-furyloxycarbonyl, diphenylmethoxycarbonyl, 1,1-dimethylpropoxycarbonyl, isopropoxycarbonyl, 1-cyclopropylethoxycarbonyl, phthaloyl, succinyl, 1-adamantyloxycarbonyl, 8-quinolyloxycarbonyl and the like, as well as such readily removable groups as trityl, 2-nitrophenylthio, 2,4-dinitrophenylthio, 2-hydroxybenzylidene, 2-hydroxy 5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl2-propylidene, 1-benzoyl-2-propylidene, 1-[N-(2-methoxyphenyl)carbamoyl]-2-propylidene, 1-[N-(4-methoxyphenyl)carbamoyl]-2-propylidene, 2-ethoxycarbonylcylcohexylidene, 2-ethoxycarbonylcyclopentylidene, 2-acetylcyclohexylidene, 3,3-dimethyl-5-oxocyclohexylidene and the like, and other protecting groups for amino group such as di- or tri-alkylsilyl and the like. As the protecting group for carboxyl group, there may be used all groups which can conventionally be used for the protection of carboxyl group, specifically including such groups as methyl, ethyl, n-propyl, iso-propyl, tert,-butyl, n-butyl, benzyl, diphenylmethyl, trityl, p-nitrobenzyl, p-methoxybenzyl, benzoylmethyl, acetylmethyl, p-nitrobenzoylmethyl, p-bromobenzoylmethyl, p-methanesulfonylbenzoylmethyl, phthalimidomethyl, trichloroethyl, 1,1-dimethyl-2-propenyl, 1,1-dimethylpropyl, acetoxymethyl, propionyloxymethyl, pivaloyloxymethyl, 3-metyl-3-butinyl, succinimidomethyl, 1-cyclopropylethyl, methylsulfenylmethyl, phenylthiomethyl, dimethylaminomethyl, quinoline1-oxide-2-yl-methyl, pyridine-1-oxide-2-yl-methyl, bis(p-methoxyphenyl)methyl and the like; non-metallic compounds such as titanium tetrachloride; and silyl compounds such as dimethylchlorosilane as mentioned in Japanese Patent Application Kokai (Laid-Open) No. 7,073/71, and Dutch Patent Application No. 71 05259 (Laid-open).

In the formula [I], $R^4$ represents a hydrogen atom or an amino group which may be protected or substituted. As the protecting group for the amino group, there may be used groups which can conventionally be used in the fields of penicillin and cephalosporin, specifically including the protecting groups for amino group mentioned as to $R^2$. As the substituent for said substituted amino group, there may be used, for example, alkyl, alkenyl, cycloalkyl, aryl, aralkyl, heterocyclic, and heterocycle-alkyl groups. The amino group may be substituted by one or more of these substitutents. These protecting groups and substituents may additionally be substituted by one or more substituents such as halogen, alkyl, nitro, hydroxyl, alkoxy, oxo, thioxo, alkylthio, acylamino, acyl, acyloxy, aryloxy, carboxyl, carbamoyl, hydroxyalkyl, alkoxyalkyl, carboxyalkyl, alkoxycarbonyl, amino, alkylamino, aminoalkyl, N-alkylaminoalkyl, sulfoalkyl, sulfo, sulfamoyl, carbamoylalkyl, aryl, and heterocyclic groups, examples of the heterocyclic group being furyl, thienyl and the like. The hdyroxyl, amino and carboxyl groups used as the substituent may additionally be protected with an appropriate protecting group which is conventionally employed, including, for example, the protecting groups for hydroxyl, amino and carboxyl groups mentioned as to $R^2$.

A represents —$CH_2$— or

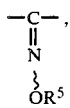

wherein $R^5$ represents a hydrogen atom or an alkyl group The oxime compound wherein A represents

covers it syn and anti isomers, as well as their mixtures.

In the group,

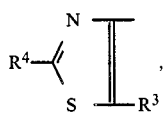

of the formula [I], there exist tautomers when $R^4$ is an amino group which may be a protected or substitued amino group, as shown by the following equilibrium equation, and the tautomers are also included in this invention:

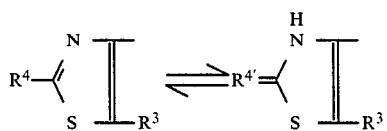

wherein $R^3$ and $R^4$ are as defined above, and $R^{4'}$ represents an imino group which may be protected or substituted. As the protecting group for imino group represented by $R^{4'}$ in the above-mentioned equilibrium equation, there may be amployed the groups conventionally used in the fields of penicillin and cephalosporin, specifically including the same groups as the monovalent groups among the protecting groups for amino group mentioned as to $R^2$.

As the substituent for said substituted imino group, there may be used the substituents for amino group mentioned as to $R^4$.

As the salts of the compound represented by the formula [I], there may be mentioned salts at the basic group or the acidic group usually known in the fields of penicillin and cephalosporin, specifically including salts with mineral acids such as hydrochloric acid, nitric acid, sulfuric acid and the like; salts with organic carboxylic acids such as oxalic acid, succinic acid, formic acid, trichloroacetic acid, trifluoroacetic acid and the like; and salts with sulfonic acids such as methanesulfonic acid, ethanesulfonic acid, benzenesulfonic acid, toluene-2-sulfonic acid, toluene-4-sulfonic acid, mesitylenesulfonic acid (2,4,6-trimethylbenzenesulfonic acid), naphthalene-1-sulfonic acid, naphthalene-2 sulfonic acid, phenylmethanesulfonic acid, benzene-1,3-disulfonic acid, toluene-3,5-disulfonic acid, naphthalene-1,5-disulfonic acid, naphthalene-2,6-disulfonic acid, naphthalene-2,7-disulfonic acid, benzene-1,3,5-trisulfonic acid, benzene-1,2,4-trisulfonic acid, naphthalene-1,3,5-trisulfonic acid and the like (as the salts at the basic group), and salts with alkali metals such as sodium, potassium and the like; salts with alkaline earth metals such as calcium, magnesium and the like; ammonium salts; salts with nitrogen-containing organic bases such as procaine, dibenzylamine, N-benzyl-$\beta$-phenethylamine, 1-ephenamine, N,N-dibenzylethylenediamine, triethylamine, trimethylamine, tributylamine, pyridine, dimethylaniline, N-methylpiperidine, N-methylmorpholine, diethylamine, dicyclohexylamine and the like (as the salts at the acidic group).

Further, this invention covers all the optical isomers, racemic compounds, and all crystal forms and hydrates of the compounds represented by the formula [I] and their salts.

Among the compounds of this invention represented by the formula [I], preferred are those in which A is a group represented by

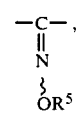

among which those in which $R^5$ is a hydrogen atom or a methyl group are more preferable. When $R^5$ is a methyl group, syn isomers are particularly preferable. Other examples of preferable compounds are those in which $R^2$ is a substituted or unsubstituted triazolyl or tetrazolyl group attached to the exomethylene group at the 3-position of the cephem ring, among which those in which $R^2$ is a substituted or unsubstituted 1,2,4-triazolyl or 2-(1,2,3,4-tetrazolyl) group are particularly preferable.

The results of a test for the pharmacological effect of the typical compounds of this invention are as follows:
(1) Antibacterial activity According to the standard method of the Japanese Chemotherapeutic Society [Chemotherapy, Vol. 23, Pages 1-2 (1975)], a culture obtained by cultivating bacteria in Heart Infusion broth (manufactured by Eiken Kagakusha) at 37° C. for 20 hours was inoculated into a Heart Infusion agar medium (manufactured by Eiken Kagakusha) and cultivated at 37° C. for 20 hours, after which the growth of bacteria was examined visually. The minimum inhibitory concentration at which the bacterial growth was inhibited was taken as MIC ($\mu$g/ml). The amount of the inoculated bacteria was $10^4$ cells/plate ($10^6$ cells/ml).

Test compounds:
(A) Trifluoroacetic acid salt of 7-[2-(2-aminothiazol-4-yl)-2-(syn)-methoxyiminoacetamido]-3-[(3-acetamido-1,2,4-triazolyl)methyl]-$\Delta^3$-cephem-4-carboxylic acid*,
(B) Trifluoroacetic acid salt of 7-[2-(2-aminothiazol-4-yl)-2-(syn)-methoxyiminoacetamido]-3-(furan-2-yl-carboxamido)methyl-$\Delta^3$-cephem-4-carboxylic acid,
(C) Trifluoroacetic acid salt of 7-[2-(2-aminothiazol-4-yl)-2-(syn)-methoxyiminoacetamido]-3-acetamidomethyl-$\Delta^3$-cephem-4-carboxylic acid,
(D) Trifluoroacetic acid salt of 7-[2-(2-aminothiazol-4-yl)-2-(syn)-methoxyiminoacetamido]-3-(4-hydroxybenzyl)-$\Delta^3$-cephem-4-carboxylic acid, (E) Trifluoroacetic acid salt of 7-[2-(2-aminothiazol-4-yl)-2-(syn)-hydroxyiminoacetamido]-3-[2-(5-methyl-1,2,3,4-tetrazolyl)methyl]-Δ3-cephem-4-carboxylic acid,
(F) Trifluoroacetic acid salt of 7-[2-(2-aminothiazol-4-yl)-2-(syn)-methoxyiminoacetamido]-3-[2-(1,2,3,4-tetrazolyl)methyl]-Δ3-cephem-4-carboxylic acid,
(G) Trifluoroacetic acid salt of 7-[2-(2-aminothiazol-4-yl)-2-(syn)-methoxyiminoacetamido]-3-[1-(1,2,3,4-tetrazolyl)methyl]-Δ3-cephem-4-carboxylic acid,
(H) Trifluoroacetic acid salt of 7-[2-(2-aminothiazol-4-yl)-2-(syn)-methoxyiminoacetamido]-3-[2-(5-amino-1,2,3,4-tetrazolyl)methyl]-Δ3-cephem-4-carboxylic acid,
(I) Trifluoroacetic acid salt of 7-[2-(2-aminothiazol-4-yl)-2-(syn)-methoxyiminoacetamido]-3-[2-(5-acetamido-1,2,3,4-tetrazolyl)methyl]-Δ3-cephem-4-carboxylic acid,
(J) Trifluoroacetic acid salt of 7-[2-(2-aminothiazol-4-yl)-2-(syn)-methoxyiminoacetamido]-3-[2-(5-methyl-1,2,3,4-tetrazolyl)methyl]-Δ3-cephem-4-carboxylic acid,
(K) Trifluoroacetic acid salt of 7-L2-(2-aminothiazol-4-yl)-2-(syn)-methoxyiminoacetamido]-3-[2-(5-ethyl-1,2,3,4-tetrazolyl)methyl]-Δ3-cephem-4-carboxylic acid,
(L) Trifluoroacetic acid salt of 7-[2-(2-aminothiazol-4-yl)-2-(syn)-methoxyiminoacetamido]-3-[(3-chloro-1,2,4-triazolyl)methyl]-Δ3-cephem-4-carboxylic acid*,
(M) Trifluoroacetic acid salt of 7-[2-(2-aminothiazol-4-yl)acetamido]-3-[2-(5-acetamido-1,2,3,4-tetrazolyl)methyl]-Δ3-cephem-4-carboxylic acid, and
(N) Trifluoroacetic acid salt of 7-[2-(2-aminothiazol-4-yl)acetamido]-3-[2-(1,2,3,4-tetrazolyl)methyl]-Δ3-cephem-4-carboxylic acid

* Those compounds were obtained in Example 21, etc. and the position of bond of 1,2,4-triazolyl is not specified because the 1,2,4-triazole was attached to the exomethylene group at the 3-position of the cephem ring through a carbon-nitrogen bond but it was not confirmed which of the nitrogen atoms of 1,2,4-triazolyl group was attached to the exomethylene group at the 3-position of the cephem ring. Moreover, the position of the substituent on the 1,2,4-triazolyl group is specified by referring to the position of the substituent in the starting compound used. The same applies in this specification when it was not confirmed which of the nitrogen atoms in 1,2,4-triazole is attached to the exomethylene group at the 3-position of the cephem ring. For example, the compound in which 3-methyl-1,2,4-triazole, 3-methylthio-1,2,4-triazole, 3-acetamido-1,2,4-triazole, 3-chloro-1,2,4-triazole, 3-ethoxycarbonyl-1,2,4-triazole or the like is attached to the exomethylene at the 3-position of the cephem ring are named "— -3-[(3-methyl-1,2,4-triazolyl)methyl]- —", "— -3-[(3-methylthio-1,2,4-triazolyl)methyl- —", "— -3-[(3-acetamido-1,2,4-triazolyl)methyl]- —", "— -3-[(3-chloro-1,2,4-triazolyl)methyl]- —" or "— -3-[(3-ethoxycarbonyl-1,2,4-triazolyl)methyl] - —", respectively. The nomenclature of 1,2,3-triazolyl-substituted compounds is the same as the above-mentioned method in the case of 1,2,4-triazolyl-substituted compounds.

TABLE 1

Antibacterial Activity MIC (μg/ml)

| Bacteria | Cephazoline | Compound A | B | C | D | E | F | G |
|---|---|---|---|---|---|---|---|---|
| E. coli NIHJ | 1.56 | ≦0.1 | ≦0.1 | ≦0.1 | ≦0.1 | ≦0.1 | ≦0.1 | ≦0.1 |
| E. coli TK3 (Penicillinase-producing bacteria) | 25 | 0.39 | 0.39 | 0.39 | 1.56 | 0.78 | ≦0.1 | 0.39 |
| Kl. pneumoniae Y-50 | 1.56 | ≦0.1 | ≦0.1 | ≦0.1 | 0.2 | ≦0.1 | ≦0.1 | ≦0.1 |
| Klebsiella spp Y-72 | >200 | 6.25 | 1.56 | 6.25 | 6.25 | 3.13 | — | — |
| Kl. pneumoniae Y-41 | 3.13 | 0.2 | 0.2 | 0.2 | 0.78 | 0.2 | ≦0.1 | 0.2 |
| Ent. cloacae IID977 | >200 | 6.25 | 25 | 50 | 25 | 6.25 | 12.5 | 6.25 |
| Ser. marcescens IID620 | >200 | 0.78 | 0.2 | 1.56 | 3.13 | 3.13 | 0.39 | 1.56 |
| Pro. morganii T-216 | >200 | 0.2 | 0.39 | 0.78 | 0.78 | ≦0.1 | ≦0.1 | 0.2 |
| Pro. mirabilis T-111 | 6.25 | 0.2 | 0.2 | 0.39 | 0.78 | 0.39 | ≦0.1 | 0.2 |
| Pro. mirabilis T-100 | — | ≦0.1 | ≦0.1 | ≦0.1 | ≦0.1 | ≦0.1 | — | — |
| Pro. vulgaris GN76 (Cephalosporinase-producing bacteria) | >200 | 3.13 | 0.78 | 6.25 | 1.56 | 6.25 | 0.78 | 0.78 |
| Al. faecalis B-1 | 100 | 50 | 12.5 | 12.5 | 25 | 3.13 | 3.13 | 12.5 |
| Aci. calcoaceticus A-6 | 200 | 25 | 25 | 12.5 | 6.25 | 50 | 6.25 | 25 |

| Bacteria | Compound H | I | J | K | L | M | N |
|---|---|---|---|---|---|---|---|
| E. coli NIHJ | ≦0.1 | ≦0.1 | ≦0.1 | ≦0.1 | ≦0.1 | 0.39 | 0.39 |
| E. coli TK3 (Penicillinase-producing bacteria) | 0.78 | 0.39 | 0.39 | 0.39 | 0.39 | 1.56 | 1.56 |
| Kl. pneumoniae Y-50 | 0.2 | ≦0.1 | ≦0.1 | 0.2 | ≦0.1 | 0.78 | 0.39 |
| Klebsiella spp Y-72 | — | — | — | — | — | — | — |
| Kl. pneumoniae Y-41 | 0.39 | 0.2 | ≦0.39 | 0.78 | 0.39 | 0.78 | 0.78 |
| Ent. cloacae IID977 | 12.5 | — | — | — | — | — | — |
| Ser. marcescens IID620 | 0.78 | — | — | — | — | — | — |
| Pro. morganii T-216 | 0.78 | — | — | — | — | — | — |
| Pro. mirabilis T-111 | 0.39 | ≦0.1 | 0.2 | 0.78 | 0.78 | 0.78 | 0.78 |
| Pro. mirabilis T-100 | — | ≦0.1 | ≦0.1 | ≦0.1 | ≦0.1 | 0.39 | 0.39 |
| Pro. vulgaris GN76 (Cephalosporinase-producing bacteria) | 1.56 | — | — | — | — | — | — |
| Al. faecalis B-1 | 12.5 | — | — | — | — | — | — |
| Aci. calcoaceticus A-6 | 25 | — | — | — | — | — | — |

(2) Oral administration experiment

Each test compound was administered orally to mice (ICR, male, 4 weeks old) at a dose of 2 mg per head, and the recovery of the compound from urine was determined. The results are shown in Table 2. After being absorbed in living body, all the test compounds were readily freed from the ester group to give the corresponding free carboxylic acids. Therefore, the free carboxylic acid excreted into urine was quantitatively analyzed and taken as recovery from urine.

Method of administration:

The test compound was suspended in 0.5% CMC solution and then orally administered.

The quantitative analysis were carried out by a paper disc method with the testing bacteria mentioned in Table 2.

TABLE 2

$$\text{HCl·H}_2\text{N}-\underset{S}{\overset{N}{\diagdown}}\!\!\!\!\diagup\!\!-\text{A}-\text{CONH}-\!\!\!\begin{array}{c}\text{S}\\ \text{azetidinone}\end{array}\!\!\!-\text{CH}_2\text{R}^2,\ \text{COOR}^1$$

| Compound | | | Recovery from | Testing |
|---|---|---|---|---|
| A | $R^1$ | $R^2$ | urine (%)* | bacteria |
| —CH$_2$— | —CH$_2$OCOC(CH$_3$)$_3$ | tetrazolyl (N=N, —N–N–N=) | 45.1 | M. luteus ATCC9341 |
| —CH$_2$— | " | 1-methyltetrazolyl (N=N, —N–N–N=, CH$_3$) | 32.0 | M. luteus ATCC9341 |
| —C— (syn) ‖ N—OCH$_3$ | " | " | 33.1 | M. luteus ATCC9341 |
| " | —CH(CH$_3$)—OCOC(CH$_3$)$_3$ | " | 35.0 | M. luteus ATCC9341 |
| —C— (syn) ‖ N—OCH$_3$ | —CH$_2$OCOC(CH$_3$)$_3$ | oxadiazolyl (N—N, O, Cl) | 47.0 | Kl. pneumoniae ATCC10031 |
| —C— (syn) ‖ N—OH | " | 1-methyltetrazolyl (N=N, —N–N–N=, CH$_3$) | 28.8 | M. luteus ATCC9341 |

Note:
*0-4 hrs.; average value of 5 cases.

Method of quantitative analysis:

(3) Acute toxicity test

Three test compounds were introvenously administered to mice (ICR, male, 4 weeks old) to test their acute toxicities. The results are as shown in Table 3.

TABLE 3

| Test Compound | LD$_{50}$ (g/kg) |
|---|---|
| $\text{NH}_2-\underset{S}{\overset{N}{\diagdown}}\!\!\!\!\diagup\!\!-\text{CH}_2\text{CONH}-[\beta\text{-lactam}]-\text{CH}_2\text{N-tetrazolyl(CH}_3\text{)},\ \text{COOH}$ | >3.0 |
| $\text{NH}_2-\underset{S}{\overset{N}{\diagdown}}\!\!\!\!\diagup\!\!-\overset{\|}{\underset{\underset{(syn)}{OCH_3}}{C}}\!\!-\text{CONH}-[\beta\text{-lactam}]-\text{CH}_2\text{N-tetrazolyl(CH}_3\text{)},\ \text{COOH}$ | >3.0 |

TABLE 3-continued

| Test Compound | LD$_{50}$ (g/kg) |
|---|---|
| 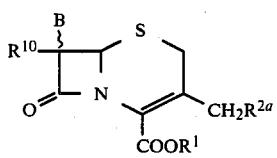 | >3.0 |

The compounds represented by the formula [I] and their salts can be administered to human and animals in the form of free acid, non-toxic salt or physiologically acceptable ester for the purpose of treating and preventing bacterial infectious diseases. It is preferred that the compounds be parenterally administered in the form of free acid or non-toxic salt or orallyl administered in the form of physiologically acceptable ester. In these cases, they may be prepared into preparation forms which are conventionally applied to cephalosporin drugs, such as tablet, capsule, powder, granule, fine granule, syrup, injection (including drop), suppository and the like. In producing the above-mentioned drugs, there may, if necessary, be used diluents and/or additives including excipients such as starch, lactose, sucrose, calcium phosphate, calcium carbonate and the like, binders such as gum arabic, starch, crystalline cellulose, carboxymethyl cellulose, hydroxypropyl cellulose and the like, lubricants such as talc, magnesium stearate and the like, and disintegrators such as carboxymethyl calcium, talc and the like.

In administering the cephalosporin preparation of this invention to human, the dose and the number of repetitions of administration are appropriately selected depending on the condition-of illness and others. It is usual, however, to administer the preparation either orally or parenterally at a dose of about 50–5,000 mg of the ecephalosporin compound of this invention at 1–4 times a day, per adult.

This invention provides not only the compounds represented by the formula [I] and salts thereof mentioned hereinbefore and processes for producing the same, which processes will be mentioned below, but also intermediates represented by the formulas [IIIb], [IV] and [V] and salts thereof which will be described below and a process for producing an intermediate represented by the formula [IIIa] and salts thereof, which process will be described hereinafter.

[IIIa]

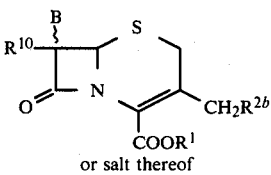

-continued
or salt thereof

[IIIb]

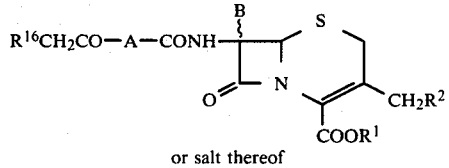

or salt thereof

[IV]

or salt thereof

[V]

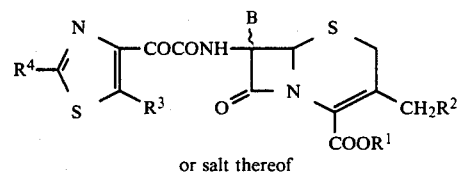

or salt thereof wherein R$^1$, R$^2$, R$^3$, R$^4$, A and B are as defined above; R$^{2a}$ represents a substituted or unsubstituted triazolyl or tetrazolyl group attached to the exomethylene group at the 3-position of the cephem ring through a carbon-nitrogen bond as explained as to R$^2$; R$^{2b}$ represents a substituted or unsubstituted 1,2,4-triazolyl or 2-(1,2,3,4-tetrazolyl)group; R$^{16}$ represents a halogen atom; and R$^{10}$ is as defined below.

An explanation is made below of the process for producing these compounds of this invention. That is, these compounds can be produced, for example, by the reaction route shown below.

Though the intermediate of this invention and its salt have per se an antibacterial activity, they are useful compounds convertible to the novel cephalosporins represented by the formula [I], as can be understood from the reaction routes shown below.

Reaction Routes
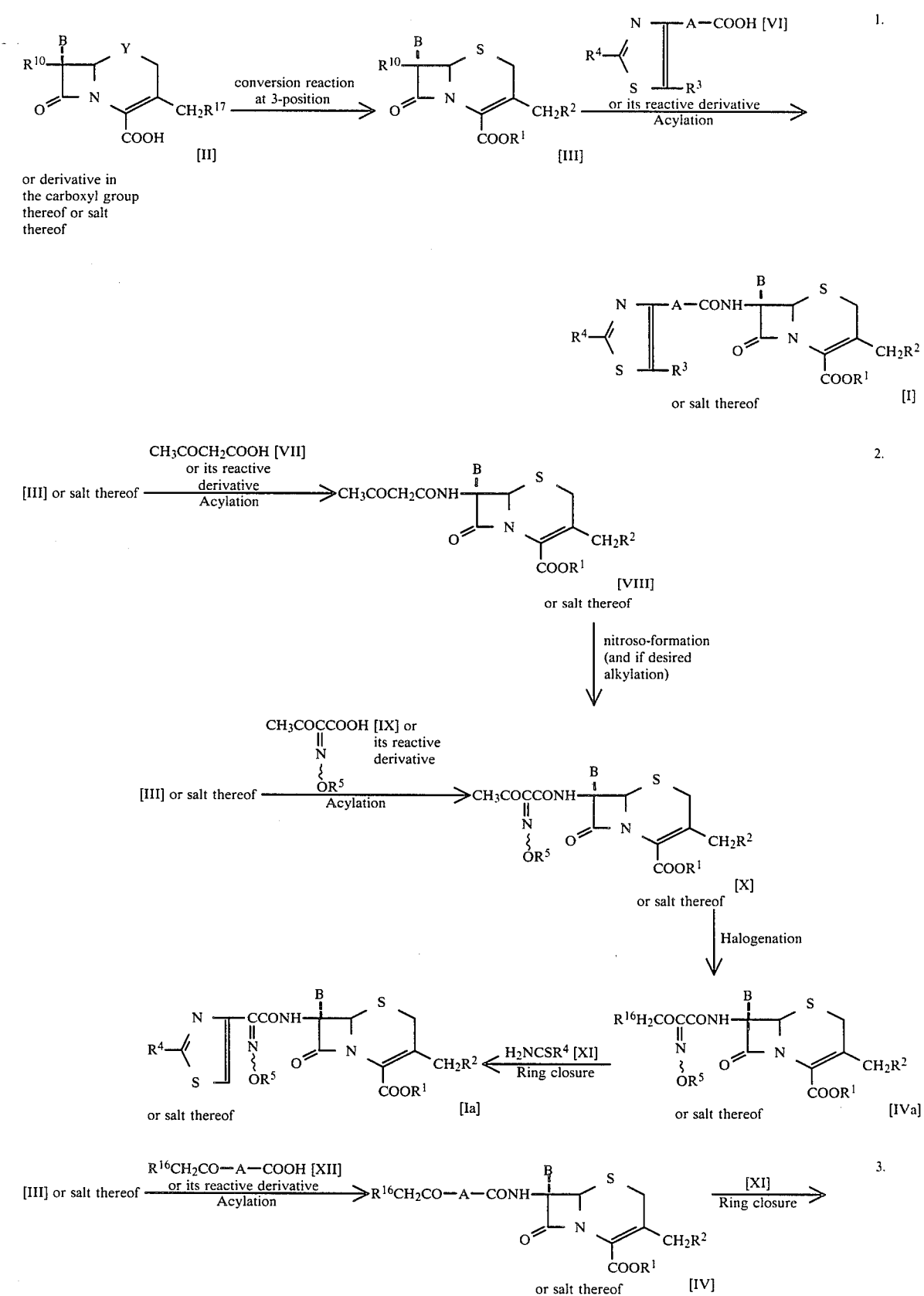

-continued
Reaction Routes

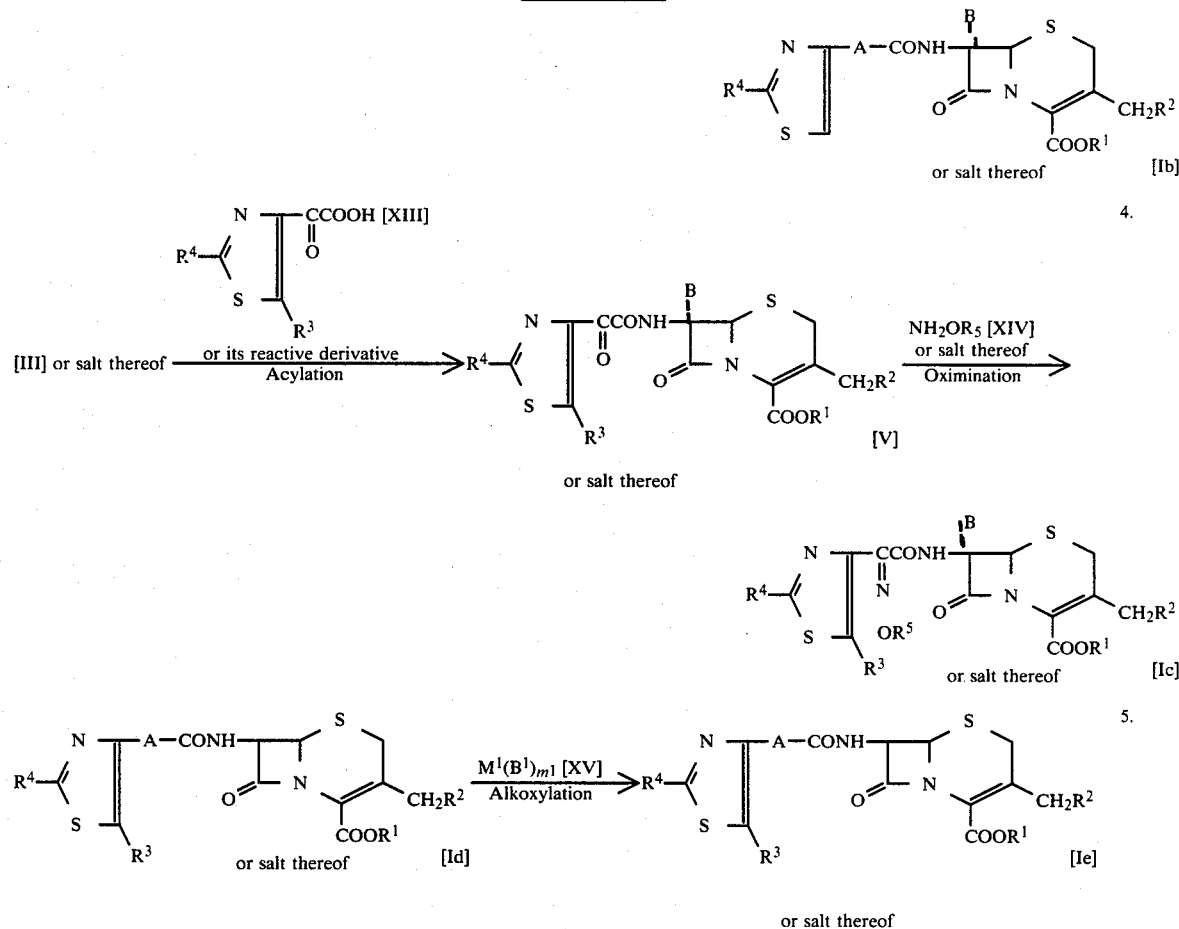

wherein $R^1$, $R^2$, $R^3$, $R^4$, $R^5$, A, B and the bond are as defined above; $B^1$ represents the lower alkoxy group mentioned as to B; Y represents —S—, or

$M^1$ represents an alkali metal atom or an alkaline earth metal atom; $m^1$ represents an integer of 1 or 2; $R^{10}$ represents an amino group, a group of the formula,

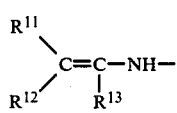

in which $R^{11}$, $R^{12}$ and $R^{13}$, which may be identical or different, represent hydrogen atoms or organic residues not participating in the reaction, or a group of the formula,

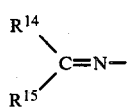

in which $R^{14}$ and $R^{15}$, which may be identical or different, represents hydrogen atoms or organic residues not participating in the reaction; and $R^{17}$ represents a substituted or unsubstituted acyloxy or carbamoyloxy group.

In the compounds represented by the formulas [II] and [III] and their salts, $R^{10}$ includes an amino group, a group represented by the formula,

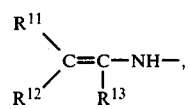

and a group represented by the formula,

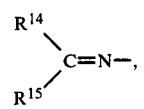

and the group represented by the formula,

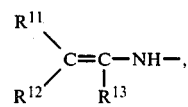

means to include a group represented by the formula,

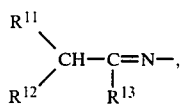

which is an isomer of the former.

As the organic residue not participating in the reaction at $R^{11}$, $R^{12}$, $R^{13}$, $R^{14}$ and $R^{15}$ in the above-mentioned formulas, there may be used substituted or unsubstituted aliphatic, alicyclic, aromatic, ar-aliphatic, heterocyclic, and acyl residues, and the following groups may specifically be mentioned:

(1) Aliphatic residues: for example, alkyl groups and alkenyl groups,
(2) Alicyclic residues: for example, cycloalkyl groups and cycloalkenyl groups,
(3) Aromatic residues: for example, aryl groups,
(4) Ar-aliphatic residues: for example, aralkyl groups,
(5) Heterocyclic residues: for example, heterocyclic groups,
(6) Acyl groups: acyl groups which can be derived from organic carboxylic acids, and examples of said organic carboxylic acids are aliphatic carboxylic acids; alicyclic carboxylic acids; alicycloaliphatic carboxylic acids; aromatic-substituted aliphatic carboxylic acids; aromatic-oxyaliphatic carboxylic acids; aromatic-thioaliphatic carboxylic acids; heterocycle-substituted aliphatic carboxylic acids; heterocyclic-oxyaliphatic carboxylic acids; or heterocyclic-thioaliphatic carboxylic acids; organic carboxylic acids in which an aromatic ring, aliphatic group or alicylic group is attached to the carbonyl group through an oxygen, nitrogen or sulfur atom; aromatic carboxylic acids; heterocyclic carboxylic acids; and the like.

As said aliphatic carboxylic acids, there may be mentioned formic acid, acetic acid, propionic acid, butanoic acid, isobutanoic acid, pentanoic acid, methoxyacetic acid, methylthioacetic acid, acrylic acid, crotonic acid and the like; and as said alicyclic carboxylic acids, there may be mentioned cyclohexanoic acid and the like; and as said alicycloaliphatic carboxylic acids, there may be mentioned cyclopentane-acetic acid, cyclohexane-acetic acid, cyclohexanepropionic acid, cyclohexadiene-acetic acid and the like.

As the aromatic residue in the above-mentioned organic carboxylic acids, the aryl groups mentioned hereinbefore as examples can be used; and as said heterocyclic ring, there may be used the heterocyclic groups mentioned hereinbefore as examples.

Further, the individual groups constituting these organic carboxylic acids may additionally be substituted by a substituent such as halogen, hydroxyl, protected hydroxyl, alkyl, alkoxy, acyl, nitro, amino, protected amino, carboxyl, protected carboxyl, or the like.

As said protecting group for amino, hydroxyl and carboxyl groups, the protecting groups mentioned as to $R^2$ may be used.

The derivatives of the compound of the formula [II] at its carboxyl group include, for example, the followings:

(a) Esters: Esters conventionally used in the fields of penicillin and cephalosporin may be used, and include specifically the esters mentioned as to $R^1$.
(b) Anhydrides of the carboxyl group with N-hydroxysuccinimide, N-hydroxyphthalimide, dimethylhydroxylamine, diethylhydroxylamine, 1-hydroxypiperidine, oxime and the like.
(c) Amides: Acid amides, N-substituted acid amides and N,N-disubstituted acid amides are all included, and there may specifically be mentioned N-alkyl acid amides such as N-methyl acid amide, N-ethyl acid amide and the like; N-aryl acid amides such as N-phenyl acid amide and the like; N,N-dialkyl acid amides such as N,N-dimethyl acid amide, N,N-diethyl acid amide, N-ethyl-N-methyl acid amide and the like; and acid amides with imidazole, 4-substituted imidazole, triazolopyridone and the like.

As the acyloxy and carbamoyloxy groups for $R^{17}$, there may specifically be mentioned alkanoyloxy groups such as acetoxy, propionyloxy, butyryloxy and the like; alkenoyloxy groups such as acryloyloxy and the like; aroyloxy groups such as benzoyloxy, naphthoxyloxy and the like; and carbamoyloxy group. They may be substituted by one or more substituents such as halogen, nitro, alkyl, alkoxy, alkylthio, acyloxy, acylamino, hydroxyl, carboxyl, sulfamoyl, carbamoyl, carboalkoxycarbamoyl, aroylcarbamoyl, carboalkoxysulfamoyl, aryl, carbamoyloxy, and the like.

In the above-mentioned substituents on $R^{17}$, the hydroxyl, amino, and carboxyl groups may be protected with conventional protecting groups. As the protecting group, there may be used the protecting groups for hydroxyl, amino and carboxyl groups mentioned as to $R^2$.

The salts referred to in the above-mentioned reaction route diagram include both of the salts at acidic group and the salts at basic group, and specifically, the salts mentioned as to the compound represented by the formula [I] may be used.

This invention also covers all the isomers of the intermediates (for example, syn and anti isomers, tautomers, optical isomers and the like), as well as their mixtures, all crystalline forms and hydrates.

Further, an explanation is made of the process for producing the compounds represented by the formulas [I] (including [Ia], [Ib], [Ic], [Id] and [Ie]), [III] (including [IIIa] and [IIIb]), [IV] (including [IVa]), [V], [VIII] and [X] and their salts. The reaction routes to produce these compounds are as shown in the above reaction route diagram.

(1) In the conversion reaction at 3-position of route 1, 7-substituted or unsubstituted amino-3-substituted methyl-Δ³-cephem-4-carboxylic acids represented by the formula [III] (including [IIIa] and [IIIb], too; hereinafter the same applies) or their salts can be produced by reacting the cephalosporanic acid represented by the formula [II] or its derivative in the carboxyl group or a salt thereof with a substituted or unsubstituted aromatic hydrocarbon, a substituted or unsubstituted nitrile compound, a substituted or unsubstituted aromatic heterocyclic compound or triazole or tetrazole, which may have substituents on the carbon atoms in the ring, in an organic solvent in the presence of an acid or an acid complex compound and subsequently, if desired, removing the protecting group, protecting the carboxyl group or converting the carboxyl group to a salt. Further, if necessary, the substituent on the 7-amino group may be removed by a conventional method to give a 7-unsubstituted amino compound.

According to this production process, the compound represented by the formula [II], its derivative in the carboxyl group or a salt thereof may be reacted with a substituted or unsubstituted aromatic hydrocarbon to obtain a compound of the formula [III] or its salt in which $R^2$ is the corresponding aromatic hydrocarbon group, or similarly, reacted with a substituted or unsubstituted nitrile compound to obtain a compound of the formula [III] or its salt in which $R^2$ is the corresponding acylamino group, or similarly, reacted with a substituted or unsubstituted aromatic heterocyclic compound to obtain a compound of the formula [III] or its salt in which $R^2$ is the corresponding aromatic heterocyclic group, or similarly, reacted with triazole or tetrazole, which may have substituents on the carbon atoms in the ring to obtain a compound of the formula [III] or its salt in which $R^2$ is the corresponding substituted or unsubstituted triazolyl or tetrazolyl group (namely, a compound of the formula [IIIa] or its salt). In all the above cases, the reaction is conducted by an industrially easy operation to obtain the product in a high yield with a high purity.

As the substituted or unsubstituted aromatic hydrocarbon which is the reactant in said reaction, there may be used an aromatic hydrocarbon corresponding to the substituted or unsubstituted aromatic hydrocarbon group for $R^2$, namely an aromatic hydrocarbon represented by $R^2H$ ($R^2$ means the substituted or unsubstituted aromatic hydrocarbon group mentioned above as to $R^2$). As said substituted or unsubstituted nitrile compound, there may similarly be used a nitrile compound corresponding to the substituted or unsubstituted acylamino group for $R^2$, namely a nitrile compound represented by $R^9CN$ ($R^9$ is as defined above). As the substituted or unsubstituted aromatic heterocyclic compound, there may be similarly used an aromatic heterocyclic compound corresponding to the substituted or unsubstituted aromatic heterocyclic group for $R^2$, namely an aromatic heterocyclic compound represented by $R^2H$ ($R^2$ means the substituted or unsubstituted aromatic heterocyclic group mentioned above as to $R^2$). As the triazole or tetrazole which may have substitutens on the carbon atoms in the ring, there may similarly be used a triazole or tetrazole corresponding to the substituted or unsubstituted triazolyl or tetrazolyl group for $R^2$, namely a triazole or tetrazole represented by $R^2H$ ($R^2$ means the substituted or unsubstituted triazolyl or tetrazolyl group mentioned above as to $R^2$).

In these triazoles and tetrazoles, tautomers exist as shown below. Any of these isomers and any of their mixtures may be used in the reaction.

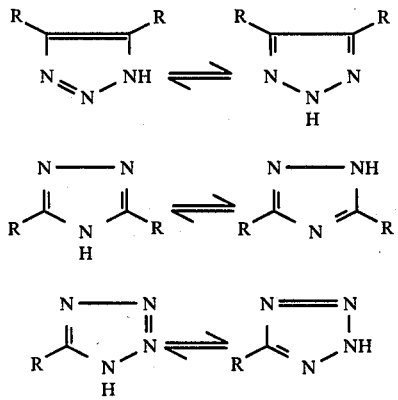

wherein R represents a hydrogen atom or the substituents mentioned above at to $R^2$, and the two R's may be identical or different.

The triazoles and tetrazoles which may have substituents on the carbon atoms in the ring may, if necessary, be used in the form of a basic salt or an acidic salt for the reaction. As said basic salt and acidic salt, there may be used the same salt forms as the salts in the carboxyl group and amino group mentioned as to the salt of the compound represented by the formula [I]. The salt of the compound represented by the formula [II] may previously be isolated and then used, or may be prepared in situ.

As the acid or acid complex compound used in the above reaction, probonic acids, Lewis acids and complex compounds of Lewis acids may be used. As the protonic acid, there may be mentioned sulfuric acids, sulfonic acids and super-acids (the term "super-acids" means acids stronger than 100% sulfuric acid and includes some of the above-mentioned sulfuric acids and sulfonic acids). Specifically, there may be used sulfuric acid, chlorosulfuric acid, fluorosulfuric acid and the like as the sulfuric acids; alkyl(mono- or di-)sulfonic acids, for example, methanesulfonic acid, trifluoromethanesulfonic acid and the like and aryl(mono-, di- or tri-)sulfonic acids, for example, p-toluenesulfonic acid and the like as the sulfonic acids; and perchloric acid, magic acid ($FSO_3H\text{-}SbF_3$), $FSO_3H\text{-}AsF_5$, $CF_3SO_3H\text{-}SbF_5$, $HF\text{-}BF_3$, $H_2SO_4\text{-}SO_3$ and the like as the super-acids. As the Lewis acids, boron trifluoride may be mentioned as an example. As the complex compound of Lewis acid, there may be mentioned complex salts of boron trifluoride with dialkyl ethers such as diethyl ether, di-n-propyl ether, di-n-butyl ether and the like; complex salts of boron trifluoride with amines such as ethylamine, n-propylamine, n-butylamine, triethanolamine and the like; complex salts of boron trifluoride with carboxylic esters such as ethyl formate, ethyl acetate and the like; complex salts of boron trifluoride with aliphatic acids such as acetic acid, propionic acid and the like; complex salts of boron trifluoride with nitriles such as acetonitrile, propionitrile and the like.

As the organic solvent in this reaction, all the organic solvents which do not adversely affect the reaction may be used, and there may specifically be mentioned nitroalkanes such as nitromethane, nitroethane, nitropropane and the like; organic carboxylic acids such as formic acid, acetic acid, trifluoroacetic acid, dichloroacetic acid, propionic acid and the like; ketones such as acetone, methyl ethyl ketote, methyl isobutyl ketone and the like; ethers such as diethyl ether, diisopropyl ether, dioxane, tetrahydrofuran, ethylene glycol dimethyl ether, anisole and the like; esters such as ethyl formate, diethyl carbonate, methyl acetate, ethyl acetate, ethyl chloroacetate, butyl acetate and the like; nitriles such as acetonitrile, butyronitrile and the like; and sulfolanes such as sulfolane and the like. These solvents may be used alone or in admixture of two or more. Furthermore, complex compounds formed from these organic solvents and Lewis acids may also be used as the solvent. The amount of the acid or complex compound of acid used is 1 mole or more per mole of the compound represented by the formula [II] or its derivative in the carboxyl group or the salt thereof, and may be varied depending upon the conditions. It is particularly preferable to use the acid or complex compound of acid in an amount of 2-10 moles per mole of the latter. When the complex compound of acid is used, it may per se be used as a solvent or a mixture of two or more complex compounds may be used.

The amount of the aromatic hydrocarbon, nitrile compound, aromatic heterocyclic compound or triazole or tetrazole used as a reactant for the above reaction is 1 mole or more per mole of the compound represented by the formula [II] or its derivative in the carboxyl group or the salt thereof. It is particularly preferable to use them in an amount of 1.0–5.0 moles per mole of the latter.

This reaction is usually carried out at a temperature of 0°–80° C., and the reaction time is generally several minutes to tens of hours. If water exists in the system of this reaction, there is a fear that undesirable side reactions such as lactonization of the starting compound or product and cleavege of the β-lactam ring be caused. Therefore, the reaction system is preferably kept in an anhydrous state. In order to fulfil this requirement, to the reaction system may be added an appropriate dehydrating agent such as a phosphorus compound (for example, phosphorus pentoxide, polyphosphoric acid, phosphorus pentachloride, phosphorus trichloride, phosphorus oxychloride or the like), an organic silylating agent (for example, N,O-bis(trimethylsilyl)acetamide, trimethylsilylacetamide, trimethylchlorosilane, dimethyldichlorosilane or the like), an organic acid chloride (for example, acetyl chloride, p-toluenesulfonyl chloride or the like), an acid anhydride (for example, acetic anhydride, trifluoroacetic anhydride or the like), an inorganic drying agent (for example, anhydrous magnesium sulfate, anhydrous calcium chloride, molecular sieve, calcium carbide or the like), or the like.

If a derivative in the carboxyl group of the compound of the formula [II] is used as the starting compound in the above reaction, there can, in some cases, be obtained, depending on the treatment after the reaction, the corresponding compound of the formula [III] having a free carboxyl group at the 4-position of the cephem ring. However, the corresponding compound of the formula [III] having a free carboxyl group at the 4-position can also be obtained by effecting the removal reaction in the conventional manner.

When a compound of the formula [III] in which $R^1$ is a hydrogen atom is obtained in this reaction, it can be esterified or converted to a salt in the conventional manner. When a compound of the formula [III] in which $R^1$ is an ester group is obtained, it can be subjected to removal reaction in the conventional manner to obtain a compound of the formula [III] in which $R^1$ is a hydrogen atom, which can subsequently be converted to a salt or other ester optionally. When a compound of the formula [III] in which $R^1$ is a salt-forming group is obtained, it can be subjected to a desalting reaction in the conventional manner to obtain a compound of the formula [III] in which $R^1$ is a hydrogen atom and further to that in which $R^1$ is an ester group, optionally.

When the substituent attached to the aromatic hydrocarbon, nitrile compound, aromatic heterocyclic compound or the carbon atom in the ring of the triazole or tetrazole which are reactants of the above reaction is substituted by hydroxyl, amino, or carboxyl, the desired compound can be obtained by first protecting these groups with the aforementioned protecting group before carrying out the reaction and subjecting it, after completion of the reaction, to the conventional removal reaction.

When a compound of the formula [III] in which $R^2$ is a substituted or unsubstituted aryl group or an aromatic heterocyclic group attached to the exomethylene group at the 3-position of the cephem ring through a carbon-carbon bond is obtained, there may be applied, in addition to the above-mentioned 3-position conversion reaction, a known method by which a penicillin as the starting material is subjected to the opening of the thiazolidine ring, then to the reaction with 3-$R^2$-prop-2-ynyl bromide to open the ring and thereafter to a series of reactions for forming a dihydrothiadine ring (namely the cephalosporin skeleton) (see Japanese Patent Application Kokai (Laid-Open) No. 5,393/75; J.M.C., 20, 1082 (1977); ibid., 20, 1086 (1977)).

When a compound of the formula [III] in which B is a hydrogen atom is obtained in the above reaction, it can be converted to a compound of the formula [III] in which B is a lower alkoxy group by loweralkoxylating the 7α-position of the formula [III] in a manner known in this field [the Journal of Synthetic Organic Chemistry, Japan, Vol. 35, 568–574 (1977)].

(2) The acylating reactions of routes 1–4 can be carried out all in substantially the same manner. In these acylating reactions, a compound represented by the formula [III] or a salt thereof is reacted with a compound represented by the formula [VI], [VII], [IX], [XII] or [XIII] or a reactive derivative thereof to obtain a compound represented by the formula [I], [IV], [V], [VIII] or [X] or a salt thereof.

As the reactive derivatives of the compounds represented by the formulas [VI], [VII], [IX], [XII] and [XIII], there may specifically mentioned acid halides, acid anhydrides, mixed acid anhydrides, active acid amides, active esters and the reactive derivatives formed between Vilsmeier reagent and the compound represented by the formula [VI], [VII], [IX], [XII] or [XIII]. As said mixed acid anhydride, there may be used mixed acid anhydrides with monoalkyl carbonates such as monoethyl carbonate, monoisobutyl carbonate and the like; and mixed acid anhydrides with lower alkanoic acids optionally substituted by halogen such as pivalic acid, trichloroacetic acid and the like. As said active acid amide, there may be used, for example, N-acylsaccharin, N-acylimidazole, N-acylbenzoylamide, N,N'-dicylcohexyl-N-acylurea, N-acylsulfonamide and the like. As said active ester, there may be used, for example, cyanomethyl esters, substituted phenyl esters, substituted benzyl esters, substituted thienyl esters and the like.

As said reactive derivative with Vilsmeier reagent, there may be used the reactive derivatives with a Vilsmeier reagent obtained by reacting an acid amide such as dimethylformamide, N,N-dimethylacetamide or the like with a halogenating agent such as phosgene, thionyl chloride, phosphorus trihloride, phosphorus tribromide, phoshporus oxychloride, phosphorus oxybromide, phosphorus pentachloride, trichloromethyl chloroformate, oxalyl chloride and the like.

When the compound of the formula [VI], [VII], [IX], [XII] or [XIII] is used in the state of a free acid or salt, an appropriate condensing agnet is used. As said condensing agent, there may be used N,N'-disubstituted carbodiimides such as N,N'-dicyclohexylcarbodiimide and the like, azolide compound such as N,N'-thionyldiimidazole and the like, dehydrating agents such as N-ethoxycarbonyl-2-ethoxy-1,2-dihydroxyquinoline, phosphorus oxychloride, alkoxyacetylene and the like, 2-halogenopyridinium salts such as 2-chloropyridinium methyl iodide, 2-fluoropyridinium methyl iodide and the like.

These acylating reactions are generally carried out in an appropriate solvent in the presence or absence of a base. As said solvent, there are often used halogenated hydrocarbons such as chloroform, methylene dichloride and the like, ethers such as tetrahydrofuran, dioxane and the like, dimethylformamide, dimethylacetamide, acetone, water and mixtures thereof. The base used herein includes inorganic bases such as alkali hydroxides, alkali hydrogen carbonates, alkali carbonates, alkali acetates and the like; tertiary amines such as trimethylamine, triethylamine, tributylamine, pyridine, N-methylpiperidine, N-methylmorpholine, lutidine, collidine and the like; and secondary amines such as dicyclohexylamine, diethylamine and the like.

The amount of the compound represented by the formula [VI], [VII], [IX], [XII] or [XIII] or its reactive derivative used in the acylating reactions of routes 1–4 is usually about 1 mole to several moles per mole of the compound represented by the formula [III] or its salt. The reaction is usually carried out at a temperature ranging from $-50°$ C. to $+40°$ C., and the reaction time is usually 10 minutes to 48 hours.

In the acylating reaction of route 3 wherein A is $-CH_2-$, a compound of the formula [XIII] wherein A is $-CH_2-$ or its salt can also be obtained by reacting the diketene and halogen according to the method of the Journal of the Chemical Society, 97, 1987 (1910) and then reacting the reaction product with a compound of the formula [III] or its salt.

When the compound obtained by the acylating reactions of routes 1–4 is a compound of the formula [I], [IV], [V], [VIII] or [X] wherein $R^1$ is a carboxylprotecting group, the compound can be converted in a conventional manner to the corresponding compound or its salt wherein $R^1$ is hydrogen; and when it is a compound of the formula [I], [IV], [V], [VIII] or [X] wherein $R^1$ is a hydrogen atom, the compound can be converted in a conventional manner to the corresponding compound or its salt wherein $R^1$ is a carboxyl-protecting group; and when it is a salt of the formula [I], [IV], [V], [VIII] or [X], the compound can be converted in a conventional manner to the corresponding free compound.

When, in these acylating reactions, there is a group active to the reaction among the groups $R^1$, $R^2$ and $R^4$, the active group may be protected in any manner with a conventional protecting group at the time of reaction, and the protecting group can be removed after the reaction in a conventional manner.

The compounds of the formulas [I], [IV], [V], [VIII] and [X] and their salts thus obtained can be isolated by a conventional method.

(3) When, in the compound represented by the formula [IV] or its salt obtained by the acylating reaction of route 3, A is $-CH_2-$, it may be subjected to a nitroso-forming reaction mentioned hereinafter (and optionally a subsequent alkylating reaction) to convert A into

and thereafter to a subsequent ring closure reaction.

The nitroso-forming reaction can be carried out in the following manner:

The reaction of a compound represented by the formula [VIII] or its salt with a nitroso-forming agent to convert it to a compound represented by the formula [VII] or its salt is usually carried out in a solvent. As said solvent, there may be used solvents which do not adversely affect the reaction such as water, acetic acid, benzene, methanol, ethanol, tetrahydrofuran and the like. The preferable examples of the nitroso-forming agent are nitric acid and its derivatives such as nitrosyl halides (for example, nitrosyl chloride, nitrosyl bromide and the like), alkali metal nitrites (for example, sodium nitrite, potassium nitrite and the like), alkyl nitrites (for example, butyl nitrite, pentyl nitrite and the like). When a salt of nitrous acid is used as the nitroso-forming agent, the reaction is preferably carried out in the presence of an inorganic or organic acid such as hydrochloric acid, sulfuric acid, formic acid, acetic acid or the like. When an ester of nitrous acid is used as the nitroso-forming agent, it is also possible to carry out the reaction in the presence of a strong base such as an alkali metal alkoxide. Though the reaction temperature is not critical, it is usually preferable to carry out the reaction with cooling or at room temperature. Salts of the compounds represented by the formula [X] wherein $R^5$ is a hydrogen atom can easily be obtained by a conventional method. Said salts may be the same as mentioned as to the salts of the compound of the formula [I]. The thus obtained compounds of the formula [X] wherein $R^5$ is a hydrogen atom, as well as their salts, can be isolated and purified in the well known manner. It is also possible, however, to use them as the starting compound for the subsequent reaction without separating them.

(4) After the above-mentioned nitroso-forming reaction, the product is subjected to alkylating reaction in order to obtain a compound of the formula [X] wherein $R^5$ is an alkyl group, and the alkylating reaction can be carried out according to the usual method. For example, it can be completed in several minutes to several hours in most cases if it is carried out in a solvent with cooling or in the neighborhood of room temperature. As the solvent, any solvent may be used so far as it does not retard this reaction, and the solvents usable include tetrahydrofuran, dioxane, methanol, ethanol, chloroform, methylene dichloride, ethyl acetate, butyl acetate, N,N-dimethylformamide, N,N-dimethylacetamide, water and the like and mixtures thereof.

As the alkylating agent, for example, methyl iodide, methyl bromide, ethyl iodide, ethyl bromide, dimethyl sulfate, diethyl sulfate, diazomethane, diazoethane, methyl p-toluenesulfonate and the like are used. When the alkylating agents other than diazomethane and diazoethane are used, the reaction is generally carried out in the presence of a base such as an alkali metal carbonate (for example, sodium carbonate, potassium carbonate or the like), an alkali metal hydroxide (for example, sodium hydroxide, potassium hydroxide or the like), triethylamine, pyridine, dimethylaniline or the like.

Salts of the compound represented by the formula [X] wherein $R^5$ is an alkyl group can be obtained easily according to the usual method. Said salts may be the same as the salts mentioned as to the salts of the compound represented by the formula [I]. The thus obtained compound of the formula [X] wherein $R^5$ is an alkyl group and salts thereof can be isolated and purified in the well known manner. However, it is also possible to use them as the starting compound for the subsequent reaction without separating them.

(5) The compound represented by the formula [IVa] or its salt is obtained by reacting the compound represented by the formula [X] or its salt with a halogenating agent in route 2. As the halogenating agent, there may be used halogens such as chlorine, bromine, iodine or the like; sulfuryl halides such as sulfuryl chloride or the like; haloimide compounds such as N-bromosudcinimide, N-chlorosuccinimide or the like; and halogen-pyridine complexes such as pyridinium hydrobromide perbromide or the like. The amount of the halogenating agent used in usually about 1 to several moles per mole of the compound represented by the formula [X]or its salt. Said reaction is preferably conducted in the presence of a Lewis acid such as aluminum chloride, boron trifluoride, titanium tetrachloride or the like. As the solvent, any solvent may be used as far as it does not adversely affect the reaction, and there may be used, for example, tetrahydrofuran, dioxane, chloroform, methylene chloride, benzene or the like alone or in admixture of two or more. The reaction may be conducted with cooling or at an elevated temperature for a period of 10 minutes to 24 hours.

(6) In the oximination reaction of route 4, a compound represented by the formula [V] or its salt is reacted with a compound represented by the formula [XIV] or its salt to obtain a compound of the formula [Ic] or its salt. The salt of the compound represented by the formula [XIV] includes the salts at basic group as mentioned hereinbefore. This reaction is usually carried out in a solvent such as water, an alcohol or the like or in other solvents which do not adversely affect the reaction or in a solvent mixture comprising them, and the reaction is usually carried out at 0° to 100° C., preferably 10° to 50° C. When a salt of the compound of the formula [XIV] is used in this reaction, the reaction is preferably carried out in the presence of a base including an inorganic base such as an alkali metal hydroxide (for example, sodium hydroxide, potassium hydroxide or the like), an alkaline earth metal hydroxide (for example, magnesium hydroxide, calcium hydroxide or the like), an alkali metal carbonate (for example, sodium carbonate, potassium carbonate or the like), an alkaline earth metal carbonate (for example, magnesium carbonate, calcium carbonate or the like), an alkali metal hydrogen carbonate (for example, sodium hydrogen carbonate, potassium hydrogen carbonate or the like), an alkaline earth metal phosphate (for example, magnesium phosphate, calcium phosphate or the like) and an alkali metal hydrogen phosphate (for example, disodium hydrogen phosphate, dipotassium hydrogen phosphate or the like) and an organic base such as an alkali metal acetate (for example, sodium acetate, potassium acetate or the like), a trialkylamine (for example, trimethylamine, triethylamine or the like), picoline, N-methylpyrrolidine, N-methylmorpholine, 1,5-diazabicyclo[4,3,0]-5-nonene, 1,4-diazabicyclo[2,2,2]octane, 1,5-diazabicyclo[5,4,0]-7-undecene and the like.

(7) The ring closure reactions of routes 2 and 3 can also be carried out in substantially the same manner. Thus, a compound represented by the formula [IV] (including [IVa]) or its salt is reacted with a thioformamide or thiourea represented by the formula [XI] to obtain a compound represented by the formula [Ia] or [Ib], respectively, or a salt thereof. This reaction is usually carried out in a solvent. As the solvent, any solvent may be used so far as it does not retard this reaction. Examples of the solvent usable are water, methanol, ethanol, acetone, tetrahydrofuran, dioxane, N,N-dimethylformamide, N,N-dimethylacetamide, N-methylpyrrolidone and the like, and they are used either alone or in admixture of two or more. Though the addition of a de-acidifying agent is not particularly necessary, the addition of de-acidifying agent sometimes smoothens the progress of reaction so far as it gives no change to the cephalosporin skeleton. As the de-acidifying agent used for this purpose, there are inorganic and organic bases such as alkali metal hydroxides, alkali metal hydrogen carbonates, triethylamine, pyridine, N,N-dimethylaniline and the like. The reaction is usually carried out at 0° to 100° C., preferably 10° to 50° C. Usually, 1 to several equivalents of a thioformamide or thiourea represented by the formula [XI] is used per equivalent of the compound of the formula [IV] (including [IVa]). The reaction time is generally 1–48 hours, preferably 1–10 hours. Further, the compounds of the formulas [Ia] and [Ib] can also be converted to the corresponding desired compounds by carrying out the protection of carboxyl group, its removal or salt formation according to a conventional method. Further, when groups $R^1$, $R^2$ and $R^4$ have a group active to this reaction, they can be protected with a conventional protecting group in any manner at the time of reaction, and the protecting group can be removed by a conventional method after the reaction. The objective compounds of the formula [Ia] or [Ib] or their salts, thus obtained, can be isolated by the usual method.

(8) In route 5, a compound represented by the formula [Ie] or its salt is prepared from a compound represented by the formula [Id] or its salt. For this purpose, a compound represented by the formula [Id] or its salt is dissolved or suspended in a solvent inert to the reaction, such as tetrahydrofuran, dioxane, ethylene glycol diethyl ether, methylene chloride, chloroform, diemthylformamide, N,N-dimethylacetamide, acetonitrile, methanol, ethanol or a mixture thereof.

To the resulting solution or suspension is added a compound represented by the formula [XV] together with a lower alcohol. The resulting mixture is subjected to reaction, and the reaction mixture is then reacted with a halogenating agent. In this reaction, a lower alcohol is used in excess and the amount of the compound [XV] used is preferably 2 to 6 equivalents per equivalent of the compound [Id] used. The term "in excess" means an amount of more than 1 equivalent per equivalent of the compound [Id]. All of the above reactions are carried out at $-120°$ to $-10°$ C., preferably $-100°$ to $-50°$ C. A reaction time of 5 to 30 minutes is sufficient and the reaction is terminated by acidifying the reaction system.

The halogenating agent used in this method is generally known to be a source for supplying a positive halogen atom such as $Cl^+$, $Br^+$ or $I^+$. Examples of such halogenating agents include halogens such as chlorine, bromine and the like; N-haloimides such as N-chlorosuccinimide, N-bromosuccinimide and the like; N-haloamides such as N-chloroacetamide, N-bromoacetamide and the like; N-halosulfonamides such as N-chlorobenzenesulfonamide, N-chloro-p-toluenesulfonamide and the like; 1-halobenzotriazoles; 1-halotriazines; organic hypohalogenites such a as tert.-butyl hypochlorite, tert.-butyl hypoiodite and the like; halohydantoins such as N,N-dibromohydantoin, and the like. Of these halogenating agents, tert.-butyl hypochlorite is preferred. The halogenating agent is used in an amount sufficient for supplying a positive halogen in an amount equivalent to that of the compound [Id].

Suitable acids for the termination of reaction are those which, when added to a cold reaction mixture, will not cause solidification of the reaction mixture or freezing of the reaction mixture into a heavy viscous mixture. Examples of the suitable acids are 98% formic acid, glacial acetic acid, trichloroacetic acid and methanesulfonic acid.

After the termination of the reaction, the excess halogenating agent can be removed by treating with a reducing agent such as trialkyl phosphite, sodium thiosulfate, or the like.

When B is a hydrogen atom in the compounds represented by the formulas [IVa], [VIII] and [X] in route 2, the compound represented by the formula [IV] in route 3 and the compound represented by the formula [V] in route 4 and their salts, it is also possible to convert B to a lower alkoxy group in the same manner as in the above-mentioned alkoxylating reaction in route 5 and then to subject the product to the subsequent reaction.

From the reaction routes discussed in detail hereinbefore, it will be clear that there can easily be obtained the present compounds represented by the formula [I] and salts thereof, the intermediates which are the compounds represented by the formulas [IIIb], [IV] and [V] and their salts, and other novel intermediates.

This invention will be explained below in more detail referring to Referential Examples, Examples and Preparation Examples, which are not by way of limitation and merely by way of illustration.

REFERENTIAL EXAMPLE 1

(1) In 15 ml of anhydrous acetonitrile was suspended 2.72 g of 7-aminocephalosporanic acid (hereinafter, simply referred to as 7-ACA), and to the resulting suspension was added 5.68 g of boron trifluoridediethyl ether complex to form a solution, after which the solution was subjected to reaction at room temperature for 5 hours. After completion of the reaction, the solvent was removed by distillation under reduced pressure, and the residue obtained was dissolved in 20 ml of aqueous acetone (containing 50% by volume of water) and the pH thereof was adjusted to 3.5 with 28% by weight aqueous ammonia with ice-cooling. The deposited crystals were collected by filtration, washed successively with 5 ml of aqueous acetone containing 50% by volume of water and 5 ml of acetone, and then dried, to obtain 2.14 g (yield 79%) of 7-amino-3-acetamidomethyl-$\Delta^3$-cephem-4-carboxylic acid having a melting point of 155° C. (decomp.).

IR(KBr) cm$^{-1}$: $\nu_{C=O}$ 1795, 1640, 1610, 1520.
NMR(CF$_3$COOD) ppm value: 2.37 (3H, s, —CH$_3$), 3.82 (2H, s, C$_2$-H), 4.60

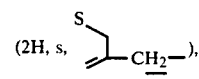

(2H, s,  —CH$_2$—), 5.41 (2H, bs, C$_6$-H, C$_7$-H).

(2) In 30 ml of methanol was suspended 2.71 g of 7-amino-3-acetamidomethyl-$\Delta^3$-cephem-4-carboxylic acid obtained in above (1), to which suspension 1.90 g of p-toluenesulfonic acid monohydrate was added to form a solution. Then, 4 g of diphenyldiazomethane was slowly added to the solution at room temperature and the resulting mixture was subjected to reaction at that temperature for 30 minutes. After completion of the reaction, the solvent was removed by distillation under reduced pressure, and the residue thus obtained was dissolved in a mixed solvent of 20 ml of water and ml of ethyl acetate, and the pH of the solution was adjusted to 7.0 with sodium hydrogen carbonate. The deposited crystals were collected by filtration, thoroughly washed with water and dried, to obtain 2.84 g (yield 65%) of diphenylmethyl 7-amino-3-acetamidomethyl-$\Delta^3$-cephem-4-carboxylate having a melting point of 190°-194° C. (decomp.).

IR(KBr) cm$^{-1}$: $\nu_{C=O}$ 1758, 1720, 1647.
NMR(CDCl$_3$) ppm value: 1.87 (3H s, —CH$_3$), 3.59 (2H, s, C$_2$-H), 3.65, 4.27

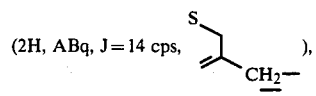

(2H, ABq, J=14 cps,  —CH$_2$—), 4.71 (1H, d, J=5 Hz, C$_6$-H), 4.89 (1H, d, J=5 Hz, C$_7$-H), 6.12 (1H, bs, —NHCO—), 6.90 (1H, s, —COOH<),

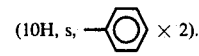

(10H, s, —⌬ × 2).

REFERENTIAL EXAMPLE 2

Reaction and treatments were carried out in the same manner as in Referential Example 1-(1), except that trifluoroacetic acid was used as the reaction solvent. Thus, the products shown in Table 4 were obtained.

TABLE 4

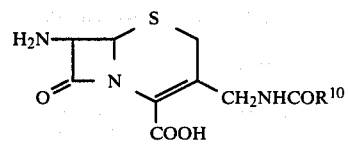

| Starting compound | Acid or acid complex | Product R$^{10}$ | Melting point (°C.) | IR(KBr) cm$^{-1}$: $\nu_{C=O}$ |
|---|---|---|---|---|
| Butyronitrile | *BF$_3$.Et$_2$O | —CH$_2$CH$_2$CH$_3$ | 168-170 (decomp.) | 1795, 1635, 1610, 1520 |
| 2-Methylbutyronitrile | " | —CHCH$_2$CH$_3$ with CH$_3$ | 170-172 (decomp.) | 1795, 1635, 1620, 1530 |
| 3-Ethoxypropionitrile | " | —CH$_2$CH$_2$OCH$_2$CH$_3$ | 173-175 | 1800, 1640, |

TABLE 4-continued

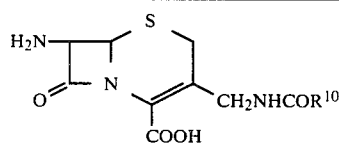

| Starting compound | Acid or acid complex | Product R[10] | Melting point (°C.) | IR(KBr) cm$^{-1}$: $\nu_{C=O}$ |
|---|---|---|---|---|
| Acrylonitrile | " | —CH=CH$_2$ | 165–167 (decomp.) | 1610, 1530 1800, 1650, 1615, 1525 |
| Cyanoacetic acid | " | —CH$_2$COOH | 192–195 (decomp.) | 1755, 1675, 1620, 1580 |
| Benzyl cyanide | " | —CH$_2$—C$_6$H$_5$ | 185–190 (decomp.) | 1795, 1635, 1620, 1520 |
| Ethyl cyanoacetate | " | —CH$_2$COOCH$_2$CH$_3$ | 185–190 (decomp.) | 1785, 1730, 1610, 1530 |
| Chloroacetonitrile | " | —CH$_2$Cl | 185–190 (decomp.) | 1790, 1650, 1610, 1520 |
| 2-Cyanofuran | " | 2-furyl | 200–204 (decomp.) | 1780, 1630, 1590, 1510 |
| Benzonitrile | " | phenyl | 212–214 (decomp.) | 1793, 1630, 1610, 1520 |
| 2-Cyanothiophene | " | 2-thienyl | 189–190 (decomp.) | 1795, 1620, 1530 |
| p-Tolunitrile | " | 4-CH$_3$-C$_6$H$_4$— | 173–178 (decomp.) | 1790, 1630, 1615, 1530 |
| p-Anisonitrile | " | 4-CH$_3$O-C$_6$H$_4$— | 188–193 (decomp.) | 1790, 1620, 1595, 1530 |
| p-Hydroxybenzonitrile | " | 4-HO-C$_6$H$_4$— | 182–184 (decomp.) | 1795, 1625, 1600, 1530 |
| p-Cyanobenzoic acid | " | 4-HOOC-C$_6$H$_4$— | 178–183 (decomp.) | 1800, 1700, 1630, 1530 |
| 2-Cyano-5-methylfuran | " | 5-methyl-2-furyl | 188–190 (decomp.) | 1780, 1630, 1600, 1530 |
| 2-Cyano-3-methylthiophene | " | 3-methyl-2-thienyl | 175–178 (decomp.) | 1790, 1630, 1610, 1530 |

TABLE 4-continued

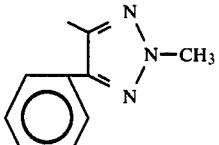

| Starting compound | Acid or acid complex | Product R¹⁰ | Melting point (°C.) | IR(KBr) cm⁻¹: $\nu_{C=O}$ |
|---|---|---|---|---|
| 2-Methyl-4-cyano-5-phenyl-1,2,3-triazole | " | 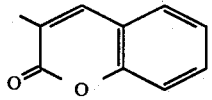 | 193–195 (decomp.) | 1790, 1660, 1610, 1530 |
| 3-Cyanocoumarin | " | 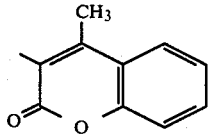 | 197–199 (decomp.) | 1790, 1710, 1640, 1600, 1530 |
| 3-Cyano-4-methylcoumarin | " | 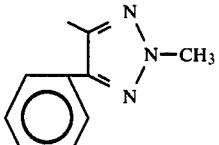 -CH₃ | 210–212 (decomp.) | 1790, 1710, 1640, 1600, 1530 |
| **Acetonitrile | Conc. sulfuric acid | —CH₃ | 155 (decomp.) | 1795, 1640, 1610, 1520 |

Note:
*BF₃·Et₂O means boron trifluoride-diethyl ether complex (hereinafter the same applies).
**The reaction was carried out in acetonitrile.

REFERENTIAL EXAMPLE 3

Reaction and treatments were carried out in the same manner as in Referential Example 1-(2) to obtain the compounds shown in Table 5.

TABLE 5

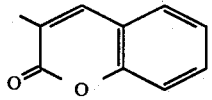

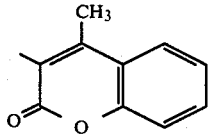

| Compound R¹⁰ | Melting point (°C.) | IR(KBr) cm⁻¹: $\nu_{C=O}$ |
|---|---|---|
|  (furan) | 167–169 (decomp.) | 1755, 1718, 1642 |
| (thiophene) | 192–195 (decomp.) | 1755, 1720, 1625 |

TABLE 5-continued

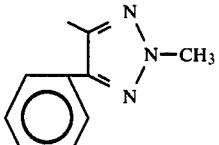

| Compound R¹⁰ | Melting point (°C.) | IR(KBr) cm⁻¹: $\nu_{C=O}$ |
|---|---|---|
| (phenyl) | 218–220 (decom.) | 1755, 1720, 1638 |

EXAMPLE 1

(1) In 13 ml of sulfolane was suspended 2.72 g of 7-ACA, and 14.2 g of boron trifluoride-diethyl ether complex and 1.0 g of 5-methyl-1,2,3,4-tetrazole were added to the resulting suspension, after which the resulting mixture was subjected to reaction at room temperature for 17 hours. After completion of the reaction, the reaction mixture was thrown into 15 ml of ice water. The pH of the mixture was adjusted to 3.5 with 28% by weight aqueous ammonia with ice-cooling. The deposited crystals were collected by filtration, washed successively with 5 ml of water and 5 ml of acetone and then dried, to obtain 1.76 g of a mixture of 7-amino-3-[2-(5-methyl-1,2,3,4-tetrazolyl)methyl]-Δ³-cephem-4-carboxylic acid and 7-amino-3-[1-(5-methyl-1,2,3,4-tetrazolyl)methyl]-Δ³-cephem-4-carboxylic acid in the form of crystals.

(2) In 18 ml of methanol was suspended 1.76 g of the crystals obtained in above (1), and 1.13 g of p-toluenesulfonic acid monohydrate was added to the suspension to form a solution, after which 4.6 g of diphenyldiazomethane was slowly added thereto. The resulting mixture was subjected to reaction at room temperature for 15 minutes. After completion of the reaction, the solcent was removed by distillation under reduced pressure. The residue thus obtained was dissolved in a mixed solvent of 30 ml of ethyl acetate and 30 ml of water, and the pH of the resulting solution was adjusted to 8 with sodium hydrogen carbonate. Then, the organic layer was separated and dried on anhydrous magnesium sulfate, and the solvent was removed by distillation under reduced pressure. The residue thus obtained was purified by column chromatography (Wako silica gel C-200; developing solvent, benzene:ethyl acetate=4:1 by volume) to obtain 0.79 g of diphenylmethyl 7-amino-3-[2-(5-methyl-1,2,3,4-tetrazolyl)methyl]-Δ³-cephem-4-carboxylate having a melting point of 157°-160° C. (decomp.) and 0.14 g of diphenylmethyl 7-amino-3-[1-(5-methyl-1,2,3,4-tetrazolyl)methyl]-Δ³-cephem-4-carboxylate having a melting point of 92° C. (decomp.)

Diphenylmethyl 7-amino-3-]2-(5-methyl-1,2,3,4-tetrazolyl)methyl]-Δ³-cephem-4-carboxylate:
IR(KBr) cm⁻¹: $\nu_{C=O}$ 1770, 1720.
NMR(CDCl₃) ppm value: 1.75 (2H, bs, —NH₂), 2.48 (3H, s, —CH₃), 3.20 (2H, s, C₂-H), 4.70 (1H, d, J=5 Hz, C₆-H), 4.87 (1H, d, J=5 Hz, C₇-H), 5.30, 5.72

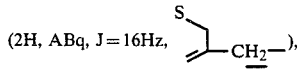(2H, ABq, J=16Hz), 6.92 (1H, s, —CH<), 7.30

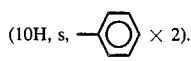(10H, s, ×2).

Diphenylmethyl 7-amino-3-[1-(5-methyl-1,2,3,4-tetrazolyl)methyl]-Δ³-cephem-4-carboxylate:
IR(KBr) cm⁻¹: $\nu_{C=O}$ 1770, 1725.
NMR(CDCl₃) ppm value: 1.80 (2H, s, —NH₂), 2.15 (3H, s, —CH₃), 3.30 (2H, s, C₂-H), 4.70 (1H, d, J=5 Hz, C₆-H), 4.85 (1H, d, J=5 Hz, C₇-H), 5.00, 5.38

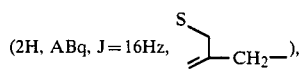(2H, ABq, J=16Hz), 6.90 (1H, s, —CH<), 7.30

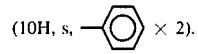(10H, s, ×2).

(3) In a mixed solvent of 0.5 ml of anisole and 5 ml of trifluoroacetic acid was dissolved 0.462 g of diphenylmethyl 7-amino-3-[2-(5-methyl-1,2,3,4-tetrazolyl)methyl]-Δ³-cephem-4-carboxylate, and the resulting solution was subjected to reaction at room temperature for 1 hour. After completion of the reaction, the solvent was removed by distillation under reduced pressure, and 10 ml of water and 10 ml of ethyl acetate were added to the residue obtained. The pH thereof was adjusted to 8 with 28% by weight aqueous ammonia with ice-cooling. Then, the aqueous layer was separated and the pH thereof was adjusted to 3.5 with 2N hydrochloric acid with ice-cooling. The deposited crystals were collected by filtration, washed successively with 5 ml of water and 5 ml of acetone, and then dried, to obtain 0.26 g of 7-amino-3-[2-(5-methyl-1,2,3,4-tetrazolyl)methyl]-Δ³-cephem-4-carboxylic acid having a melting point of 178° C. (decomp.)
IR(KBr) cm⁻¹: $\nu_{C=O}$ 1790, 1610, 1530.
NMR(CF₃COOD) ppm value: 2.70 (3H, s, —CH₃), 3.73 (2H, s, C₂-H), 5.40 (2H, s, C₆-H, C₇-H), 5.80, 6.12

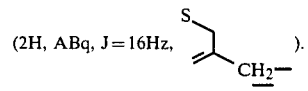(2H, ABq, J=16Hz).

In the same manner as above, from 0.462 g of diphenylmethyl 7-amino-3-[1-(5-methyl-1,2,3,4-tetrazoyl)methyl]-Δ³-cephem-4-carboxylate was obtained 0.25 g of 7-amino-3-[1-(5-methyl-1,2,3,4-tetrazolyl)methyl]-Δ³-cephem-4-carboxylic acid having a melting point of 195° C. (decomp.).
IR(KBr) cm⁻¹: $\nu_{C=O}$ 1795, 1615, 1530.
NMR(CF₃COOD) ppm value: 2.95 (3H, s, —CH₃), 3.90 (2H, bs, C₂-H), 5.45 (2H, s, C₆-H, C₇-H), 5.57, 5.92

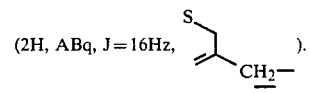(2H, ABq, J=16Hz).

EXAMPLE 2

In 19 ml of trifluoroacetic acid was dissolved 2.72 g of 7-ACA, and 7.1 g of boron trifluoride-diethyl ether complex and 0.75 g of 1,2,4-triazole are added to the resulting solutoin. The resulting mixture was subjected to reaction at rroom temperature for 7 hours. After completion of the reaction, the solvent was removed by distillation under reduced pressure, and 15 ml of water was added to the resulting residue, and the pH of the resulting mixture was adjusted to 3.5 with 28% by weight aqueous ammonia with ice-cooling. The deposited crystals were collected by filtration, washed successively with 5 ml of water and 5 ml of acetone and then dried, to obtain 2.5 g of 7-amino-3-[1-(1,2,4-triazolyl)methyl]-Δ³-cephem-4-carboxylic acid having a melting point of 149° C. (decomp.).
IR(KBr) cm⁻¹: $\nu_{C=O}$ 1790, 1610, 1530.

NMR(CF₃COOD) ppm value: 4.00 (2H, bs, C₂-H), 5.47

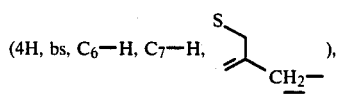
(4H, bs, C₆—H, C₇—H, )

8.70

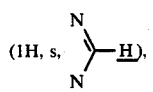
(1H, s, —H), 9.80

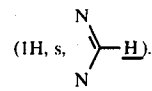
(1H, s, —H).

EXAMPLE 3

Using the following tetrazoles, reaction and treatments were carried out in the same manner as in Example 1-(1) or Example 2 to obtain the results shown in Table 6. Subsequently, the products of Table 6 were esterified and thereafter de-esterified in the same manner as in Example 1-(2) and (3) to obtain the esters and carboxylic acids shown in Table 7.

TABLE 6

| 7-ACA (g) | Starting compound R | (g) | BF₃·Et₂O (g) | Reaction solvent (ml) | Reaction temp. (°C.) | Reaction time (hr) | Yield (g) | Crude product R² |
|---|---|---|---|---|---|---|---|---|
| 2.72 | —CH₂COOCH₂CH₃ | 1.72 | 7.1 | CF₃COOH 19 | Room temp. | 7 | 0.8 | CH₂COOCH₂CH₃ |
| 2.72 | —C₆H₅ (phenyl) | 1.6 | 7.1 | CF₃COOH 19 | Room temp. | 7 | 0.85 | phenyl |
| 2.72 | —H | 0.77 | 7.1 | Sulfolane 13 | Room temp. | 7 | 1.4* | (two tetrazole isomers) |
| 2.72 | —Br | 1.65 | 7.1 | CF₃COOH 19 | Room temp. | 7 | 2.2* | Br, Br |
| 2.72 | —SCH₃ | 1.3 | 7.1 | CF₃COOH 19 | Room temp. | 7 | 2.0* | SCH₃, SCH₃ |
| 2.72 | —NH₂ | 0.94 | 7.1 | CF₃COOH 19 | Room temp. | 7 | 1.3 | NH₂ |

TABLE 6-continued

| 7-ACA (g) | Starting compound R (N—N, R-C=N-NH, tetrazole) | (g) | BF₃·Et₂O (g) | Reaction solvent (ml) | Reaction temp. (°C.) | Reaction time (hr) | Yield (g) | Crude product R² |
|---|---|---|---|---|---|---|---|---|
| 2.72 | —CH₂CH₃ | 1.08 | 14.2 | Sulfolane 13 | 50 | 7 | 1.36* | (mixture of tetrazolyl isomers with CH₂CH₃) |
| 2.72 | —COOCH₂CH₃ | 1.56 | 7.1 | Sulfolane 13 | 50 | 7 | 2.86* | (mixture of tetrazolyl isomers with COOCH₂CH₃) |
| 2.72 | —NHCOCH₃ | 1.4 | 7.1 | CF₃COOH 19 | Room temp. | 7 | 1.0 | (tetrazolyl with NHCOCH₃) |

Note:
*These were obtained in the form of a mixture of 1-substituted and 2-substituted products. Such crude products were reacted and treated in the same manner as in Example 1-(2) to isolate the esters of the respective 1-substituted and 2-substituted products. The properties of these compounds are shown in Table 7.

TABLE 7

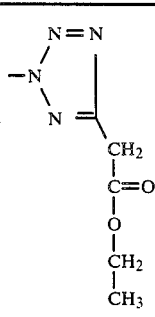

| —R² | Melting point (°C.) | IR(KBr) cm⁻¹: $\nu_{C=O}$ | NMR(CDCl₃) ppm value: | Melting point (°C.) | IR(KBr) cm⁻¹: $\nu_{C=O}$ | NMR(CF₃COOD) ppm value: |
|---|---|---|---|---|---|---|
| tetrazolyl-CH₂-C(=O)-O-CH₂-CH₃ | 107–110 (decomp.) | 1770, 1725 | 1.20 (3H, t, —CH₂CH₃), 1.88 (2H, bs, —NH₂), 3.14 (2H, s, C₂—H), 3.85 (2H, s, —CH₂COO—), 4.10 (2H, q, —CH₂CH₃), 4.55 (1H, d, J=5Hz, C₆—H), 4.75 (1H, d, J=5Hz, C₇—H), 5.27, 5.68 (2H, ABq, J=16Hz, S-CH₂-), 6.90 (1H, | 177 (decomp.) | 1795, 1735, 1610, 1535 | 1.35 (3H, t, —CH₂CH₃), 3.67 (2H, bs, C₂—H̄), 4.20 (2H, s, —CH₂COO—), 4.35 (2H, q, —CH₂CH₃), 5.40 (2H, s, C̄₆—H, C₇—H), 5.96 (2H, bs, S-CH₂-) |

TABLE 7-continued

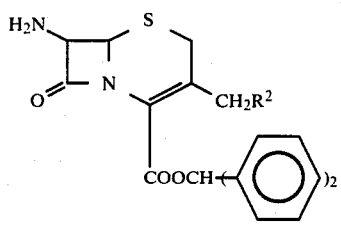 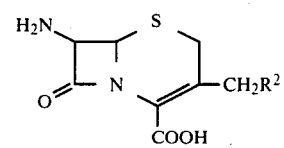

| $-R^2$ | Melting point (°C.) | IR(KBr) cm$^{-1}$: $\nu_{C=O}$ | NMR(CDCl$_3$) ppm value: | Melting point (°C.) | IR(KBr) cm$^{-1}$: $\nu_{C=O}$ | NMR(CF$_3$COOD) ppm value: |
|---|---|---|---|---|---|---|
| | | | s, —CH ), 7.23 (10H, s, —⌬ × 2) | | | |
| —N(N=N)N—C₆H₅ (tetrazolyl-phenyl) | 73–75 (decomp.) | 1770, 1725 | 1.80 (2H, bs, —NH$_2$), 3.22 (2H, s, C$_2$—H), 4.65 (1H, d, J=5Hz, C$_6$—H), 4.85 (1H, d, J=5Hz, C$_7$—H), 5.35, 5.80 (2H, ABq, J=16Hz, S—CH$_2$—), 6.90 (1H, s, —CH ), 7.23 (15Hz, s, —⌬ × 3) | 171 (decomp.) | 1790, 1610, 1530 | 3.75 (2H, s, C$_2$—H), 5.38 (2H, s, C$_6$—H, C$_7$—H), 6.02 (2H, bs, S—CH$_2$—), 7.40–7.65 (3H, m, arom. H), 7.85–8.10 (2H, m, arom. H) |
| —N(N=N)N—CH (tetrazolyl) | 79–83 (decomp.) | 1770, 1720 | 1.85 (2H, s, —NH$_2$), 3.12 (2H, s, C$_2$—H), 4.60 (1H, d, J=5Hz, C$_6$—H), 4.80 (1H, d, J=5Hz, C$_7$—H), 5.37, 5.80 (2H, ABq, J=16Hz, S—CH$_2$—), 6.97 (1H, s, —CH ), 7.30 (10H, s, —⌬ × 2), 8.43 (1H, s, N=CH—N tetrazolyl H) | 220 (decomp.) | 1800, 1610, 1530 | 3.70 (2H, bs, C$_2$—H), 5.40 (2H, s, C$_6$—H, C$_7$—H), 6.03 (2H, bs, S—CH$_2$—), 8.80 (1H, s, tetrazolyl H) |
| —N(N=N)N—CBr (bromotetrazolyl) | 75–78 (decomp.) | 1770, 1720 | 1.87 (2H, s, —NH$_2$), 3.24 (2H, s, C$_2$—H), 4.68 (1H, d, J=5Hz, C$_6$—H), 4.87 (1H, d, J=5Hz, C$_7$—H), 5.30, 5.77 (2H, ABq, | 165 (decomp.) | 1790, 1610, 1530 | 3.60 (2H, bs, C$_2$—H), 5.40 (2H, s, C$_6$—H, C$_7$—H), 5.94 (2H, bs, S—CH$_2$—) |

TABLE 7-continued

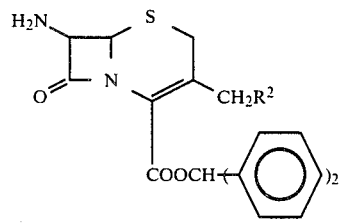
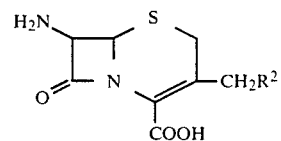

| —R² | Melting point (°C.) | IR(KBr) cm⁻¹: $\nu_{C=O}$ | NMR(CDCl₃) ppm value: | Melting point (°C.) | IR(KBr) cm⁻¹: $\nu_{C=O}$ | NMR(CF₃COOD) ppm value: |
|---|---|---|---|---|---|---|
| | | | J=16Hz, $\underset{CH_2-}{\overset{S}{\diagup}}$ ), 6.92 (1H, s, —CH< ), 7.27 (10H, s, —⌬ × 2) | | | |
| 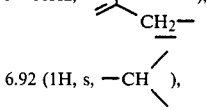 | 96–98 (decomp.) | 1770, 1720 | 1.85 (2H, s, —NH₂), 3.20 (2H, s, C₂—H), 4.75 (1H, d, J=5Hz, C₆—H), 4.88 (1H, d, J=5Hz, C₇—H), 5.03, 5.67 (2H, ABq, J=16Hz, $\underset{CH_2-}{\overset{S}{\diagup}}$ ), 6.98 (1H, s, —CH< ), 7.30 (10H, s, —⌬ × 2) | — | — | — |
| 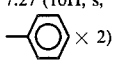 | 64–68 (decomp.) | 1770, 1720 | 1.95 (2H, bs, —NH₂), 2.58 (3H, s, —SCH₃), 3.18 (2H, s, C₂—H), 4.60 (1H, d, J=5Hz, C₆—H), 4.80 (1H, d, J=5Hz, C₇—H), 5.25, 5.72 (2H, ABq, J=16Hz, $\underset{CH_2-}{\overset{S}{\diagup}}$ ), 6.90 (1H, s, —CH< ), 7.25 (10H, s, —⌬ × 2) | 195 (decomp.) | 1790, 1610, 1530 | 2.68 (3H, s, —SCH₃), 3.62 (2H, s, C₂—H), 5.28 (2H, s, C₆—H, C₇—H), 5.80 (2H, s, $\underset{CH_2-}{\overset{S}{\diagup}}$ ) |
| 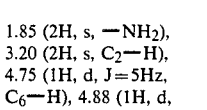 | 158–162 (decomp.) | 1760, 1710 | 1.75 (2H, bs, —NH₂), 2.58 (3H, s, —SCH₃), 3.10 (2H, s, C₂—H), 4.60 (1H, d, J=5Hz, C₆—H), 4.80 (1H, d, J=5Hz, C₇—H), 4.97, 5.47 (2H, ABq, | 174 (decomp.) | 1795, 1610, 1530 | 2.87 (3H, s, —SCH₃), 3.63 (2H, s, C₂—H), 5.35 (2H, s, C₆—H, C₇—H), 5.60 (2H, s, $\underset{CH_2-}{\overset{S}{\diagup}}$ ) |

TABLE 7-continued

Structure (left): H$_2$N-β-lactam-S with CH$_2$R$^2$ substituent, COOCH(C$_6$H$_5$)$_2$ ester Structure (right): H$_2$N-β-lactam-S with CH$_2$R$^2$ substituent, COOH

| —R$^2$ | Melting point (°C.) | IR(KBr) cm$^{-1}$: $\nu_{C=O}$ | NMR(CDCl$_3$) ppm value: | Melting point (°C.) | IR(KBr) cm$^{-1}$: $\nu_{C=O}$ | NMR(CF$_3$COOD) ppm value: |
|---|---|---|---|---|---|---|
| | | | J=16Hz, (S-CH$_2$-C=CH$_2$-) 6.93 (1H, s, —CH), 7.25 (10H, s, —C$_6$H$_5$ × 2) | | | |
| tetrazolyl-NH$_2$ | 115 (decomp.) | 1770, 1720 | *3.10 (2H, bs, —NH$_2$), 3.43 (2H, s, C$_2$—H), 4.85 (1H, d, J=5Hz, C$_6$—H), 5.05 (1H, d, J=5Hz, C$_7$—H), 5.30 (2H, s, S-CH$_2$-C=CH$_2$-), 6.06 (2H, bs, N=C-NH$_2$), 6.90 (1H, s, —CH), 7.35 (10H, s, —C$_6$H$_5$ × 2) | 195 (decomp.) | 1795, 1615, 1530 | 3.75 (2H, bs, C$_2$—H), 5.35 (2H, s, C$_6$—H, C$_7$—H), 5.80 (2H, bs, S-CH$_2$-) |
| tetrazolyl-CH$_2$CH$_3$ | 142-143 (decomp.) | 1775, 1725 | 1.32 (3H, t, —CH$_2$CH$_3$), 1.75 (2H, bs, —NH$_2$), 2.85 (2H, q, —CH$_2$CH$_3$), 3.17 (2H, s, C$_2$—H), 4.67 (1H, d, J=5Hz, C$_6$—H), 4.82 (1H, d, J=5Hz, C$_7$—H), 5.27, 5.70 (2H, ABq, J=16Hz, S-CH$_2$-), 6.93 (1H, s, —CH), 7.30 (10H, s, —C$_6$H$_5$ × 2) | 198-202 (decomp.) | 1795, 1615, 1530 | 1.48 (3H, t, —CH$_2$CH$_3$), 3.10 (2H, q, —CH$_2$CH$_3$), 3.75 (2H, s, C$_2$—H), 5.40 (2H, s, C$_6$—H, C$_7$—H), 5.85, 6.10 (2H, ABq, S-CH$_2$-) |
| triazolyl-CH$_2$CH$_3$ | 82-83 (decomp.) | 1770, 1720 | 1.20 (3H, t, —CH$_2$CH$_3$), 1.90 (2H, bs, —NH$_2$), 2.50 (2H, q, —CH$_2$CH$_3$), 3.25 (2H, s, C$_2$—H), 4.70 (1H, d, J=5Hz, C$_6$—H), 4.90 (1H, d, J=5Hz, C$_7$—H), 5.02, 5.40 (2H, ABq, J=16Hz, | 195-197 (decomp.) | 1795, 1610, 1530 | 1.57 (3H, t, —CH$_2$CH$_3$), 3.30 (2H, q, —CH$_2$CH$_3$), 3.83 (2H, s, C$_2$—H), 5.40 (2H, s, C$_6$—H, C$_7$—H), 5.53, 5.92 (2H, ABq, J=16Hz, S-CH$_2$-) |

TABLE 7-continued

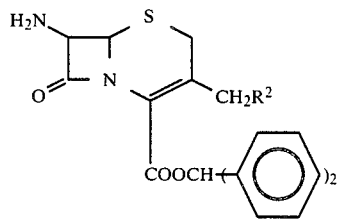 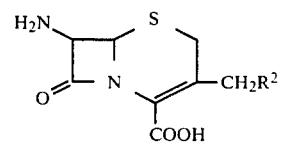

| -R² | Melting point (°C.) | IR(KBr) cm⁻¹: ν$_{C=O}$ | NMR(CDCl₃) ppm value: | Melting point (°C.) | IR(KBr) cm⁻¹: ν$_{C=O}$ | NMR(CF₃COOD) ppm value: |
|---|---|---|---|---|---|---|
| | | | ), 6.90 (1H, s, —CH<), 7.28 (10H, s, —⌬ × 2) | | | |
| 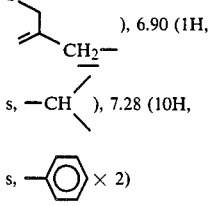 | 165–167 (decomp.) | 1775, 1735, 1710 | 1.38 (3H, t, —CH₂CH₃), 1.72 (2H, s, —NH₂), 3.25 (2H, bs, C₂—H), 4.32 (2H, q, —CH₂CH₃), 4.70 (1H, d, J=5Hz, C₆—H), 4.82 (1H, d, J=5Hz, C₇—H), 5.40, 5.90 (2H, ABq, J=16Hz, <br> ), 6.90 (1H, s, —CH<), 7.30 (10H, s, —⌬ × 2) | 158 (decomp.) | 1800, 1735, 1610, 1530 | 1.50 (3H, t, —CH₂CH₃), 3.55, 3.90 (2H, ABq, J=18Hz, C₂—H), 4.60 (2H, q, —CH₂CH₃), 5.40 (2H, s, C₆—H, C₇—H), 6.05 (2H, bs, <br> ) |
| 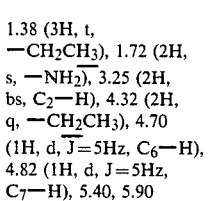 | 140–142 (decomp.) | 1770, 1735, 1720 | 1.42 (3H, t, —CH₂CH₃), 1.80 (2H, s, —NH₂), 3.20 (2H, s, C₂—H), 4.45 (2H, q, —CH₂CH₃), 4.70 (1H, d, J=5Hz, C₆—H), 4.85 (1H, d, J=5Hz, C₇—H), 5.35, 5.90 (2H, ABq, J=16Hz, <br> ), 6.90 (1H, s, —CH<), 7.30 (10H, s, —⌬ × 2) | 142 (decomp.) | 1800, 1740, 1610, 1530 | 1.50 (3H, t, —CH₂CH₃), 3.70 (2H, bs, C₂—H), 4.55 (2H, q, —CH₂CH₃), 5.40 (2H, s, C₆—H, C₇—H), 6.02 (2H, bs, <br> ) |

TABLE 7-continued

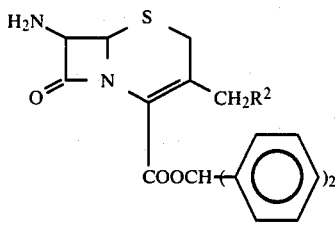 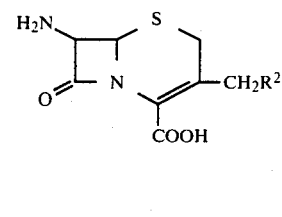

| —R² | Melting point (°C.) | IR(KBr) cm⁻¹: $\nu_{C=O}$ | NMR(CDCl₃) ppm value: | Melting point (°C.) | IR(KBr) cm⁻¹: $\nu_{C=O}$ | NMR(CF₃COOD) ppm value: |
|---|---|---|---|---|---|---|
| ![structure with N=N, -N, NH, C=O, CH₃] | 106–108 (decomp.) | 1770, 1720, 1700 | 1.95 (2H, bs, —NH₂), 2.20 (3H, s, —COCH₃), 3.20 (2H, bs, C₂—H), 4.67 (1H, d, J=5Hz, C₆—H), 4.82 (1H, d, J=5Hz, C₇—H), 5.32, 5.68 (2H, ABq, J=16Hz, [S/CH₂ structure]), 6.90 (1H, s, —CH[ph]), 7.25 (10H, s, —⌬ × 2), 9.75 (1H, bs, \NH/) | 179 (decomp.) | 1790, 1690, 1610, 1530 | 2.42 (3H, s, —CH₃), 3.70 (2H, s, C₂—H), 5.40 (2H, s, C₆—H, C₇—H), 5.94 (2H, bs, [S/CH₂ structure]) |
| ![structure with N=N, -N, N triazole] | 147–150 (decomp.) | 1770, 1720 | *3.30 (2H, bs, —NH₂), 3.47 (2H, bs, C₂—H), 4.87 (1H, d, J=5Hz, C₆—H), 5.04 (1H, d, J=5Hz, C₇—H), 5.35 (2H, bs, [S/CH₂ structure]), 6.91 (1H, s, \CH—/), 7.34 (10H, s, —⌬ × 2), 9.22 (1H, s, [N/N—H triazole]) | — | — | — |

Note:
*Solvent for measurement, d₆-DMSO

EXAMPLE 4

Using the following triazoles, reaction and treatments were carried out in the same manner as in Example 1-(1) or Example 2 to obtain the compounds shown in Table 8. The carboxylic acids were esterified in the same manner as in Example 1-(2) to obtain the compounds shown in Table 9. (2.72 g of 7-ACA was used as the starting material.)

TABLE 8

$$\text{H}_2\text{N} \underset{\text{O}}{\overset{\text{S}}{\square}} \underset{\text{COOH}}{\overset{\text{CH}_2\text{R}^2}{}}$$

| Starting triazole (g) | Compound (g) R² | Melting point (°C.) | IR(KBr) cm⁻¹: $\nu_{C=O}$ | NMR ( * CF₃COOD / ** CF₃COOD + D₂O ) ppm value |
|---|---|---|---|---|
| 3-Methyl-1,2,4-triazole 0.91 | (N—N, O, N, CH₃) 2.39 | 195 (decomp.) | 1790, 1610, 1530 | ** 2.60 (3H, s, —CH₃), 3.93 (2H, s, C₂—H), 5.30 (2H, s, C₆—H, C₇—H), 5.10, 5.75 (2H, ABq, J=16Hz, S-CH₂—), 9.45 (1H, s, triazole-H) |
| 3-Chloro-1,2,4-triazole 1.14 | (N—N, O, N, Cl) 1.25 | 191 (decomp.) | 1790, 1610, 1530 | * 3.75 (2H, s, C₂—H), 5.40 (2H, s, C₆—H, C₇—H), 5.47, 5.80 (2H, ABq, J=16Hz, S-CH₂—), 8.50 (1H, s, triazole-H) |
| 3-Acetamido-1,2,4-triazole 2.52 | (N—N, O, N, NHCOCH₃) 2.6 | 150–155 (decomp.) | 1795, 1680, 1610, 1540 | * 2.43 (3H, s, —CH₃), 3.19 (2H, s, C₂—H), 5.35 (2H, s, C₆—H, C₇—H), 5.30–5.95 (2H, m, S-CH₂—), 9.45 (1H, s, triazole-H) |
| 3-Ethoxycarbonyl-1,2,4-triazole 1.55 | (N—N, O, N, COOCH₂CH₃) 2.3 | 176 (decomp.) | 1795, 1720, 1610, 1530 | ** 1.50 (3H, t, —CH₂CH₃), 3.72 (2H, bs, C₂—H), 4.65 (2H, q, —CH₂CH₃), 5.35 (2H, s, C₆—H, C₇—H), 5.95 (2H, bs, S-CH₂—), 8.65 (1H, s, triazole-H) |
| 3-Methylthio-1,2,4-triazole 1.3 | (N—N, O, N, SCH₃) 3.4 | 147 (decomp.) | 1770, 1605, 1530 | * 2.75 (3H, s, —SCH₃), 4.00 (2H, s, C₂—H), 5.40 (2H, s, C₆—H, C₇—H), 5.23, 5.85 (2H, ABq, J=16Hz, S-CH₂—), 9.55 (1H, s, triazole-H) |
| 4,5-Dimethoxycarbonyl-1,2,3-triazole 1.94 | (—N, N=N, COOCH₃, COOCH₃) 2.0 | 161 (decomp.) | 1795, 1725, 1610, 1530 | * 3.55 (2H, bs, C₂—H), 4.10 (6H, s, —CH₂ × 2), 5.35 (2H, s, S-CH₂—), 5.90 (2H, s, C₆—H, C₇—H) |

TABLE 8-continued

[Structure: β-lactam with H₂N-, S, N, CH₂R², COOH groups]

| Starting triazole (g) | Compound (g) R² | Melting point (°C.) | IR(KBr) cm⁻¹: $\nu_{C=O}$ | NMR $\left(\begin{array}{l}* CF_3COOD \\ ** CF_3COOD + D_2O\end{array}\right)$ ppm value |
|---|---|---|---|---|
| 4-Cyano-5-phenyl-1,2,3-triazole 1.9 | [triazole with CN and phenyl substituents] 1.3 | 204 (decomp.) | 2220, ($\nu_{CN}$) 1790, 1610, 1530 | * 3.75 (2H, s, C₂—H), 5.35 (2H, s, C₆—H, C₇—H), 5.85 (2H, bs, [S-CH₂-]), 7.40–7.70 (3H, m, [aromatic H]), 7.80–8.10 (2H, m, [aromatic H]) |

TABLE 9

[Reaction scheme: conversion of COOH to COOCH(phenyl)₂ ester]

| —R² | Melting point (°C.) | IR(KBr) cm⁻¹: $\nu_{C=O}$ | NMR(CDCl₃) ppm value: |
|---|---|---|---|
| [1,2,4-triazole ring] | 61–65 (decomp.) | 1775, 1720 | 2.00 (2H, s, —NH₂), 3.43 (2H, s, C₂—H), 4.70 (1H, d, J=5Hz, C₆—H), 4.88 (1H, d, J=5Hz, C₇—H), 5.00 (2H, s, [S-CH₂-]), 6.95 (1H, s, —CH<), 7.30 (10H, s, —(phenyl) × 2), 7.85 (1H, s, [N=CH-N] H), 8.07 (1H, s, [N=CH-N] H) |
| [oxadiazole with CH-Cl] | 79–82 (decomp.) | 1770, 1720 | 1.82 (2H, bs, —NH₂), 3.10 (2H, s, C₂—H), 4.55 (1H, d, J=5Hz, C₆—H), 4.72 (1H, d, J=5Hz, C₇—H), 4.70, 5.33 (2H, ABq, J=16Hz, [S-CH₂-]), 6.93 (1H, bs, —CH<), 7.30 (10H, s, —(phenyl) × 2), 7.70 (1H, s, [N=CH-N] H) |

TABLE 9-continued

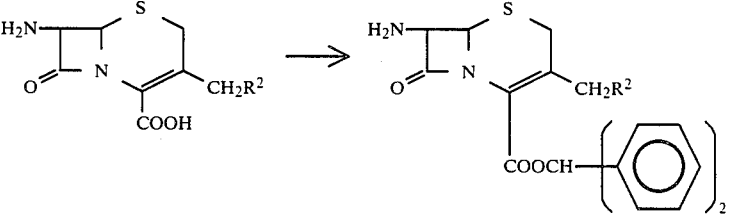

| —R² | Melting point (°C.) | IR(KBr) cm⁻¹: $\nu_{C=O}$ | NMR(CDCl₃) ppm value: |
|---|---|---|---|
| 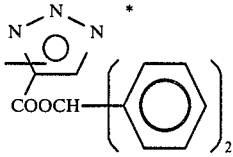 | 96–101 (decomp.) | 1770, 1720 | 2.33 (2H, bs, —NH₂), 2.78, 3.21 (2H, ABq, J=18Hz, C₂—H), 4.71 (1H, d, J=5Hz, C₆—H), 4.90 (1H, d, J=5Hz, C₇—H), 5.32, 5.92 (2H, ABq, J=16Hz, 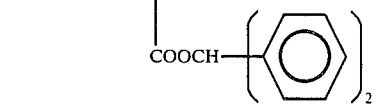), 6.86 (2H, s, —CH< × 2), 7.20 (20H, s, —⌬ × 4), 8.11 (1H, s, imidazole-H) |
| 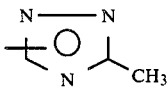 | 90 (decomp.) | 1770, 1720 | 2.32 (3H, s, —CH₃), 3.42 (2H, s, C₂—H), 4.70 (1H, d, J=5Hz, C₆—H), 4.85 (1H, d, J=5Hz, C₇—H), 4.90 (2H, s, 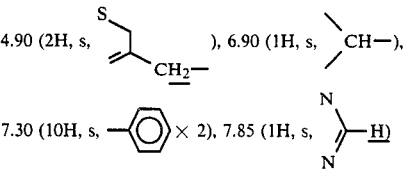), 6.90 (1H, s, >CH—), 7.30 (10H, s, —⌬ × 2), 7.85 (1H, s, imidazole-H) |
| 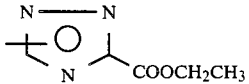 | 167–168 | 1770, 1720 | 1.35 (3H, t, —CH₂CH₃), 2.97, 3.30 (2H, ABq, J=18Hz, C₂—H), 4.30 (2H, q, —CH₂CH₃), 4.60 (1H, d, J=5Hz, C₆—H), 4.80 (1H, d, J=5Hz, C₇—H), 5.30, 5.80 (2H, ABq, J=16Hz, 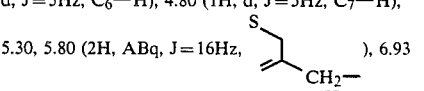), 6.93 (1H, s, >CH—), 7.30 (10H, s, —⌬ × 2), 7.88 (1H, s, imidazole-H) |
| 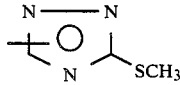 | 80–84 (decomp.) | 1770, 1720 | 1.90 (2H, bs, —NH₂), 2.50 (3H, s, —SCH₃), 3.40 (2H, s, C₂—H), 4.65 (1H, d, J=5Hz, C₆—H), 4.80 (1H, d, J=5Hz, C₇—H), 4.85 (2H, s, 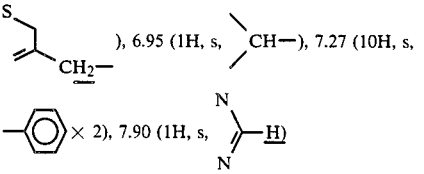), 6.95 (1H, s, >CH—), 7.27 (10H, s, —⌬ × 2), 7.90 (1H, s, imidazole-H) |

Note:
*This compound was obtained by subjecting 4-carboxy-1,2,3-triazole as the starting compound to reaction and treatment in the same manner as in Example 1-(1) and (2).

EXAMPLE 5

The same reaction as in Example 1 was carried out under the conditions shown in Table 10 to obtain the results shown in Table 10.

EXAMPLE 6

The same reaction as in Example 2 was carried out under the conditions shown in Table 11 to obtain the results shown in Table 11.

TABLE 10

| Starting compound | | Reaction conditions | | | | Crude product (g) | Esterification of crude product*[5] |
|---|---|---|---|---|---|---|---|
| 7-ACA (g) | 5-Methyl-tetrazole (g) | Acid or acid complex (g) | Reaction solvent (ml) | Reaction temp. (°C.) | Reaction time (hr) | | Ester of (a)*[1] (g) / Ester of (b)*[2] (g) |
| 2.72 | 1.0 | $BF_3.Et_2O$ 7.1 | Sulfolane 13 | 50 | 4 | 1.9*[3] | 0.3/0.7 |
| " | " | $BF_3.Et_2O$ 14.2 | Ethyl acetate 27 | Room temp. | 20 | 2.1*[3] | 0.95/0.15 |
| " | " | $BF_3.Et_2O$ 14.2 | Nitromethane 27 | Room temp. | 20 | 1.5*[3] | 0.63/0.1 |
| " | 0.92 | $BF_3.Et_2O$ 7.1 | Trifluoroacetic acid 19 | Room temp. | 7 | 1.5*[3] | 0.71/0.05 |
| " | 1.0 | Conc. $H_2SO_4$ 2.5 | Acetic acid 27 | 60 | 4 | 0.4*[3] | 0.1/0.03 |
| " | 1.26 | $BF_3$ 3.39 | Ethyl chloroacetate 15 | Room temp. | 16 | 1.44*[4] | — |
| " | 2.52 | $BF_3$ 6.78 | Ethyl chloroacetate 30 | Room temp. | 16 | 1.28*[4] | — |

Note:
*[1](a): 7-Amino-3-[2-(5-methyl-1,2,3,4-tetrazolyl)methyl]-$\Delta^3$-cephem-4-carboxylic acid
*[2](b): 7-Amino-3-[1-(5-methyl-1,2,3,4-tetrazolyl)methyl]-$\Delta^3$-cephem-4-carboxylic acid
*[3]The crude product was a mixture of (a) and (b).
*[4]The crude product was composed only of (a).
*[5]The crude product obtained by the reaction was subjected to reaction and treatment in the same manner as in Example 1-(2) to obtain the benzhydryl ester of each of (a) and (b).

TABLE 11

| Starting compound | | Reaction conditions | | | | Product | | |
|---|---|---|---|---|---|---|---|---|
| 7-ACA (g) | 1,2,4-Triazole (g) | Acid or acid complex (g) | Reaction solvent (ml) | Reaction temp. (°C.) | Reaction time (hr) | Name of compound | Yield (g) | Melting point (°C.) |
| 2.72 | 0.75 | $BF_3.Et_2O$ 7.1 | $CH_3CN$ 20 | Room temp. | 7 | 7-Amino-3-[1-(1,2,4-triazolyl)methyl]-$\Delta^3$-cephem-4-carboxylic acid | 2.02 | 149 (decomp.) |
| " | " | $BF_3.Et_2O$ 7.1 | $CHCl_2COOH$ 8 | Room temp. | " | 7-Amino-3-[1-(1,2,4-triazolyl)methyl]-$\Delta^3$-cephem-4-carboxylic acid | 2.0 | 149 (decomp.) |
| " | " | Conc. $H_2SO_4$ 5 | $CHCl_2COOH$ 8 | Room temp. | " | 7-Amino-3-[1-(1,2,4-triazolyl)methyl]-$\Delta^3$-cephem-4-carboxylic acid | 0.34 | 149 (decomp.) |
| " | " | $CH_3SO_3H$ 9.6 | $CF_3COOH$ 19 | Room temp. | " | 7-Amino-3-[1-(1,2,4-triazolyl)methyl]-$\Delta^3$-cephem-4-carboxylic acid | 1.31 | 149 (decomp.) |
| " | " | $FSO_3H$ 8 | $CH_3COOH$ 25 | Room temp. | 24 | 7-Amino-3-[1-(1,2,4-triazolyl)methyl]-$\Delta^3$-cephem-4-carboxylic acid | 1.12 | 149 (decomp.) |
| " | " | $CF_3SO_3H$ 12 | $CH_3COOH$ 25 | Room temp. | " | 7-Amino-3-[1-(1,2,4-triazolyl)methyl]-$\Delta^3$-cephem-4-carboxylic acid | 1.05 | 149 (decomp.) |
| *2.88 | 0.76 | $BF_3.Et_2O$ 7.1 | $CF_3COOH$ 23 | Room temp. | 7 | 7-Amino-3-[1-(1,2,4-triazolyl)methyl]-$\Delta^3$-cephem-4-carboxylic acid | 1.77 | 149 (decomp.) |

Note:
*7-Amino-3-acetoxymethyl-$\Delta^3$-cephem-4-carboxylic acid-1-oxide was used as the starting material.

EXAMPLE 7

The same reaction and treatment as in Example 2 were repeated, except that 7-ACA was replaced by the starting compounds shown in Table 12, to obtain the products shown in Table 12.

TABLE 12

| Starting compound | Product | Melting point (°C.) | IR (KBr) cm$^{-1}$: $\nu_{C=O}$ |
|---|---|---|---|
| p-Nitrobenzyl 7-amino-3-acetoxymethyl-Δ$^3$-cephem-4-carboxylate | p-Nitrobenzyl 7-amino-3-[1-(1,2,4-triazolyl)methyl]-Δ$^3$-cephem-4-carboxylate | 114–116 (decomp.) | 1770, 1708 |
| Ethyl 7-amino-3-acetoxymethyl-Δ$^3$-cephem-4-carboxylate | Ethyl 7-amino-3-[1-(1,2,4-triazolyl)methyl]-Δ$^3$-cephem-4-carboxylate | 68–72 (decomp.) | 1770, 1720 |
| Diphenylmethyl 7-amino-3-acetoxymethyl-Δ$^3$-cephem-4-carboxylate | 7-Amino-3-[1-(1,2,4-triazolyl)methyl]-Δ$^3$-dephem-4-carboxylic acid | 149 (decomp.) (decomp.) | 1790, 1610, 1530 |

EXAMPLE 8

(1) In 40 ml of anhydrous methylene chloride was dissolved 2.72 g of 2-(2-tert.-amyloxycarboxamidothiazol-4-yl)-acetic acid, and 1.06 g of N-methylmorpholine was added to the solution, after which the reaction mixture was cooled to −35° C. Then, 1.12 g of ethyl chlorocarbonate was added thereto and reaction was effected at −35° C. to −25° C. for 1.5 hours. To the reaction mixture was added 4.62 g of diphenylmethyl 7-amino-3-[2-(5-methyl-1,2,3,4-tetrazolyl)methyl]-Δ$^3$-cephem-4-carboxylate, and the reaction was effected at −30° C. to −20° C. for 1 hour and then at −10° C. to +10° C. for 1 hour. After completion of the reaction, the solvent was removed by distillation under reduced pressure. The residue thus obtained was dissolved in a mixture of 40 ml of ethyl acetate and 30 ml of water. The organic layer was separated, again mixed with 30 ml of water and adjusted to a pH of 1.5 with 2N hydrochloric acid with ice-cooling. The organic layer was separated, mixed with 30 ml of water and adjusted to a pH of 7.0 with sodium hydrogen carbonate with ice-cooling. The organic layer was separated and dried on anhydrous magnesium sulfate, after which the solvent was removed by distillation under reduced pressure. Diethyl ether was added to the residue, and the resulting crystals were collected by filtration. They were thoroughly washed with diethyl ether and dried to obtain 6.52 g (yield 91.1%) of diphenylmethyl 7-[2-(2-tert.-amyloxycarboxamidothiazol-4-yl)acetamido]-3-[2-(5-methyl-1,2,3,4-tetrazolyl)methyl]-Δ$^3$-cephem-4-carboxylate having a melting point of 103°–105° C. (decomp.)

IR (KBr) cm$^{-1}$: $\nu_{C=O}$ 1780, 1720, 1675.

NMR (CDCl$_3$) ppm value:

0.90 (3H, t, J=7Hz, CH$_3$CH$_2$—C—),

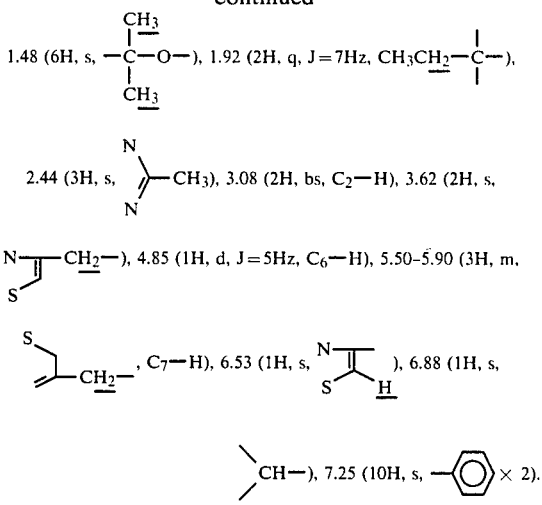

1.48 (6H, s, —C(CH$_3$)$_2$—O—), 1.92 (2H, q, J=7Hz, CH$_3$CH$_2$—C—), 2.44 (3H, s, tetrazolyl—CH$_3$), 3.08 (2H, bs, C$_2$—H), 3.62 (2H, s, N—N—CH$_2$—), 4.85 (1H, d, J=5Hz, C$_6$—H), 5.50–5.90 (3H, m, S—CH$_2$—, C$_7$—H), 6.53 (1H, s, thiazolyl-H), 6.88 (1H, s, >CH—), 7.25 (10H, s, —C$_6$H$_5$ × 2).

In 30 ml of anhydrous benzene was suspended 2.72 g of 2-(2-tert.-amyloxycarboxamidothiazol-4-yl)acetic acid, and 2.54 g of oxazolyl chloride was added to the suspension with ice-cooling, after which the resulting mixture was subjected to reaction at the same temperature for one hour. After completion of the reaction, the solvent was removed by distillation under reduced pressure, and the resulting residue was dissolved in 5 ml of anhydrous methylene chloride. The resulting solution was dropped into a solution of 4.62 g of diphenylmethyl 7-amino-3-[2-(5-methyl-1,2,3,4-tetrazolyl)methyl]-Δ$^3$-cephem-4-carboxylate and 1.21 g of dimethylaniline in 40 ml of anhydrous methylene chloride at −50° to −45° C. After completion of the dropping, the resulting mixture was subjected to reaction at −40° C. for 30 minutes, at −20° C. to −10° C. for 30 minutes, and then at 0° C. for 30 minutes. After completion of the reaction, the solvent was removed by distillation under reduced pressure, and the resulting residue was dissolved in 40 ml of ethyl acetate and 30 ml of water, after which the organic layer was separated. To the organic layer was added again 30 ml of water, and the pH of the resulting mixture was adjusted to 1.5 with 2 N hydrochloric acid with ice-cooling. The organic layer was subsequently separated, and 30 ml of water was added thereto, after which the pH of the resulting mixture was adjusted to 7.0 with sodium hydrogen carbonate with ice-cooling. The organic layer was separated, and dried on anhydrous magnesium sulfate, after which the solvent was removed by distilllation under reduced pressure. Diethyl ether was added to the resulting residue, and the crystals precipitated were collected by filtration, thoroughly washed with diethyl ether and then dried, to obtain 6.69 g (yield 93.5%) of diphenylmethyl 7-[2-(2-tert.-amyloxycarboxamidothiazol-4-yl)acetamido]-3-[2-(5-methyl-1,2,3,4-tetrazolyl)mathyl]-Δ3-cephem-4-carboxylate having a melting point of 103°–105° C. (decomp.).

The physical properties (IR and NMR) of this compound were identical with those of the compound obtained above.

(2) In a mixed solvent of 32 ml of trifluoroacetic acid and 10 ml of anisole was dissolved 6.52 g of diphenylmethyl 7-[2-(2-tert.-amyloxycarboxamidothiazol-4-yl)acetamide]-3-[2-(5-methyl-1,2,3,4-tetrazolyl)methyl]-Δ$^3$-cephem-4-carboxylate obtained in above (1). The solution was subjected to reaction at room temperature for 2 hours. After completion of the reaction, the solvent was removed by distillation under reduced pressure. Diethyl ether was added to the residue, and the resulting crystals were collected by filtration, washed thoroughly with diethyl ether and dried, to obtain 4.61 g (yield 92.1%) of trifluoroacetic acid salt of 7-[2-(2-aminothiazol-4-yl)acetamido]3-[2-(5-methyl-1,2,3,4-tetrazolyl)methyl]-Δ³-cephem-4-carboxylic acid having a melting point of 184°–187° C. (decomp.).

IR(KBr) cm$^{-1}$: $\nu_{C=O}$ 1765, 1655, 1630. NMR(d$_6$-DMSO) ppm value: 2.43

3.45 (4H, bs, C$_2$-H),

5.08 (1H, d, J=4 Hz, C$_6$-H), 5.50–590

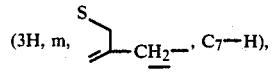

6.37

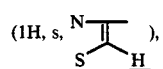

8.96 (1H, d, J=8 Hz, —CONH—).

In the same manner as above, the following compound was obtained:

Trifluoroacetic acid salt of 7[2-(2-aminothiazol-4-yl)acetamido]-3-acetamidomethyl-Δ³-cephem-4carboxylic acid Melting point: 153°–154° C. (decomp.)

(3) In 50 ml of water was suspended 5.5 g of trifluoroacetic acid salt of 7-[2-(2-aminothiazol-4yl)acetamido]-3-[2-(5-methyl-1,2,3-tetrazolyl)methyl]-Δ³-cephem-4-carboxylic acid, and 20 ml of 1 N aqueous solution of sodium hydroxide was slowly added to the suspension with ice-cooling. The reaction mixture was purified by a column chromatography with Amberlite XAD-2 (eluent: water) and the eluate was evaporated to dryness, to obtain 4.1 g (yield 88.4%) of sodium 7-[2-2-aminothiazol-4-yl)acetamido]-3-[2-(5-methyl1,2,3,4-tetrazolyl)methyl]-Δ³-cephem-4-carboxylate having a melting point of 182°–187° C. (decomp.).

IR(KBr) cm$^{-1}$: $\nu_{C=O}$ 0 1760, 1660, 1610.

NMR(d$_6$-DMSO) ppm value: 2.41 (3H, s, —CH$_3$), 3.40 (2H, bs, C$_2$-H), 3.62

4 93 (1H, d, J=5 Hz, C$_6$-H), 5.25–6.02

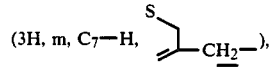

6.09

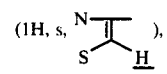

8.80 (1H, d, J=8 Hz, —CONH—).

In the same manner as above, the following compound was obtained:

Sodium 7-[2-(2-aminothiazol-4-yl)acetamido]-3-acetamidomethyl-Δ³-cephem-4-carboxylate Melting point: 155°–158° C. (decomp.).

IR(KBr) cm$^{-1}$: $\nu_{C=O}$ 1755, 1680 - 1590.

NMR(D$_2$O) ppm value: 1.98 (3H, s, —COCH$_3$), 3.16, 3.56 (2H, ABq, J=16 Hz, C$_2$-H), 3.52

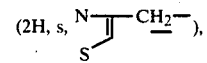

3.84, 4.15

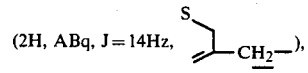

5.02 (1H, d, J=5 Hz, C$_6$-H), 5.57 (1H, d, J=5 Hz, C$_7$-H), 6.40

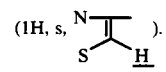

EXAMPLE 9

(1) In 30 ml of anhydrous methylene chloride was dissolved 2.72 g of 2-(2-tert.-amyloxycarboxamidothiazol-4-yl)-acetic acid, and 1.06 g of N-methylmorpholine was added thereto, after which the reaction mixture was cooled to −35° C. Then, 1.12 g of ethyl chlorocarbonate was added and the reaction was effected at −35° C. to −25° C. for 1.5 hours, after which the reaction mixture was cooled to −40° C. On the other hand, 2.96 g of 7-amino-3-[2-(5-methyl-1,2,3,4-tetrazolyl)methyl]Δ³-cephem-4-carboxylic acid was suspended in 30 ml of anhydrous methylene chloride, and 6.1 g of N,O-bis(trimethylsilyl)acetamide was added to the suspension with ice-cooling, after which the resulting mixture was subjected to reaction at 5°–10° C. for 40 minutes until it became a homogenerous solution. The solution was dropped into the reaction mixture prepared above while keeping the temperature at −40° C. to −30° C. After the dropping, the mixture was subjected to reaction at −30° C. to −20° C. for 1 hour and then at −10° C. to +10° C. for 1 hour. After completion of the reaction, the solvent was removed by distillation under reduced pressure, 40 ml of ethyl acetate and 40 ml of water were added to the residue to dissolve the latter, and the pH thereof was adjusted to 7.5 with sodium hydrogen carbonate with ice-cooling. The aqueous layer was separated, mixed with 40 ml of ethyl acetate and adjusted to a pH of 2.0 with 2 N hydrochloric acid with ice-cooling. Then, the organic layer was separated, washed with 30 ml of water and dried on anhydrous magnesium sulfate, after which the solvent was removed by distillation under reduced pressure, to obtain 5.07 g (yield 92.2%) of 7-[2-(2-tert.-amyloxycarboxamido- thiazol-4-yl)acetamido]-3-[2-(5-methyl- 1,2,3,4-tetrazolyl)methyl]-Δ³-cephem-4-carboxylic acid having a melting point of 138°–142° C. (decomp.).

IR(KBr) cm⁻¹: $\nu_{C=O}$ 1775, 1720, 1675.

NMR(d₆-DMSO) ppm value:

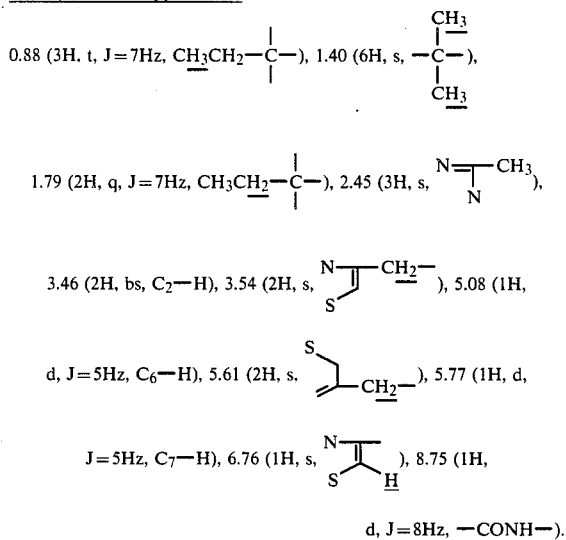

(2) In a mixed solvent of 25 ml of trifluoroacetic acid and 8 ml of anisole was dissolved 5.07 g of the 7-[2-(2-tert.-amyloxycarboxamidothiazol-4-yl)acetamido]-3-[2-(5-methyl-1,2,3,4-tetrazolyl)methyl]Δ³-cephem-4-carboxylic acid obtained in above (1). The resulting solution was subjected to reaction at room temperature for 30 minutes. After completion of the reaction, the solvent was removed by distillation under reduced pressure, and diethyl ether was added to the residue, after which the resulting crystals were collected by filtration, thoroughly washed with diethyl ether and dried to obtain 4.72 g (yield 93.1%) of trifluoroacetic acid salt of 7-[2-(2-aminothiazol-4-yl)acetamido]-3-[2-(5-methyl-1,2,3,4-tetrazolyl)methyl]-Δ³-cephem-4-carboxylic acid having a melting point of 184°–187° C. (decomp.).

The physical properties (IR and NMR) of this compound were identical with those of the product obtained in Example 8-(2).

EXAMPLE 10

(1) A solution of 0.46 g of chlorine in 5 ml of anhydrous carbon tetrachloride was dropped at −30° C. into a solution of 0.55 g of diketene in 10 ml of anhydrous methylene chloride, and the resulting mixture was subjected to reaction at −30° C. to −20° C. for 30 minutes to obtain a solution of acid chloride. On the other hand, 2.12 g of N,O-bis(trimethylsilyl)acetamide was added to a suspension of 1.48 g of 7-amino-3-[2-(5-methyl-1,2,3,4-tetrazolyl)methyl]-Δ³-cephem-4-carboxylic acid in 20 ml of anhydrous methylene chloride with ice-cooling, and the reaction was effected at room temperature for 1 hour, after which the reaction mixture was cooled to −40° C. Then, the acid chloride solution prepared above was dropped thereinto at that temperature. After completion of the dropping, the temperature was slowly elevated and the reaction was effected at 0°–5° C. for 1 hour. After completion of the reaction, the solvent was removed by distillation under reduced pressure, and the residue was dissolved in 30 ml of ethyl acetate and 20 ml of water, after which the organic layer was separated, washed successively with 20 ml of water and 20 ml of saturated aqueous solution of sodium chloride, and dried on anhydrous magnesium sulfate. The solvent was removed by distillation under reduced pressure. Diethyl ether was added to the residue and the resulting crystals were collected by filtration, thoroughly washed with diethyl ether and dried, to obtain 1.85 g (yield 89.4%) of 7-(4-chloro-3-oxobutyramido)-3-[2-(5-methyl-1,2,3,4-tetrazolyl)methyl]-Δ³-cephem-4-carboxylic acid having a melting point of 98°–101° C. (decomp.).

IR(KBr) cm⁻¹: $\nu_{C=O}$ 1778, 1725, 1668.

NMR(d₆-DMSO) ppm value: 2.44 (3H, s, —CH₃), 3.42 (2H, bs, C₂-H 3.56 (2H, s, —COCH₂CO—), 4.52 (2H, s, —ClCH₂—), 5 08 (1H, d, J=5Hz, C₆-H), 5.31–5.89

(3H, m, 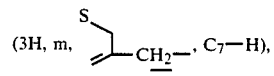, C₇—H), 8.99 (1H, d, J=8 Hz, —CONH—).

(2) In 5 ml of dimethylformamide were dissolved 0.82 g of the 7-(4-chloro-3-oxobutyramido)-3-[2-(5-methyl-1,2,3,4-tetrazolyl)methyl]-Δ³-cephem-4-carboxylic acid obtained in above (1) and 0.167 g of thiourea, and the solution was subjected to reaction at room temperature for 2 hours. After completion of the reaction, the reaction mixture was thrown into 5 ml of water, and the pH was adjusted to 5.0 with sodium hydrogen carbonate with ice-cooling. The resulting precipitate was collected by filtration, washed successively with water, acetone and diethyl ether and dried to obtain 0.77 g (yield 88.3%) of 7-[2-(2-aminothiazol-4-yl)acetamido]-3-[2-(5-methyl1,2,3,4-tetrazolyl)methyl]-Δ³-cephem-4-carboxylic acid having a melting point of 203°–208° C. (decomp.).

IR(KBr) cm⁻¹: $\nu_{C=O}$ 1760, 1650, 1625.

NMR(d₆-DMSO) ppm value: 2.34 (3H, s, —CH₃), 3.40 (4H, bs, C₂-H),

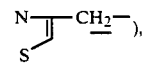, 4.92 (1H, d, J=5 Hz, C₆-H), 5.18–5.80

(3H, m, C₇—H, 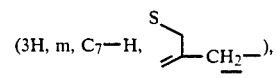), 6.10 1H, s,

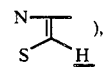, 8.68 (1H, d, J=8 Hz, —CONH—).

By reacting thioformamide in place of thiourea in the above procedure, the following compound was obtained:

7[2-(thiazol-4-yl)acetamido]-3 [2-(5-methyl1,2,3,4-tetrazolyl)methyl]-Δ³-cephem-4-carboxylic acid Melting point: 140°–142° C.(decomp.).

IR(KBr) cm⁻¹: $\nu_{C=O}$ 1775, 1720, 1660.

NMR(d₆-DMSO) ppm value: 2.44 (3H, s, —CH₃), 3.44 (2H, bs, C₂-H), 3 79

(2H, s, 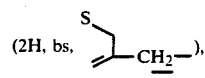), 5.06 (1H, d, J=5 Hz, C₆-H), 5.60

(2H, bs, 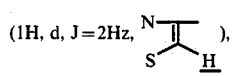), 5.6-5.8 (1H, m, C₇-H), 7.45

(1H, d, J=2Hz, 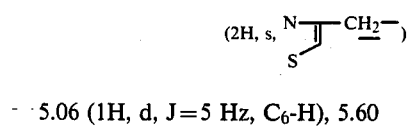), 9.08

(1H, d, J=2Hz, 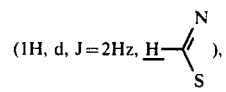), 9.00-9.25 (1H, m, —CONH—).

1 EXAMPLE 11

By subjecting the starting compounds shown in Table 13 to the same reaction as in Example 8, 9 or 10, the corresponding compounds shown in Table 13 were obtained.

TABLE 13

Trifluoroacetic acid·H₂N—[thiazole]—CH₂CONH—[β-lactam]—CH₂R²
COOH

| Compound R² | Melting point (°C.) | IR(KBr) cm⁻¹:ν$_{C=O}$ | NMR (d₆-DMSO*, CD₃OD***  / d₆-DMSO + D₂O**, CF₃COOD****) ppm value: |
|---|---|---|---|
| —N(N=N)N—CH₂CH₃ tetrazolyl | 115 (decomp.) | 1780, 1670, 1630 | *1.27 (3H, t, J=7Hz, —CH₂CH₃), 2.84 (2H, q, J=7Hz, —CH₂CH₃), 3.20-380 (4H, m, C₂—H, N⟨⟩CH₂—), 5.13 (1H, d, J=5Hz, C₆—H), 5.45-5.85 (3H, m, C₇—H, S-CH₂—), 6.53 (1H, s, N⟨⟩H ) |
| —N(N=N)N=N —CH₂CH₃ | 152 (decomp.) | 1775, 1670, 1630 | *1.30 (3H, t, J=7Hz, —CH₂CH₃), 2.94 (2H, q, J=7Hz, —CH₂CH₃), 3.45 (2H, s, C₂—H), 3.56 (2H, s, N⟨⟩CH₂— ), 5.12 (1H, d, J=5Hz, C₆—H), 5.25-5.85 (3H, m, C₇—H, S-CH₂—), 6.56 (1H, s, N⟨⟩H ), 9.14 (1H, d, J=8Hz, —CONH—) |
| —N(N=N)N—COOCH₂CH₃ | 137-140 (decomp.) | 1770, 1740, 1670, 1630 | *1.36 (3H, t, J=7Hz, —CH₂CH₃), 3.47 (2H, bs, C₂—H), 3.70 (2H, s, N⟨⟩CH₂— ), 4.41 (2H, q, J=7Hz, —CH₂CH₃), 5.08 (1H, d, J=5Hz, C₆—H), 5.50-5.80 (3H, m, C₇—H, S-CH₂—), 6.48 (1H, s, N⟨⟩H ) |

TABLE 13-continued

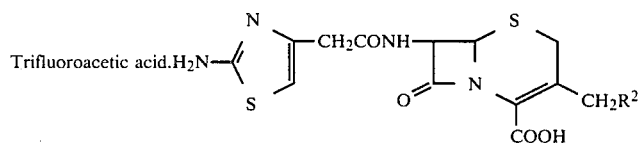

| Compound $R^2$ | Melting point (°C.) | IR(KBr) cm$^{-1}$:$\nu_{C=O}$ | NMR $\begin{pmatrix} \text{d}_6\text{-DMSO*, CD}_3\text{OD*} \\ \text{d}_6\text{-DMSO + D}_2\text{O, CF}_3\text{COOD****} \end{pmatrix}$ ppm value: |
|---|---|---|---|
| −N(N=N)−C(COOCH$_2$CH$_3$)=N (tetrazolyl with COOCH$_2$CH$_3$) | 149–154 (decomp.) | 1775, 1740, 1670, 1630 | *1.36 (3H, t, J=7Hz, −CH$_2$CH$_3$), 3.50 (2H, bs, C$_2$−H), 3.71 (2H, s, N−CH$_2$− in thiazoline), 4.40 (2H, q, J=7Hz, −CH$_2$CH$_3$), 5.06 (1H, d, J=5Hz, C$_6$−H), 5.60–5.85 (3H, m, C$_7$−H, S−CH$_2$−), 6.47 (1H, s, thiazoline-H) |
| −N(N=N)−C(C$_6$H$_5$)=N (tetrazolyl with phenyl) | 133 (decomp.) | 1770, 1670, 1630 | *3.55 (4H, bs, C$_2$−H, N−CH$_2$−), 5.05 (1H, d, J=5Hz, C$_6$−H), 5.50–5.80 (3H, m, C$_7$−H, S−CH$_2$−), 6.55 (1H, s, thiazoline-H), 7.40–8.10 (5H, m, phenyl) |
| −N(N=N)−CH=N (tetrazolyl) | 148 (decomp.) | 1778, 1710, 1668 | *3.44 (2H, bs, C$_2$−H), 3.56 (2H, bs, N−CH$_2$−), 5.08 (1H, d, J=5Hz, C$_6$−H), 5.42–5.93 (3H, m, S−CH$_2$−, C$_7$−H), 6.57 (1H, s, thiazoline-H), 8.90 (1H, s, N=CH−N), 9.13 (1H, d, J=8Hz, −CONH−) |
| −N(N=N)−N=CH (tetrazolyl isomer) | 100–102 (decomp.) | 1780, 1710, 1670 | *3.60 (2H, bs, C$_2$−H), 3.68 (2H, bs, N−CH$_2$−), 5.06 (1H, d, J=5Hz, C$_6$−H), 5.30–5.85 (3H, m, S−CH$_2$−, C$_7$−H), 6.59 (1H, s, thiazoline-H), 9.15 (1H, s, CH=N), 9.17 (1H, d, J=8Hz, −CONH−) |

TABLE 13-continued

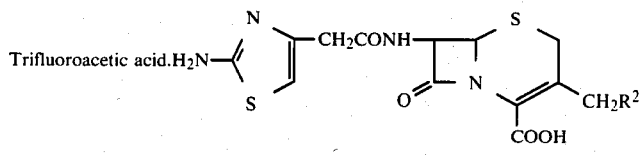
Trifluoroacetic acid.H₂N—

| Compound R² | Melting point (°C.) | IR(KBr) cm⁻¹:ν$_{C=O}$ | NMR (d₆-DMSO*, CD₃OD*** / d₆-DMSO + D₂O**, CF₃COOD****) ppm value: |
|---|---|---|---|
| tetrazole-NHCOCH₃ | 143 (decomp.) | 1770, 1690, 1665, 1630 | *2.10 (3H, s, —CH₃), 3.50 (4H, bs, C₂—H, N=C(S)—CH₂—), 5.10 (1H, d, J=5Hz, C₆—H), 5.50-5.85 (3H, m, S—CH₂—, C₇—H), 6.50 (1H, s, thiazole-H), 9.05 (1H, d, J=8Hz, —CONH—) |
| tetrazole-NH₂ | 185 (decomp.) | 1770, 1665, 1630 | **3.47 (2H, bs, C₂—H), 3.55 (2H, s, N=C(S)—CH₂—), 5.10 (1H, d, J=5Hz, C₆—H), 5.45 (2H, bs, S—CH₂—), 5.70 (1H, d, J=5Hz, C₇—H), 6.55 (1H, s, thiazole-H) |
| tetrazole-SCH₃ | 107 (decomp.) | 1765, 1665, 1630 | *2.60 (3H, s, —CH₃), 3.55 (4H, bs, C₂—H, N=C(S)—CH₂—), 5.05 (1H, d, J=5Hz, C₆—H), 5.50-5.80 (3H, m, C₇—H, S—CH₂—), 6.55 (1H, s, thiazole-H) |
| thiadiazole-SCH₃ | 107 (decomp.) | 1776, 1665, 1630 | **2.70 (3H, s, —CH₃), 3.35 (2H, bs, C₂—H), 3.50 (2H, s, N=C(S)—CH₂—), 5.10 (1H, d, J=5Hz, C₆—H), 5.30 (2H, s, S—CH₂—), 5.70 (1H, d, J=5Hz, C₇—H), 6.60 (1H, s, thiazole-H) |
| triazole-CH₃ | 150-153 (decomp.) | 1770, 1665, 1630 | *2.49 (3H, s, —CH₃), 3.40 (2H, s, C₂—H), 3.52 (2H, s, N=C(S)—CH₂—), 5.05 (1H, d, J=5Hz, C₆—H), 5.28 (2H, bs, S—CH₂—), 5.62 (1H, dd, J=5Hz, J=8Hz, C₇—H), 6.49 (1H, s, thiazole-H), 9.03 (1H, d, J=8Hz, —CONH—) |

TABLE 13-continued

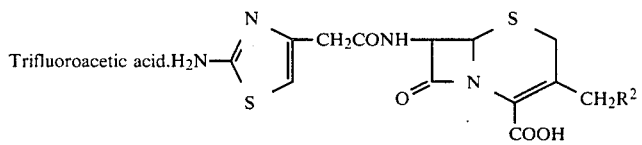

Trifluoroacetic acid.H$_2$N— [thiazole]—CH$_2$CONH—[β-lactam]—CH$_2$R$^2$, COOH

| Compound R$^2$ | Melting point (°C.) | IR(KBr) cm$^{-1}$:$\nu_{C=O}$ | NMR (d$_6$-DMSO*, CD$_3$OD***; d$_6$-DMSO + D$_2$O**, CF$_3$COOD****) ppm value: |
|---|---|---|---|
| 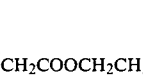  (tetrazole-CH$_2$COOCH$_2$CH$_3$) | 120–123 (decomp.) | 1765, 1730, 1665, 1630 | *1.20 (3H, t, J=7Hz, —CH$_2$CH$_3$), 3.42 (2H, bs, C$_2$—H), 3.50 (2H, bs, [N=CH$_2$-S]), 4.00 (2H, s, —CH$_2$COO—), 4.02 (2H, q, J=7Hz, —CH$_2$CH$_3$), 5.05 (1H, d, J=5Hz, C$_6$—H), 5.15, 5.65 (2H, ABq, J=14Hz, [S-CH$_2$-]), 5.70 (1H, d, J=5Hz, C$_7$—H), 6.50 (1H, s, [N=CH-S, H]) |
| 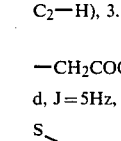  (1,2,4-triazole) | 119 (decomp.) | 1770, 1660, 1630 | *3.43 (2H, bs, C$_2$—H), 3.52 (2H, bs, [N=CH$_2$-S]), 5.02–5.35 (3H, m, C$_6$—H, [S-CH$_2$-]), 5.63 (1H, d, J=5Hz, C$_7$—H), 6.55 (1H, s, [N=CH-S, H]), 7.95 (1H, s, [N=N-H]), 8.47 (1H, s, [N=N-H]) |
|   (oxadiazole-CH(CH$_3$)) | 1144–146 (decomp.) | 1765, 1665, 1630 | *2.23 (3H, s, —CH$_3$), 3.45 (2H, bs, C$_2$—H), 3.58 (2H, bs, [N=CH$_2$-S]), 5.05–5.20 (3H, m, C$_6$—H, [S-CH$_2$-]), 5.70 (1H, d, J=5Hz, C$_7$—H), 6.60 (1H, s, [N=CH-S, H]), 8.38 (1H, s, [N=N-H]) |
| 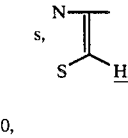  (oxadiazole-SCH$_3$) | 133 (decomp.) | 1765, 1665, 1630 | **2.50 (3H, s, —CH$_3$), 3.50 (2H, bs, C$_2$—H), 3.60 (2H, bs, [N=CH$_2$-S]), 5.05 (1H, d, J=5Hz, C$_6$—H), 5.10 (2H, s, [S-CH$_2$-]), 5.65 (1H, d, J=5Hz, C$_7$—H), 6.60 (1H, s, [N=CH-S, H]), 8.40 (1H, s, [N=N-H]) |

TABLE 13-continued

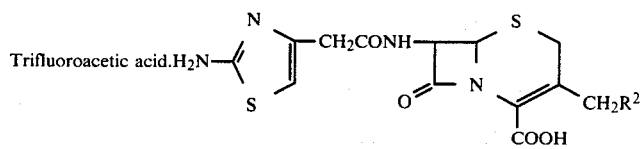

| Compound R² | Melting point (°C.) | IR(KBr) cm⁻¹:$\nu_{C=O}$ | NMR $\begin{pmatrix} d_6\text{-DMSO*, CD}_3\text{OD*} \\ d_6\text{-DMSO + D}_2\text{O, CF}_3\text{COOD****} \end{pmatrix}$ ppm value: |
|---|---|---|---|
| (N—N oxadiazole with COOCH₂CH₃) | 155–158 (decomp.) | 1765, 1725, 1660, 1630 | *1.34 (3H, t, J=7Hz, —CH₂CH₃), 3.41 (2H, bs, C₂—H), 3.53 (2H, bs, [N-CH₂-S]), 4.38 (2H, q, J=7Hz, —CH₂CH₃), 5.10 (1H, d, J=5Hz, C₆—H), 5.50–5.85 (3H, m, C₇—H, [S-CH₂-]), 6.55 (1H, s, [N-S-H]), 8.14 (1H, s, [N-N-H]) |
| (N—N oxadiazole with Cl) | 140 (decomp.) | 1765, 1665, 1630 | **3.47 (2H, bs, C₂—H), 3.65 (2H, s, [N-CH₂-S]), 5.10 (1H, d, J=5Hz, C₆—H), 5.10, 5.40 (2H, ABq, J=16Hz, [S-CH₂-]), 5.70 (1H, d, J=5Hz, C₇—H), 6.65 (1H, s, [N-S-H]), 8.02 (1H, s, [N-N-H]) |
| (triazole with COOCH₃COOCH₃) | 137–140 (decomp.) | 1775, 1730, 1640 | *3.49 (2H, bs, C₂—H), 3.70 (2H, s, [N-CH₂-S]), 3.82 (3H, s, —OCH₃), 3.87 (3H, s, —OCH₃), 5.06 (1H, d, J=5Hz, C₆—H), 5.32–5.85 (3H, m, [S-CH₂-], C₇—H), 6.51 (1H, s, [N-S-H]), 9.03 (1H, d, J=8Hz, —CONH—) |
| (triazole with CN, phenyl) | 153 (decomp.) | 1770, 1670, 1630 | *3.55 (4H, bs, C₂—H, [N-CH₂-S]), 5.05 (1H, d, J=5Hz, C₆—H), 5.50–5.80 (3H, m, C₇—H, [S-CH₂-]), 6.55 (1H, s, [N-S-H]), 7.40–8.20 (5H, m, phenyl) |
| (N—N oxadiazole with NHCOCH₃) | 180 (decomp.) | 1770, 1690, 1670, 1630 | — |

TABLE 13-continued

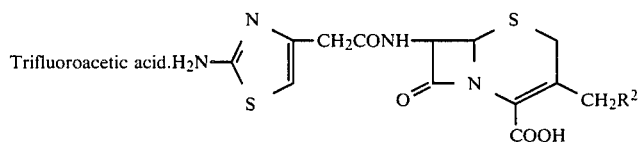

Trifluoroacetic acid.

| Compound R² | Melting point (°C.) | IR(KBr) cm⁻¹:ν$_{C=O}$ | NMR (d₆-DMSO*, CD₃OD*** / d₆-DMSO + D₂O**, CF₃COOD****) ppm value: |
|---|---|---|---|
| —NHCCH₂Cl‖O | 124–125 (decomp.) | 1770, 1660, 1630 | *3.50 (2H, bs, C₂—H), 3.55 (2H, s, [N—CH₂—/S]), 3.91, 4.15 (2H, ABq, J=12Hz, [S/CH₂—]), 4.10 (2H, s, ClCH₂—), 5.03 (1H, d, 5Hz, C₆—H), 5.65 (1H, dd, J=5Hz, J=8Hz, C₇—H), 6.53 (1H, s, [N/S—H]), 9.01 (1H, d, J=8Hz, —CONH—) |
| —NHC(phenyl)‖O | 137–141 (decomp.) | 1760, 1660, 1640 | *3.58 (2H, s, [N—CH₂—/S]), 3.62, 3.84 (2H, ABq, J=12Hz, C₂—H), 4.18–4.53 (2H, m, [S/CH₂—]), 5.05 (1H, d, J=5Hz, C₆—H), 5.67 (1H, dd, J=5Hz, J=8Hz, C₇—H), 6.57 (1H, s, [N/S—H]), 7.22–8.03 (5H, m, —C(=O)—phenyl), 8.60–8.92 (1H, m, CH₂NHCO—), 9.02 (1H, d, J=8Hz, —CONH—) |
| —NHC(CH₂)₄CH₃‖O | 105–108 (decomp.) | 1765, 1660, 1640 | *0.87 (3H, t, J=7Hz, —CH₂CH₂CH₂CH₂CH₃), 1.05–1.70 (6H, m, —CH₂CH₂CH₂CH₂CH₃), 2.08 (2H, 5, J=7Hz, —CH₂CH₂CH₂CH₂CH₃), 3.41 (2H, bs, C₂—H), 3.57 (2H, s, [N—CH₂—/S]), 4.01 (2H, bs, [S/CH₂—]), 5.00 (1H, d, J=5Hz, C₆—H), 5.63 (1H, dd, J=5Hz, J=8Hz, C₇—H), 6.55 (1H, s, [N/S—H]), 8.10 (1H, bs, CH₂NHCO—) |

TABLE 13-continued

Trifluoroacetic acid.H₂N—[structure: aminothiazole-CH=C-CH₂CONH-β-lactam-S-CH₂-C(=CH₂R²)-COOH]

| Compound R² | Melting point (°C.) | IR(KBr) cm⁻¹:ν$_{C=O}$ | NMR (d₆-DMSO*, CD₃OD***  /  d₆-DMSO + D₂O**, CF₃COOD****) ppm value: |
|---|---|---|---|
| —NHC(=O)(CH₂)₂CH₃ | 114–116 (decomp.) | 1765, 1660, 1640 | *0.84 (3H, s, J=7Hz, —CH₂CH₂C$\underline{H}$₃), 1.18–1.82 (2H, m, —CH₂C$\underline{H}$₂CH₃), 2.05 (2H, t, J=7Hz, —C$\underline{H}$₂CH₂CH₃), 3.42 (2H, bs, C₂—H), 3.51 (2H, s, [thiazole-CH₂—]), 3.85–4.26 (2H, m, [S-CH₂-]), 5.01 (1H, d, J=5Hz, C₆—H), 5.70 (1H, dd, J=5Hz, J=8Hz, C₇—H), 6.50 (1H, s, [thiazole-H]), 8.07 (1H, t, J=6Hz, >CH₂N$\underline{H}$CO—) |
| —NHC(=O)-furyl | 175–176 (decomp.) | 1780, 1710, 1665, 1660 | *3.03–3.57 (6H, m, C₂—H, [CH₂], [thiazole-CH₂—]), 4.87 (1H, d, J=5Hz, C₆—H), 5.32–5.70 (1H, m, C₇—H), 6.25–7.61 (4H, m, [thiazole-H, furyl-H]), 8.20 (1H, bs, >CH₂N$\underline{H}$CO—), 8.81 (1H, d, J=8Hz, —CONH—) |
| —C₆H₄—OH (para) | 161–163 (decomp.) | 1760, 1710~1620 | *3.04–3.83 (6H, m, C₂—H, [CH₂], [thiazole-CH₂—]), 5.00 (1H, d, J=5Hz, C₆—H), 5.36–5.72 (1H, m, C₇—H), 6.24–7.39 (5H, m, [thiazole-H, —C₆H₄—O—]), 8.96 (1H, d, J=8Hz, —CONH—) |
| —C₆H₅ | 155 (decomp.) | 1760, 1660, 1630 | ****3.43 (2H, bs, C₂—H), 3.86 (2H, s, [thiazole-CH₂—]), 4.20 (2H, m, [S-CH₂-]), 5.22 (1H, d, J=5Hz, C₆—H), 6.05 (1H, m, C₇—H), 6.62 (1H, s, [thiazole-H]), 7.22 (5H, bs, —C₆H₅) |

TABLE 13-continued

Trifluoroacetic acid.H$_2$N-[thiazole]-CH$_2$CONH-[β-lactam]-CH$_2$R$^2$, COOH

| Compound R$^2$ | Melting point (°C.) | IR(KBr) cm$^{-1}$:ν$_{C=O}$ | NMR (d$_6$-DMSO*, CD$_3$OD***; d$_6$-DMSO + D$_2$O**, CF$_3$COOD****) ppm value: |
|---|---|---|---|
| [thiophene]-COOH | 184 (decomp.) | 1765, 1710, ~1620 | ****3.12–4.12 (6H, m, C$_2$—H, S-CH$_2$-, N=C(S)-CH$_2$-), 5.00 (1H, d, J=5Hz, C$_6$—H), 5.57 (1H, d, J=5Hz, C$_7$—H), 6.45 (1H, s, thiazolyl-H), 7.30 (1H, d, J=3.5Hz, thienyl-COOH), 7.52 (1H, d, J=3.5Hz, thienyl-COOH) |
| [thiophene]-COOCH$_3$ | 151–153 (decomp.) | 1768, 1705~1620 | ***3.15, 3.48 (2H, ABq, J=18Hz, C$_2$—H), 3.62 (2H, s, N=C(S)-CH$_2$-), 3.82 (3H, s, —OCH$_3$), 3.60, 4.03 (2H, ABq, J=15Hz, S-CH$_2$-), 5.08 (1H, d, J=5Hz, C$_6$—H), 5.68 (1H, d, J=5Hz, C$_7$—H), 6.54 (1H, s, thiazolyl-H), 7.53 (1H, d, J=3.5Hz, thienyl-COOCH$_3$), 7.67 (1H, d, J=3.5Hz, thienyl-COOCH$_3$) |
| [furan]-COOH | 183–187 (decomp.) | 1765, 1710~1610 | ***3.45 (2H, bs, C$_2$—H), 3.64 (2H, s, N=C(S)-CH$_2$-), 3.90 (2H, bs, S-CH$_2$-), 4.92 (1H, d, J=5Hz, C$_6$—H), 5.51 (1H, d, J=5Hz, C$_7$—H), 6.19 (1H, d, J=4Hz, furyl-COOH), 6.48 (1H, s, thiazolyl-H), 6.97 (1H, d, J=4Hz, furyl-COOH) |

1. EXAMPLE12

(1) A solution of 1.92 g of bromine in 12 ml of anhydrous methylene chloride was dropped at −30° C. into a solution of 1.26 g of diketene in 20 ml of anhydrous methylene chloride, and the reaction was effected at −30° C. to −20° C. for 30 minutes. Then, the reaction mixture was dropped into a solution of 4.62 g of diphenylmethyl 7-amino-3-[2-(5-methyl-1,2,3,4-tetrazolyl)-methyl]-Δ³-cephem-4-carboxylate and 4 g of N,O-bis(-trimethylsilyl)acetamide in 50 ml of anhydrous chloroform at a temperature of −30° C. or below. After the dropping, the mixture was subjected to reaction at −30° C. to −20° C. for 30 minutes and then at −10° C. to 0° C. for 1 hour. After completion of the reaction, the solvent was removed by distillation under reduced pressure, the residue obtained was dissolved in 60 ml of ethyl acetate and 60 ml of water, and the organic layer was separated, washed successively with 30 ml of water and 30 ml of saturated aqueous solution of sodium chloride, and dried on anhydrous magnesium sulfate, after which the solvent was removed by distillation under reduced pressure. Diethyl ether was added to the residue and the resulting crystals were collected by filtration to obtain 5.92 g (yield 94.7%) of diphenylmethyl 7-(4-bromo-3-oxobutyramido)3-[2-(5-methyl-1,2,3,4-tetrazolyl)methyl]-Δ³-cephem-4-carboxylate having a melting point of 82°-85° C. (decomp.).

IR(KBr) cm⁻¹ ⁸⁴ C=O 1780, 1722, 1690–1650.

NMR(CDCl₃) ppm value: 2.42

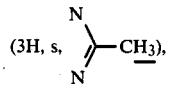

(3H, s, ⟩—CH₃), 3.19 (2H, bs, C₂-H), 3.62 (2H, s, —COCH₂CO—), 3.97 (2H, s, BrCH₂-), 4.86 (1H, d, J=5Hz, C₆-H), 5.20–6.0

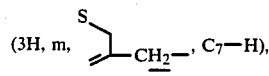

(3H, m, ... —CH₂—, C₇-H), 6.89 (1H, s, >CH—), 7.25

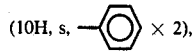

(10H, s, —⌬ × 2), 7.91 (1H, d, J=8 Hz, —CONH—).

(3) In 30 ml of N,N-dimethylformamide were dissolved 6.52 g of diphenylmethyl 7-(4-bromo-3-oxobutyramido)-3-[2-(5-methyl-1,2,3,4-tetrazolyl)methyl]-Δ³-cephem-4-carboxylate and 1.67 g of N-phenyl-thiourea, and the solution was subjected to reaction at room temperature for 2 hours. After completion of the reaction, the solvent was removed by distillation under reduced pressure, and the residue was washed with diethyl ether and then mixed with 100 ml of ethyl acetate and 50 ml of water. The pH of the mixture was adjusted to 7.5 with saturated aqueous solution of sodium hydrogen carbonate with ice-cooling, after which the organic layer was separated and dried on anhydrous magnesium sulfate. The solvent was removed by distillation under reduced pressure, to obtain 5.9 g of diphenylmethyl 7-[2-(2-phenylaminothiazol-4-yl)acetamido]-3-[2-(5-methyl-1,2,3,4-tetrazolyl)methyl]-Δ³-cephem-4-carboxylate as a crude solid product. Without purification, it was dissolved in 59 ml of anisole, and then 59 ml of trifluoroacetic acid was dropped thereinto, after which the mixture was subjected to reaction at room temperature for 30 minutes. After completion of the reaction, the solvent was removed by distillation under reduced pressure, and diethyl ether was added to the residue, after which the resulting crystals were collected by filtration, thoroughly washed with diethyl ether and dried to obtain trifluoroacetic acid salt of 7-[2-(2-phenylaminothiazol-4-yl)acetamido]-3 -[2-(5-methyl-1,2,3,4-tetrazolyl)methy.1]-Δ³-cephem-4-carboxylic acid having a melting point of 165°–169° C. (decomp.)

IR(KBr) cm⁻¹: $\nu_{C=O}$ 1775 1660, 1625.

NMR(d₆-DMSO) ppm value:

2.42 (3H, s, 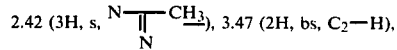), 3.47 (2H, bs, C₂—H), 3.53 (2H, s, 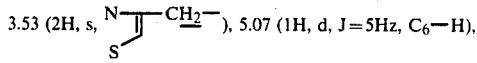), 5.07 (1H, d, J=5Hz, C₆—H), 5.59 (2H, bs, 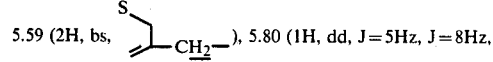), 5.80 (1H, dd, J=5Hz, J=8Hz, C₇—H), 6.53 (1H, s, 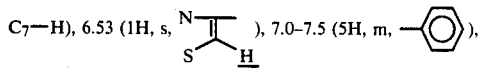), 7.0–7.5 (5H, m, —⌬), 8.95 (1H, d, J=8Hz, —CONH—)

EXAMPLE 13

In 27 ml of N,N-dimethylformamide was dissolved 5.5 g of the 7-[2-(2-tert.-amyloxycarboxamidothiazol-4-yl)acetamido]-3-[2-(5-methyl-1,2,3,4-tetrazolyl)methyl]-Δ³-cephem-4-carboxylic acid obtained in Example 9-(1). Then, 1 g of triethylamine and 2.9 g of pivaloyloxymethyl iodide were added to the solution with ice-cooling, and the resulting mixture was subjected to reaction for 30 minutes. After completion of the reaction, the reaction mixture was introduced into a mixed solvent of 250 ml of water and 250 ml of ethyl acetate, and the pH thereof was adjusted to 7.0 with sodium hydrogen carbonate. The organic layer was separated, washed with water and dried on anhydrous magnesium sulfate. The solvent was removed by distillation under reduced pressure, to obtain 6.02 g of pivaloyloxymethyl 7-[2-(2-tert.-amyloxycarboxamidothiazol-4-yl)acetamido]-3-[2-(5-methyl-1,2,3,4-tetrazolyl)methyl]-Δ³-cephem-4-carboxylate as a crude solid product. Without purification, it was dissolved in 30 ml of trifluoroacetic acid and the solution was subjected to reaction at room temperature for 30 minutes. After completion of the reaction, the solvent was removed by distillation under reduced pressure, 80 ml of water and 80 ml of ethyl acetate were added to the residue obtained, and the pH thereof was adjusted to 7.0 with sodium hydrogen carbonate with ice-cooling. The organic layer was separated and dried on anhydrous magnesium sulfate, and a solution of 0.8 g of dry hydrogen chloride in 20 ml of diethyl ether was added thereto with stirring while cooling the mixture with ice, upon which white colored powder precipitated. It was collected by filtration, thoroughly washed with diethyl ether and recrystallized from ethyl acetate to obtain 3.82 g of hydrochloride of pivaloyoxymethyl 7-[2-(2-aminothiazol-4-yl)acetamido]-3-[2-(5-methyl1,2,3,4-tetrazolyl)methyl]-Δ³-cephem-4-carboxylate having a melting point of 146°–148° C. (decomp.).

IR(KBr) cm⁻¹: $\nu_{C=O}$ 1782, 1750, 1670.

NMR(d₆-DMSO) ppm value: 1.15 (9H, s, —C(CH₃)₃), 2.46

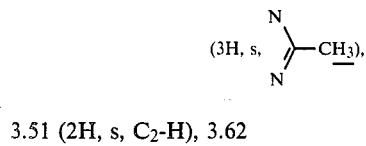 (3H, s,  —CH₃), 3.51 (2H, s, C₂-H), 3.62

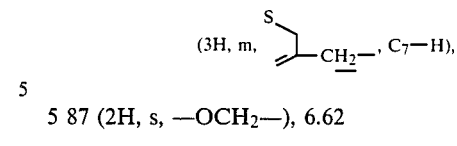 (3H, m, —CH₂—, C₇—H), 5.87 (2H, s, —OCH₂—), 6.62

(2H, s, N⫞CH₂—), (1H, s, N⫞H), 5.15 (1H, d, J—5 Hz, C₆-H), 5.26–5.79

9.23 (1H, d, J=8 Hz, —CONH—).

EXAMPLE 14

By subjecting the starting compounds shown in Tables 14 and 15 to the same reaction as in Example 13, the corresponding compounds shown in Tables 14 and 15 were obtained.

TABLE 14

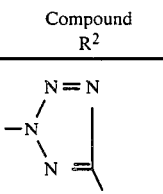

| Compound R² | Melting point (°C.) | IR(KBr) cm⁻¹: $\nu_{C=O}$ | NMR(*¹d₆-DMSO, *²CDCl₃, *³D₂O) ppm value: |
|---|---|---|---|
| 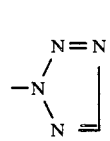 —N(N=N)N—CH₂CH₃ | 124–127 (decomp.) | 1780, 1750, 1670 | *¹1.15 (9H, s, —C(CH₃)₃), 1.26 (3H, t, J=7Hz, —CH₂CH₃), 2.83 (2H, q, J=7Hz, —CH₂CH₃), 3.52 (2H, s, C₂—H), 3.62 (2H, s, N⫞CH₂—), 5.14 (1H, d, J=5Hz, C₆—H), 5.46–6.00 (5H, m, S⫞CH₂—, —OCH₂O—, C₇—H), 6.06 (1H, s, N⫞H), 9.22 (1H, d, J=8Hz, —CONH—) |
| —N(N=N)N= | 112–115 (decomp.) | 1780, 1750, 1670 | *¹1.17 (9H, s, —C(CH₃)₃), 3.32–3.86 (4H, m, C₂—H, N⫞CH₂—), 5.12 (1H, d, J=5Hz, C₆—H), 5.39–6.00 (5H, m, S⫞CH₂—, C₇—H, —OCH₂O—), 6.59 (1H, s, N⫞H), 8.88 (1H, s, N⫞H), 9.19 (1H, d, J=8Hz, —CONH—) |
| —N(N=N)N—NHCOCH₃ | 165 (decomp.) | 1780, 1750, 1680 | *²,*⁴1.19 (9H, s, —C(CH₃)₃), 2.25 (3H, s, —COCH₃), 3.20–3.65 (4H, m, C₂—H, N⫞CH₂—), 4.91 (1H, d, J=5Hz, C₆—H), 5.20–6.00 (5H, m, S⫞CH₂—, OCH₂O, C₇—H), 6.18 (1H, s, N⫞H) |
| —N(N N)—N | 137–139 (decomp.) | 1770, 1740, 1660 | *²,*⁴1.29 (9H, s, —C(CH₃)₃), 3.24–3.60 (4H, m, C₂—H, N⫞CH₂—), 4.90 (1H, d, J=5Hz, C₆—H), 5.15 |

TABLE 14-continued

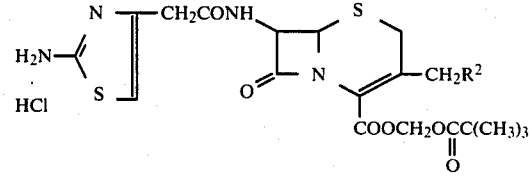

| Compound R² | Melting point (°C.) | IR(KBr) cm⁻¹: ν$_{C=O}$ | NMR(*¹d₆-DMSO, *²CDCl₃, *³D₂O) ppm value: |
|---|---|---|---|
| | | | (1H, m, C₇—H), 5.70–5.95 (4H, m, 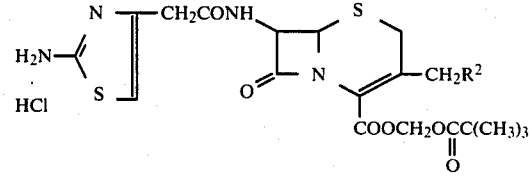, —OCH₂O—), 6.14 (1H, s, ), 7.81 (1H, s, 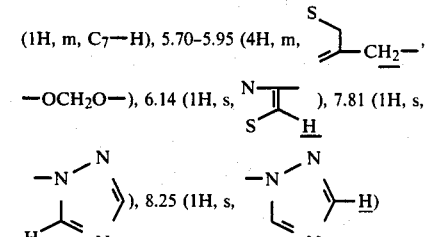), 8.25 (1H, s, 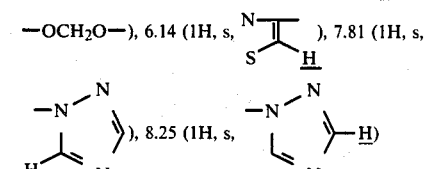) |
| 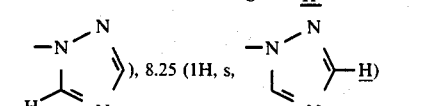 | 120–132 (decomp.) | 1770, 1745, 1660 | *², *⁴1.13 (9H, s, —C(CH₃)₃), 3.16 (2H, s, C₂—H), 3.41 (2H, s, 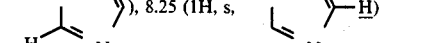), 3.72 (2H, d, J=15Hz, 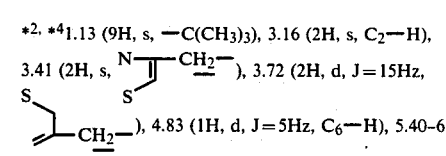), 4.83 (1H, d, J=5Hz, C₆—H), 5.40–6.00 (5H, m, —OCH₂O—, —NH₂, C₇—H), 6.06 (1H, s, 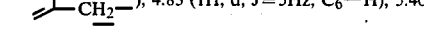), 7.10 (5H, m, 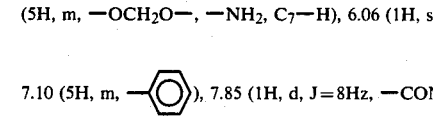), 7.85 (1H, d, J=8Hz, —CONH—) |
| —NHCCH₃<br>‖<br>O | 135–138 (decomp.) | 1778, 1750, 1680, 1620 | *³1.20 (9H, s, —C(CH₃)₃), 2.01 (3H, s, —COCH₃), 3.33–4.38 (6H, m, C₂—H, 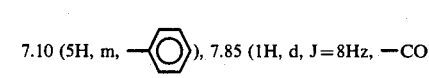, ), 5.09 (1H, d, J=5Hz, C₇—H), 5.64 (1H, d, J=5Hz, C₆—H), 5.81 (2H, bs, —OCH₂O—), 6.64 (1H, s, 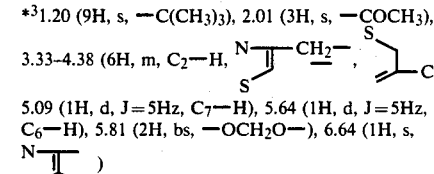) |

Note:
*¹, *² and *³ mean that the respective solvents indicated in the heading were used for measurement of NMR.
*⁴means that the NMR data are concerned with a compound to which HCl is not added.

TABLE 15

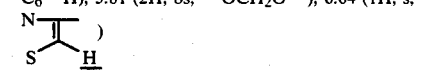

| R¹ | Melting point (°C.) | IR(KBr) cm⁻¹ ν$_{C=O}$ | NMR(d₆-DMSO) ppm value: |
|---|---|---|---|
| —CH₃ | 131–133 (decomp.) | 1780, 1725, 1665 | 2.45 (3H, s, 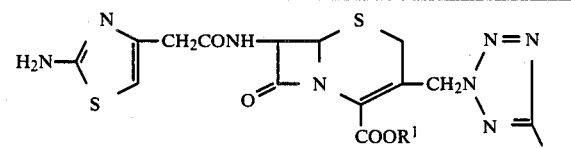—CH₃), 3.40–3.70 (4H, m, 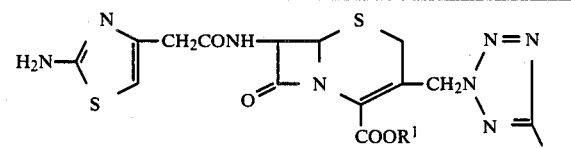, C₂—H), 3.77 (3H, s, —OCH₃), 5.10 (1H, d, J=5Hz, C₆—H), 5.50–5.85 (3H, m, , |

TABLE 15-continued

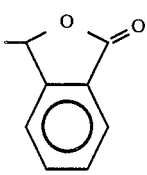

| R¹ | Melting point (°C.) | IR(KBr) cm⁻¹ $\nu_{C=O}$ | NMR(d₆-DMSO) ppm value: |
|---|---|---|---|
| | | | C₇—H), 6.25 (1H, s, [N-S ring with H]), 8.89 (1H, d, J=8Hz, —CONH—) |
| 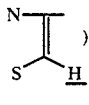 | 152–153 (decomp.) | 1780, 1750, 1680 | 2.42 (3H, s, [N-N ring]—CH₃), 3.45–3.80 (4H, m, [N-S-CH₂—ring], C₂—H), 5.12 (1H, d, J=5Hz, C₆—H), 5.45–5.90 (3H, m, [S ring-CH₂—], C₇—H), 6.60 (1H, [N-S-H ring]), 7.61 (1H, s, [lactone structure]=O), 7.55–8.00 (4H, m, [benzene ring]), 9.25 (1H, d, J=7Hz, —CONH—) |

Note:
*Hydrochloride

EXAMPLE 15

(1) To a suspension of 2.96 g of 7-amino-3-[2-(5-methyl-1,2,3,4-tetrazolyl)methyl]-Δ³-cephem-4-carboxylic acid in 15 ml of N,N-dimethylformamide was added 1.34 g of salicylaldehyde, and the mixture was subjected to reaction at room temperature for 1 hour. The reaction mixture was cooled with ice, and 0.96 g of triethylamine and 2.42 g of pivaloyloxymethyl iodide were added thereto, after which the resulting mixture was subjected to reaction for 20 minutes. After completion of the reaction, the reaction mixture was introduced into a mixed solvent of 150 ml of water and 150 ml of ethyl acetate. After adjusting the pH to 7.3 with sodium hydrogen carbonate, the organic layer was separated, washed with two portions of 100 ml of water, and dried on anhydrous magnesium sulfate. Then, the solvent was removed by distillation under reduced pressure. Isopropyl alcohol was added to the residue, and the resulting crystals were collected by filtration, and then recrystallized from isopropyl alcohol, to obtain 2.73 g (yield 53.1%) of pivaloyloxymethyl 7-(2-hydroxybenzylideneamino)-3-[2-(5-methyl-1,2,3,4-tetrazolyl)methyl]-Δ³-cephem-4-carboxylate having a melting point of 136°–137° C. (decomp.).

IR(KBr) cm⁻¹: $\nu_{C=O}$ 1770, 1765–1750.

NMR(CDCl₃) ppm value: 1.23 (9H, s, —C(CH₃)₃), 2.51 (3H, s, ), 3.30 (2H, s, C₂-H), 5.08 (1H, d, J=5 Hz, C₆-H), 5.32 (1H, d, J=5 Hz, C₇-H), 5.38, 5.82

(2H, ABq, J=16Hz, 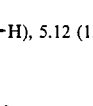), 5.91 (2H, bs, —OCH₂O—), 6.70–7.50

(4H, m, 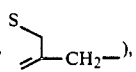), 8.49 (1H, s, —CH=N—).

(2) In a mixed solvent of 50 ml of 4 N hydrochloric acid and 25 ml of diethyl ether, 5.14 g of the pivaloyoxymethyl 7-(2-hydroxy-benzylideneamino)-3-[2-(5-methyl-1,2,3,4-tetrazolyl)methyl]-Δ³-cephem-4-carboxylate obtained in above (1) was stirred for 1 hour at 10°–15° C. Then, the aqueous layer was separated, and washed with two portions of 30 ml of diethyl ether, after which 100 ml of diethyl ether was added to the aqueous layer and the pH thereof was adjusted to 7.0 with 28% by weight aqueous ammonia with ice-cooling. The organic layer was separated and dried on anhydrous magnesium sulfate. Then, a solution of 1 g of dry hydrogen chloride in 20 ml of diethyl ether was added thereto with stirring with ice-cooling, upon which a white colored powder deposited. This was collected by filtration, thoroughly washed with diethyl ether and recrystallized from chloroform, to obtain 3.67 g (yield 82.2%) of hydrochloride of pivaloyloxymethyl 7-amino-3-[2-(5-methyl-1,2,3,4-tetrazolyl)methyl]-$\Delta^3$-cephem-4-carboxylate having a melting point of 149°–151° C. (decomp.).

IR(KBr) cm$^{-1}$: $\nu_{C=O}$ 1773, 1741, 1730.

NMR(d$_6$-DMSO) ppm value: 1.18 (9H, s, —C(CH$_3$)$_3$), 2 44

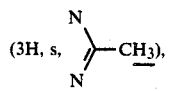

(3H, s, ... —CH$_3$), 3.60 (2H, s, C$_2$-H), 5.23 (2H, s, C$_6$-H, C$_7$-H), 5.62

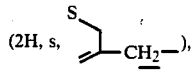

(2H, s, ... —CH$_2$—), 5.78–5.92 (2H, m, —COOCH$_2$O—).

(3) In 20 ml of anhydrous methylene chloride was dissolved 1 g of diketene, and a solution of 0.85 g of chlorine in 9 ml of anhydrous carbon tetrachloride was dropped thereinto at −30° C., after which the mixture was subjected to reaction at −30° C. to −20° C. for 30 minutes. Then, the reaction mixture was dropped at −40° C. into a solution of 4.47 g of the hydrochloride of pivaloyoxymethyl 7-amino-3-[2-(5-methyl-1,2,3,4-tetrazolyl)methyl]-$\Delta^3$-cephem-4-carboxylate obtained in above (2) and 2.43 g of N,N-dimethylaniline in 50 ml of anhydrous methylene chloride. After the dropping, the temperature was slowly elevated and the mixture was subjected to reaction at 0°–5° C. for 1 hour. After completion of the reaction, the solvent was removed by distillation under reduced pressure, and the residue was dissolved in 50 ml of ethyl acetate and 30 ml of water. The organic layer was separated, washed successively with water and saturated aqueous solution of sodium chloride, and dried on anhydrous magnesium sulfate, after which the solvent was removed by distillation under reduced pressure to obtain an oily product. Then, 15 ml of N,N-dimethylformamide was added to dissolve the oily product. To the solution was added 0.76 g of thiourea and the mixture was subjected to reaction at room temperature for 2 hours. After completion of the reaction, the reaction mixture was introduced into a mixed solvent of 150 ml of water and 150 ml of ethyl acetate, and the pH was adjusted to 7.0 with sodium hydrogen carbonate, after which the organic layer was separated, dried on anhydrous magnesium sulfate and then concentrated under reduced pressure until the volume of the organic layer reached 50 ml. Then, a solution of dry hydrogen chloride in diethyl ether was added thereto with stirring with ice-cooling, upon which a white colored powder deposited. This was collected by filtration, thoroughly washed with diethyl ether and recrystallized from ethyl acetate, to obtain 4.4 g (yield 75.0%) of hydrochloride of pivaloyloxymethyl 7-[2-(2-aminothiazol-4-yl)acetamido]-3-[2-(5-methyl-1,2,3,4-tetrazolyl)methyl]-$\Delta^3$-cephem-4-carboxylate having a melting point of 146°–148° C. (decomp.).

The physical properties (IR and NMR) of this compound were identical with those of the product of Example 13.

EXAMPLE 16

(1) By carrying out an acylating reaction in the same manner as in Example 9-(1), the following corresponding compound was obtained:

7-[2-(2-chloroacetamidothiazol-4-yl)acetamido]-3-[(3-chloro-1,2,4-triazolyl)methyl]-$\Delta^3$-cephem-4-carboxylic acid Melting point: 120°–122° C. (decomp.).

IR(KBr) cm$^{-1}$: $\nu_{C=O}$ 1775, 1710, 1680, 1650.

NMR(d$_6$-DMSO) ppm value: 3.43 (2H, s, C$_2$-H), 3.60

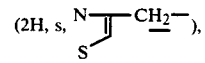

(2H, s, ... —CH$_2$—), 4.32 (2H, s, ClCH$_2$—), 5.09 (1H, d, J=5 Hz, C$_6$-H), 5.05, 5.39

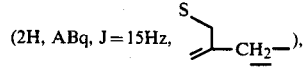

(2H, ABq, J=15Hz, ... —CH$_2$—), 5.68 (1H, dd, J=5 Hz, J=8 Hz, C$_7$-H), 6.97

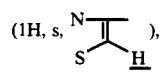

(1H, s, ... H)

8.03

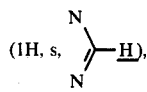

(1H, s, ... H), 8.95 (1H, d, J=8 Hz, —CONH—).

(2) In 40 ml of dry methylene chloride was suspended 2.13 g of the 7-[2-(2-chloroacetamidothiazol-4-yl)acetamido]-3-[(3-chloro-1,2,4-triazolyl)methyl]-$\Delta^3$-cephem-4-carboxylic acid obtained in above (1), and 0.01 g of pyridinium p-toluenesulfonate and 2.88 g of ethyl vinyl ether were added to the suspension, after which the resulting mixture was subjected to reflux to form a solution. Then, the solution was cooled to −75° C., to which 4.48 ml (2.675 millimoles/ml) of a methanolic solution of lithium methoxide was added. After stirring for 5 minutes, 0.52 g of tert.-butyl hypochlorite was added and stirred at that temperature for 15 minutes. Then, 0.48 g of acetic acid was added, and the temperature was elevated to −30° C.

After completion of the reaction, the solvent was removed by distillation under reduced pressure, and 50 ml of ethyl acetate and 40 ml of water were added to the residue thus obtained, after which the pH was adjusted to 0.5 with 2 N hydrochloric acid with ice-cooling. The organic layer was separated and dried on anhydrous magnesium sulfate, and the sblvent was removed by distillation under reduced pressure. Diethyl ether was added to the residue thus obtained and the resulting crystals were collected by filtration, to obtain 1.53 g (yield 68%) of 7$\beta$-[2-(2-chloroactamidothiazol-4-yl)acetamido]-7$\alpha$-methoxy-3-[(3-chloro-1,2,4-triazolyl)- methyl]-Δ³-cephem-4-carboxylic acid having a melting point of 145°–150° C. (decomp.).

IR(KBr) cm⁻¹: $v_{C=O}$ 1775, 1720, 1685, 1635.

NMR(d₆-DMSO) ppm value: 3.34 (2H, s, C₂-H), 3.38 (3H, s, —OCH₃), 3.64

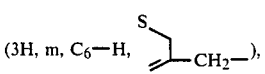

4.31 (2H, s, ClCH₂—), 5.10–5.30

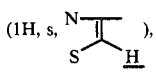

6.91

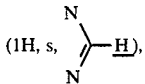

7.96

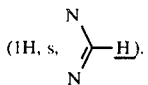

9.25 (1H, s, —CONH—).

(3) In 7 ml of N,N-dimethylacetamide was dissolved 1.40 g of 7β-[2-(2-chloroacetamidothiazol-4-yl)acetamido]-7α-methoxy-3-[(3-chloro-1,2,4-triazolyl)-methyl]-Δ³-cephem-4-carboxylic acid, and 0.3 g of thiourea was added to the solution and reaction was effected at room temperature for 10 hours. After completion of the reaction, 50 ml of diethyl ether was added to the reaction mixture and the supernatant was removed by decantation. Again, 50 ml of diethyl ether was added to the residue and the same procedure as above was repeated. Then, water was added to the residue, and the latter was disintegrated, after which the crystals were collected by filtration and dried, to obtain 0.65 g (yield 50%) of hydrochloride of 7β-[2-(2-aminothiazol-4-yl)acetamino]-7α-methoxy-3-[(3-chloro-1,2,4-triazolyl)-methyl]-Δ³-cephem-4-carboxylic acid having a melting point of 151°–156° C. (decomp.).

IR(KBr) cm⁻¹: $v_{C=O}$ 1765, 1660, 1610.

NMR(d₆-DMSO) ppm value: 3.28 (2H, s, C₂-H), 3.35 (3H, s, —OCH₃), 3.60

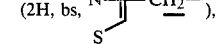

5.05–5.30

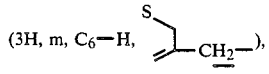

6.82

7.95

EXAMPLE 17

(1) In 16 ml of N,N-dimethylacetamide was dissolved 3.15 g of 2-(2-tert.-amyloxycarboxamidothiazol-4-yl)-2-(syn)-methoxyiminoacetic acid, into which 1.69 g of phosphorus oxychloride was dropped at −20° C. The resulting mixture was stirred at that temperature for 1.5 hours, and then dropped at −30° C. to −20° C. into a solution of 3.16 g of 7-amino-3-[(3-chloro-1,2,4-triazolyl)methyl]-Δ³-cephem-4-carboxylic acid and 6.1 g of N,O-bis(trimethylsilyl)acetamide in 32 ml of anhydrous methylene chloride. After the dropping, the mixture was subjected to reaction at that temperature for 1 hour, then at 0°–10° C. for 30 minutes, and then at room temperature for 30 minutes. After completion of the reaction, the methylene chloride was removed by distillation under reduced pressure, and the residue thus obtained was introduced into a mixed solvent of 80 ml of water and 100 ml of ethyl acetate. The organic layer was thereafter separated, and 80 ml of water was added thereto, after which the pH thereof was adjusted to 7.0 with sodium hydrogen carbonate. The aqueous layer was separated, and 80 ml of ethyl acetate was added thereto, after which the pH was adjusted to 1.5 with 2N hydrochloric acid with ice-cooling. The organic layer was separated, washed successively with 50 ml of water and 50 ml of saturated aqueous solution of sodium chloride and dried on anhydrous magnesium sulfate, after which the solvent was removed by distillation under reduced pressure. Diethyl ether was added to the residue and the resulting crystals were collected by filtration, to obtain 5.62 g (yield 91.8%) of 7-[2-(2-tert.-amyloxycarboxamidothiazol-4-yl)-2-(syn)-methoxyiminoacetamido]-3-[(3-chloro-1,2,4-triazolyl)methyl]-Δ³-cephem-4-carboxylic acid having a melting point of 198°–200° C. (decomp.).

IR(KBr) cm⁻¹: $v_{C=O}$ 1780, 1720, 1670

NMR(d₆-DMSO) ppm value: 0.89 (3H, t, J=7 Hz, —CH₂CH₃), 1.44

1.78 (2H, q, J=7 Hz, —CH₂CH₃), 3.45 (2H, bs, C₂-H), 3.87 (3H, s, —OCH₃), 4.96–5.40

5.82 (1H, dd, J=5 Hz, J=8 Hz, C₇-H), 7.24

8.02

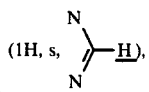

9.61 (1H, d, J=8 Hz, —CONH—), 11.79 (1H, bs, —CONH—).

(2) In 30 ml of trifluoroacetic acid was dissolved 5.62 g of the 7-[2-(2-tert.-amyloxycarboxamidothiazol-4-yl)-2-(syn)-methoxyiminoacetamido]-3-[(3-chloro-1,2,4-triazolyl)methyl]-Δ³-cephem-4-carboxylic acid obtained in above (1), and reaction was effected at room temperature for 30 minutes. After completion of the reaction, the solvent was removed by distillation under reduced pressure. Diethyl ether was added to the residue, and the resulting crystals were collected by filtration, thoroughly washed with diethyl ether and dried, to obtain 5.23 g (yield 93.1%) of trifluoroacetic acid salt of 7-[2-(2-aminothiazol-4-yl)-2-(syn)-methoxyiminoacetamido]-3-[(3-chloro1,2,4-triazolyl)methyl]-Δ³-cephem-4-carboxylic acid having a melting point of 162° C. (decomp.).

IR(KBr) cm⁻¹: $\nu_{C=O}$1778, 1715, 1670, 1630.

NMR(d₆-DMSO) ppm value: 3.48 (2H, bs, C₂-H), 3.93 (3H, s, —OCH ), 4.98–5.42

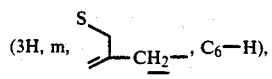

5078 (1H, dd, J=5 Hz, J=8 Hz, C₇-H,

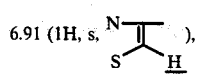

8.02

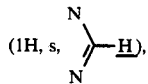

9.74 (1H, d, J=8 Hz, —CONH—).

EXAMPLE 18

(1) In 40 ml of anhydrous methylene chloride was dissolved 3.15 g of 2-(2-tert.-amyloxycarboxamidothiazol-4-yl)-2-(syn)-methoxyiminoacetic acid, and 1.06 g of N-methylmorpholine was added thereto, after which the reaction mixture was cooled to −35° C. Then, 1.12 g of ethyl chlorocarbonate was added thereto and the resulting mixture was subjected to reaction at −35° C. to −25° C. for 1.5 hours, after which 4.62 g of diphenylmethyl 7-amino-3-[2-(5-methyl-1,2,3,4-tetrazolyl)methyl]-Δ³-cephem-4-carboxylate was added to the reaction mixture and the resulting mixture was subjected to reaction at −30° C. to −20° C. for 1 hour. Then, the temperature was slowly elevated, and the reaction was additionally carried out at room temperature for 3 hours. After completion of the reaction, the solvent was removed by distillation under reduced pressure. To the residue were added 50 ml of ethyl acetate and 40 ml of water to dissolve the residue. The organic layer was separated, 40 ml of water was again added, and the pH was adjusted to 1.5 with 2N hydrochloric acid with ice-cooling. Then, the organic layer was separated, and 40 ml of water was added, after which the pH was adjusted to 7.0 with sodium hydrogen carbonate with ice-cooling. The organic layer was separated and dried on anhydrous magnesium sulfate, after which the solvent was removed by distillation under reduced pressure. Diethyl ether was added to the residue, and the resulting crystals were collected by filtration, to obtain 7.06 g (yield 93.0%) of diphenylmethyl 7-[2-(2-tert.amyloxycarboxamidothiazol-4-yl)-2-(syn)-methoxyiminoacetamido]-3-[2-(5-methyl-1,2,3,4-tetrazolyl)methyl]Δ³-cephem-4-carboxylate having a melting point of 94°–99° C. (decomp ).

IR(KBr) cm⁻¹: 1790, 1725, 1685.

NMR(d₆-DMSO) ppm value: 0.87 (3H, t, J=7 Hz, —CH₂C$\underline{H_3}$), 1.44

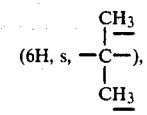

1.75 (2H, q, J=7 Hz, —C$\underline{H_2}$CH₃), 2.4

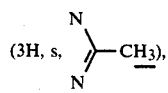

3.46 (2H, bs, C₂-H), 3.81 (3H, s, —OCH₃), 5.15 (1H, d, J=5 Hz, C₆-H), 5.47

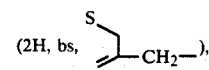

5.86 (1H, dd, J=5 Hz, J=8 Hz, C₇-H), 6.84 (1H, s, >CH—), 6.93–7.52

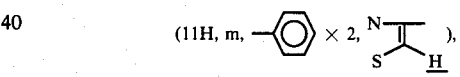

9.61 (1H, d, J=8 Hz, —CONH—), 11.66 (1H, bs, —CONH—).

(2) The compound obtained in above (1) was subjected to reaction and treatment in the same manner as in Example 8-(2) to obtain the following compound: 5.07 g (yield 91.9%) of trifluoroacetic acid salt of 7-[2-(2-aminothiazol-4-yl)-2-(syn)-methoxyiminoacetamido]-3-[2-(5-methyl-1,2,3,4-tetrazolyl)methyl]-Δ³-cephem-4-carboxylic acid Melting point: 123°–125° C. (decomp.).

IR(KBr) cm⁻¹: $\nu_{C=O}$ 1790, 1720–1635.

NMR(CD₃OD) ppm value: 2.45

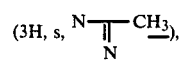

3.44 (2H, bs, C₂-H), 3.99 (3H, s, —OCH₃), 5.10 (1H, d, J=5 Hz, C₆-H), 5.50, 5.81

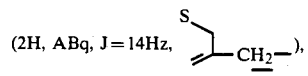

5.80 (1H, d, J=5 Hz, C₇-H), 6.93

(1H, s, 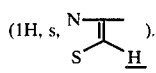).

(3) The compound obtained in above (2) was subjected to reaction and treatment in the same manner as in Example 8-(3) to obtain the following compound: Sodium 7-[2-(2-aminothiazol-4-yl)-2-(syn)-methoxyiminoacetamido]-3-[2-(5-methyl-1,2,3,4-tetrazolyl)-methyl]-Δ³-cephem-4-carboxylate Melting point: 183°–187° C. (decomp.).

IR(KBr) cm⁻¹: 1760, 1665, 1610.

NMR(d₆-DMSO-D₂O) ppm value: 2.50

(3H, s, 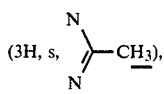), 3.30 (2H, bs, C₂-H), 3.91 (3H, s, —OCH₃), 5.12 (1H, d, J=5 Hz, C₆-H), 5.66

(2H, bs, 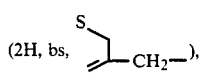), 5.74 (1H, d, J=5 Hz, C₇-H), 6.83

(1H, s, 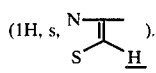).

The following compound was obtained by the same manner.

Sodium 7-[2-(2-aminothiazol-4-yl)-2-(syn)-methoxyiminoacetamido]-3-[(-3-chloro-1,2,4-triazolyl)methyl]-Δ³-cephem-4-carboxylate Melting point: 168° C. (decomp.).

IR(KBr) cm⁻¹: ν_{C=O} 1760, 1670, 1605.

NMR(D₂O) ppm value: 3.30 (2H, bs, C₂-H), 3.97 (3H, s, —OCH₃), 4.93–5.60

(3H, m, 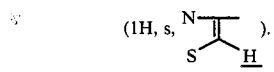, C₆—H), 5,77 (1H, d, J=5 Hz, C₇-H), 6.91

(1H, s, 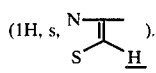), 7.96

(1H, s, 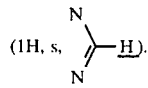).

EXAMPLE 19

In 25 ml of water was suspended 6.13 g of trifluoroacetic acid salt of 7-[2-(2-aminothiazol-4yl) -2-(syn)-methoxyiminoacetamido]-3-[(3-chloro-1,2,4-triazolyl)-methyl]-Δ³-cephem-4-carboxylic acid, and to the suspension was added sodium hydrogen carbonate with ice-cooling to adjust the pH of the suspension to 8.0, upon which the suspension was converted to a solultion. Then, the pH was adjusted to 2.5 with concentrated hydrocholoric acid at the same temperature as above, upon whichg crystals were deposited. The crystals were collected by filtration, thoroughly washed with water and then with acetone, and dried, to obtain 4.71 g (yield 94.5%) of 7-[2-(2-aminothiazol-4-yl)-2-(syn)-methoxyiminoacetamido]-3-[(3-chloro-1,2,4-triazolyl)methyl]-Δ³-cephem-4-carboxylic acid having a melting point of at least 200° C.

IR(KBr) cm⁻¹: ν_{C=O} 1765, 1660, 1625.

NMR(d₆-DMSO) ppm value: 3.44 (2H, bs, C₂-H), 3.85 (3H, s, —OCH₃), 5.20

(2H, bs, 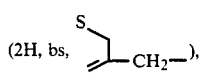), 5.20 (1H, d, J=6 Hz, C₆-H), 5.78 (1H, dd, J=6 Hz, J=8 Hz, C₇-H), 6.71

(1H, s, 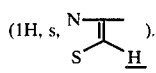), 7.16 (2H, bs, —NH₂), 8.04

(1H, s, 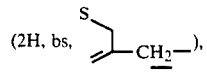), 9.60 (1H, d, J=8 Hz, —CONH—).

In the same manner as above, the following compound was obtained:

7-[2-(2-aminothiazol-4-yl)-2-(syn)-methoxyiminoacetamido]-3-[2-(5-methyl-1,2,3,4-tetrazolyl)methyl]-Δ³-cephem-4-carboxylic acid Melting point: >200° C.

IR(KBr) cm⁻¹: ν_{C=O} 1756, 1660, 1625.

EXAMPLE 20

By carrying out an acylation reaction in the same manner as in Example 17-(1) or Example 18-(1), the compounds shown in Table 16 were obtained.

TABLE 16

Structure: R⁵-thiazole-C(=NOCH₃)-CONH-[β-lactam]-CH₂R² (syn isomer), with COOR¹

| —R¹ | —R² | R⁵— | Melting point (°C.) | IR(KBr) cm⁻¹: $\nu_{C=O}$ |
|---|---|---|---|---|
| —H | -CH₂-(N—N oxadiazole)-SCH₃ | (CH₃)₂(CH₃CH₂)C—OCONH— | 180–183 (decomp.) | 1780, 1710, 1670 |
| —H | —NHCOCH₃ | ClCH₂CONH— | >200 | 1780, 1710, ∫1640 |
| —H | -CH₂-(N—N oxadiazole)-Cl | ClCH₂CONH— | 147–150 (decomp.) | 1780, 1720, ∫1650 |
| —CH(C₆H₅)₂ | -N(N=N tetrazole)-CH₂CH₃ | (CH₃)₂(CH₃CH₂)C—OCONH— | 104–109 (decomp.) | 1780, 1720, 1680 |
| —CH(C₆H₅)₂ | -N(N=N triazole) | (CH₃)₂(CH₃CH₂)C—OCONH— | 130–132 (decomp.) | 1780, 1720, 1680 |
| ″ | —NHCOCH₃ | ″ | 163 (decomp.) | 1780, 1720, 1680 ∫1620 |
| ″ | —NHCO-(2-furyl) | ″ | 165–166 (decomp.) | 1780, 1720, 1680 ∫1620 |
| ″ | -(phenol, -OH) | ″ | 98–105 (decomp.) | 1780, 1723, 1680 |
| ″ | -(phenyl) | ″ | 94–101 (decomp.) | 1775, 1720, 1670 |
| -CH(phthalide) | -N(N=N tetrazole)-CH₃ | ClCH₂CONH— | 156–157 (decomp.) | 1780, 1745, 1680, 1655 |

EXAMPLE 21

By carrying out the reaction and treatment in the same manner as in Example 17 or Example 18, the compounds shown in Table 17 and Table 18 were obtained.

TABLE 17

Trifluoroacetic acid.H₂N—[structure]—CH₂R² (syn isomer)

| Compound R² | Melting point (°C.) | IR(KBr) cm⁻¹: $\nu_{C=0}$ | NMR(d₆-DMSO) ppm value: |
|---|---|---|---|
| [tetrazole-CH₂CH₃] | 153-159 (decomp.) | 1775, 1670, 1630 | 1.27 (3H, t, J=7Hz, —CH₂C$\underline{H_3}$), 2.82 (2H, q, J=7Hz, —C$\underline{H_2}$CH₃), 3,43 (2H, s, C₂—H), 3.85 (3H, s, —OCH₃), 5.13 (1H, d, J=5Hz, C₆—H), 5.5-5.9 (3H, m, [S-CH₂], C₇—H), 6.74 (1H, s, [thiazole-H]), 9.64 (1H, d, J=8Hz, —CONH—) |
| [tetrazole-NHCOCH₃] | 156-159 (decomp.) | 1765, 1700, 1665, 1630 | 2.10 (3H, s, —COCH₃), 3.44 (2H, s, C₂—H), 3.82 (3H, s, —OCH₃), 5.14 (1H, d, J=6Hz, C₆—H), 5.55-5.85 (3H, m, [S-CH₂], C₇—H), 6.72 (1H, s, [thiazole-H]), 9.05 (1H, d, J=8Hz, —CONH—), 11.02 (1H, s, —CONH—) |
| [triazole] | 135 (decomp.) | 1770, 1705, 1665, 1630 | Solvent (CD₃OD) 3.50 (2H, s, C₂—H), 3.98 (3H, s, —OCH₃), 5.00-5.50 (3H, m, [S-CH₂], C₆—H), 5.80 (1H, d, J=5Hz, C₇—H), 7.01 (1H, s, [thiazole-H]), 7.97 (1H, s, [triazole-H]), 8.44 (1H, s, [triazole-H]) |
| [tetrazole] | 142 (decomp.) | 1775, 1660, 1630 | 3.51 (2H, bs, C₂—H), 3.91 (3H, s, —OCH₃), 5.23 (1H, d, J=5Hz, C₆—H), 5.77 (2H, bs, [S-CH₂]), 5.85 (1H, dd, J=5Hz, J=7Hz, C₇—H), 6.85 (1H, s, [thiazole-H]), 7.93 (3H, bs, —$\overset{\oplus}{N}H_3$), 8.95 (1H, s, [amidine-H]), 9.76 (1H, d, J=7Hz, —CONH—) |
| [tetrazole] | 150 (decomp.) | 1775, 1660, 1630 | 3.52 (2H, bs, C₂—H), 3.90 (3H, s, —OCH₃), 5.17 (1H, d, J=5Hz, C₆—H), 5.43 (2H, bs, [S-CH₂]), 5.81 (1H, dd, J=5Hz, J=8Hz, C₇—H), 6.29 (3H, bs, —$\overset{\oplus}{N}H_3$), 6.81 (1H, s, [thiazole-H]), 9.31 (1H, s, [amidine-H]), 9.67 (1H, d, J=8Hz, —CONH—) |
| [tetrazole-NH₂] | 121-125 (decomp.) | 1775, 1670, 1630 | 3.53 (2H, bs, C₂—H), 3.88 (3H, s, —OCH₃), 5.18 (1H, d, J=5Hz, C₆—H), 5.48-5.88 (3H, m, [S-CH₂], C₇—H), 6.83 (1H, s, [thiazole-H]), 9.66 (1H, d, J=8Hz, —CONH—) |

TABLE 17-continued

Trifluoroacetic acid.H$_2$N-[thiazolyl]-C(=N-OCH$_3$)-CONH-[β-lactam]-CH$_2$R$^2$ (syn isomer)

| Compound R$^2$ | Melting point (°C.) | IR(KBr) cm$^{-1}$: $\nu_{C=O}$ | NMR(d$_6$-DMSO) ppm value: |
|---|---|---|---|
| 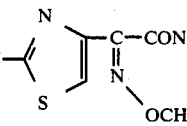 | 181 (decomp.) | 1775, 1710, 1665, 1630 | 2.51 (3H, s, —SCH$_3$), 3.50 (2H, bs, C$_2$—H), 3.93 (3H, s, —OCH$_3$), 4.96–5.34 (3H, m, 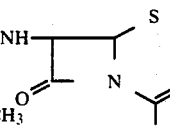, C$_6$—H), 5.80 (1H, dd, J=5Hz, J=8Hz, C$_7$—H), 6.85 (1H, s, 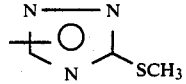), 8.40 (1H, s, 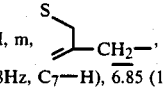), 9.69 (1H, d, J=8Hz, —CONH—) |
| 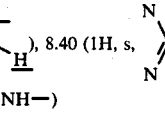 | 168–180 (decomp.) | 1775, 1710, 1680 ∫ 1630 | 2.02 (3H, s, —COCH$_3$), 3.42 (2H, bs, C$_2$—H), 3.86 (3H, s, —OCH$_3$), 4.75–5.55 (3H, m, 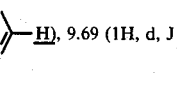, C$_6$—H), 5.68 (1H, dd, J=5Hz, J=8Hz, C$_7$—H), 6.76 (1H, s, 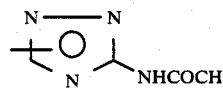), 8.24 (1H, s, 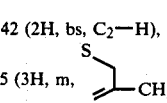), 9.60 (1H, d, J=8Hz, —CONH—) |
| 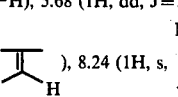 | 141–144 (decomp.) | 1778, 1710, 1670, 1630 | Solvent (CD$_3$OD) 2.39 (3H, s, —CH$_3$), 3.56 (2H, bs, C$_2$—H), 4.03 (3H, s, —OCH$_3$), 4.92–5.37 (3H, m, 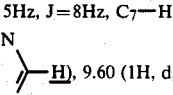, C$_6$—H), 5.86 (1H, d, J=5Hz, C$_7$—H), 7.00 (1H, s, 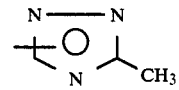), 8.63 (1H, s, 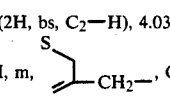) |
| —NHCO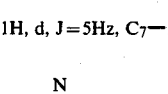 | 183 (decomp.) | 1778, 1710 ∫ 1630 | 3.52 (2H, bs, C$_2$—H), 3.62–4.27 (2H, m, ), 3.88 (3H, s, —OCH$_3$), 5.07 (1H, d, J=5Hz, C$_6$—H), 5.75 (1H, dd, J=5Hz, J=8Hz, C$_7$—H), 6.54 (1H, dd, J=2Hz, J=4Hz, 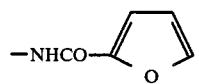), 6.81 (1H, s, 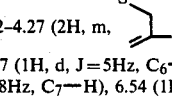), 7.08 (1H, d, J=4Hz, 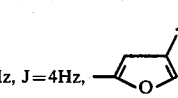), 7.73 (1H, d, J=2Hz, ), 8.25–8.67 (1H, m, —NHCO—), 9.64 (1H, d, J=8Hz, —CONH—) |
| —NHCOCH$_3$ | 166 (decomp.) | 1775, 1710 ∫ 1620 | 1.85 (3H, s, —COCH$_3$), 3.42 (2H, bs, C$_2$—H), 3.86 (3H, s, —OCH$_3$), 3.60–4.21 (2H, m, 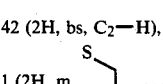), 5.08 (1H, d, J=5Hz, C$_6$—H), 5.67 (1H, dd, J=5Hz, J=8Hz, C$_7$—H), 6.79 (1H, s, 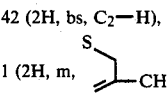), 7.84–8.26 (1H, m, —NHCO—), 9.64 (1H, d, J=8Hz, —CONH—) |

TABLE 17-continued

Trifluoroacetic acid·H$_2$N—[aminothiazole]—C(=N-OCH$_3$)—CONH—[cephem]—CH$_2$R$^2$ (syn isomer)

| Compound R$^2$ | Melting point (°C.) | IR(KBr) cm$^{-1}$: $\nu_{C=O}$ | NMR(d$_6$-DMSO) ppm value: |
|---|---|---|---|
| —NHCO—C$_6$H$_5$ | 137–141 (decomp.) | 1760, 1660, 1630 | 3.51 (2H, bs, C$_2$—H), 3.85 (3H, s, —OCH$_3$), 4.08–4.50 (2H, m, S—CH$_2$—), 5.09 (1H, d, J=5Hz, C$_6$—H), 5.71 (1H, dd, J=5Hz, J=8Hz, C$_7$—H), 6.78 (1H, s, thiazole-H), 7.20–7.98 (5H, m, —C$_6$H$_5$), 8.39–9.34 (4H, m, —$\overset{\oplus}{N}$H$_3$, —NHCO—), 9.59 (1H, d, J=8Hz, —CONH—) |
| —C$_6$H$_5$ | 155–159 (decomp.) | 1770, 1710 f 1620 | 3.09, 3.50 (2H, ABq, J=18Hz, C$_2$—H), 3.50–4.16 (2H, m, S—CH$_2$—), 3.82 (3H, s, —OCH$_3$), 5.10 (1H, d, J=5Hz, C$_6$—H), 5.61 (1H, dd, J=5Hz, J=8Hz, C$_7$—H), 6.73 (1H, s, thiazole-H), 7.19 (5H, bs, —C$_6$H$_5$), 9.57 (1H, d, J=8Hz, —CONH—) |
| —C$_6$H$_4$—OH | 165 (decomp.) | 1770, 1710 f 1630 | 3.05–4.14 (4H, m, C$_2$—H, S—CH$_2$—), 3.82 (3H, s, —OCH$_3$), 5.10 (1H, d, J=5Hz, C$_6$—H), 5.65 (1H, dd, J=5Hz, J=8Hz, C$_7$—H), 6.62, 7.01 (4H, ABq, J=8Hz, —C$_6$H$_4$—O—), 6.75 (1H, s, thiazole-H), 9.55 (1H, d, J=8Hz, —CONH—) |

TABLE 18

Trifluoroacetic acid·H$_2$N—[aminothiazole]—C(=N-OCH$_3$)—CONH—[cephem]—CH$_2$R$^2$ (syn isomer)

| R$^2$ | IR(KBr) cm$^{-1}$: $\nu_{C=O}$ | R$^2$ | IR(KBr) cm$^{-1}$: $\nu_{C=O}$ |
|---|---|---|---|
| —N(N=N)C(CH$_3$)=N (triazole-CH$_3$) | 1770, 1665, 1630 | —N(N=N)N=C(SCH$_3$) (tetrazole-SCH$_3$) | 1770, 1665, 1630 |
| —N(N=N)N=C(CH$_2$COOCH$_2$CH$_3$) | 1770, 1730, 1665, 1630 | —N(N=N)C(SCH$_3$)=N | 1775, 1660, 1630 |

TABLE 18-continued

Trifluoroacetic acid·H₂N— [structure: aminothiazole-oxime-cephem with CH₂R² and COOH]

(syn isomer)

| R² | IR(KBr) cm⁻¹: $\nu_{C=O}$ | R² | IR(KBr) cm⁻¹: $\nu_{C=O}$ |
|---|---|---|---|
| [triazolyl-CH(phenyl)-] | 1770, 1665, 1630 | [pyrazolyl-C(CH₂CH₃)=N-] | 1775, 1665, 1630 |
| [triazolyl-CH(COOCH₂CH₃)-] | 1770, 1730, 1670, 1630 | [oxadiazolyl-C(CN)(phenyl)-] | 1775, 1670, 1630 |
| [triazolyl-C(COOCH₂CH₃)=N-] | 1775, 1740, 1670, 1630 | [2-methylthiophene-5-COOH] | 1770, 1710 f 1620 |
| [oxadiazolinyl-CH(COOCH₂CH₃)-] | 1775, 1725, 1660, 1630 | [2-methylthiophene-5-COOCH₃] | 1770, 1710 f 1620 |
| [triazolyl(COOCH₃)(COOCH₃)-] | 1775, 1730, 1665, 1630 | [2-methylfuran-5-COOH] | 1770, 1710 f 1620 |

EXAMPLE 22

(1) In 25 ml of anhydrous methylene chloride was dissolved 2.2 g of diketene and a solution of 1.85 g of chlorine in 20 ml of anhydrous carbon tetrachloride was dropped into the resulting solution at −30° C. The resulting solution was subjected to reaction at −30° C. to −20° C. for 30 minutes. The reaction was dropped at a temperature of −30° C. or below into a solution of 9.63 g of diphenylmethyl 7-amino-3-[(3-chloro-1,2,4-triazolyl)methyl]-Δ³-cephem-4-carboxylate and 4 g of bis(trimethylsilyl)acetamide in 100 ml of anhydrous methylene chloride, after which the mixture was subjected to reaction at −30° C. to −20° C. for 30 minutes and then at 0°-10° C. for 1 hour. After completion of the reaction, the solvent was removed by distillation under reduced pressure, and the residue obtained was dissolved in 100 ml of ethyl acetate and 80 ml of water. The organic layer was separated, washed successively with 50 ml of water and 50 ml of saturated aqueous solution of sodium chloride and dried on anhydrous magnesium sulfate, after which the solvent was removed by distillation under reduced pressure. Diisopropyl ether was added to the residue, and the resulting crystals were collected by filtration to obtain 10.7 g (yield 89.2%) of diphenylmethyl 7-(4-chloro-3-oxobutyramido)-3-[(3-chloro-1,2,4-triazolyl)-methyl]-Δ³-cephem-4-carboxylate having a melting point of 73°–75° C.

IR(KBr) cm⁻¹: $\nu_{C=O}$ 1780, 1725, 1690–1650.

NMR(CDCl₃-D₂O) ppm value: 3.19 (2H, bs, C₂-H), 3.50 (2H, s, —COCH₂CO—), 4.12 (2H, s, ClCH₂—), 4.88 (1H, d, J=5 Hz, C₆-H), 4.82, 5.35

(2H, ABq, J=15Hz, 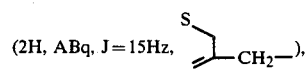), 5.72 (1H, d, J=5 Hz, C₇-H), 6.90 (1H, s, >CH—), 7.26

(10H, s, 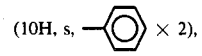 × 2), 7.71

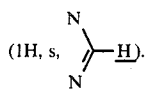 (1H, s, ).

(2) In 40 ml of acetic acid was dissolved 6 g of diphenylmethyl 7-(4-chloro-3-oxobutyramido)-3-[(3-chloro-1,2,4-triazolyl)methyl]-Δ³-cephem-4-carboxylate, and a solution of 1 g of sodium nitrite in 6 ml of water was dropped into the resulting solution over a period of 1 hour with ice-cooling. Then, the mixture was subjected to reaction at room temperature for 2 hours. After completion of the reaction, the reaction mixture was introduced into 600 ml of water to deposit crystals, which were collected by filtration, thoroughly washed with water and dried, to obtain 5.24 g (yield 83.3%) of diphenylmethyl 7-(4-chloro-2-hydroxyimino-3-oxobutyramido)-3-[(3-chloro-1,2,4-triazolyl)methyl]-Δ³-cephem-4-carboxylate having a melting point of 93°-95° C. (decomp.).

IR(KBr) cm⁻¹: 1780, 1720, 1700–1650.

NMR(CDCl₃-D₂O) ppm value: 3.20 (2H, bs, C₂-H), 4.59 (2H, s, ClCH₂—), 4.93 (1H, d, J=5 Hz, C₆-H), 4.79, 5.16

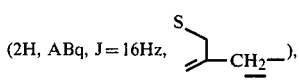

5.78 (1H, d, J=5 Hz, C₇-H), 6.90 (1H, s, >CH—), b 7.24

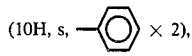

7.71

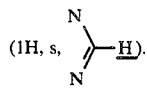 (1H, s, ).

(3) In 35 ml of N,N-dimethylformamide was dissolved 6.29 g of diphenylmethyl 7-(4-chloro-2-hydroxyimino-3-oxobutyramido)-3[(3-chloro-1,2,4-triazolyl)methyl]-Δ³-cephem-4-carboxylate. While cooling the solution with ice, 1.5 g of sodium carbonate and 2.1 g of dimethyl sulfate were added thereto, and then the mixture was subjected to reaction at 5°-10° C. for 1 hour. After completion of the reaction, the reaction mixture was introduced into 600 ml of water to deposit crystals, which were collected by filtration and purified by a column chromatography (Wako silica gel C-200; developing solvent, benzene:ethyl acetate=9:1), to obtain 2.7 g (yield 42%) of diphenylmethyl 7-(4-chloro-2-(syn)methoxyimino-3-oxobutyramido)-3-[(3-chloro-1,2,4-triazolyl)methyl]-Δ³-cephem-4-carboxylate having a melting point of 102°-104° C. (decomp.).

IR(KBr) cm⁻¹: νC=O 1782, 1720, 1690, 1670. NMR(CDCl₃-D₂O) ppm value: 3.20 (2H, bs, C₂-H), 4.05 (3H, s, —OCH₃), 4.50 (2H, s, ClCH₂—), 4.95 (1H, d, J=5 Hz, C₆-H), 4.82, 5.36

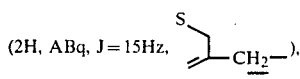

5.85 (1H, d, J=5 Hz, C₇-H), 6.95 (1H, s, >CH—), 7.35

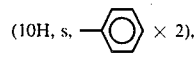

7.72

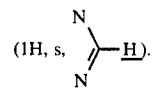 (1H, s, ).

(4) In 48 ml of N,N-dimethylacetamide were dissolved 6.43 g of diphenylmethyl 7-(4-chloro-2-(syn)methoxyimino-3-oxobutyramido)-3-[(3-chloro-1,2,4-triazolyl)methyl]-Δ³-cephem-4-carboxylate and 1 g of thiourea, and the resulting solution was subjected to reaction at room temperature for 2 hours. After completion of the reaction, the reaction mixture was introduced into a mixed solvent of 600 ml of water and 600 ml of ethyl acetate. Then, the pH thereof was adjusted to 6.7 with sodium hydrogen carbonate, and the organic layer was separated. The aqueous layer was additionally extracted with two portions of 300 ml of ethyl acetate. The organic layer were combined, washed with two portions of 800 ml of water and dried on anhydrous magnesium sulfate, after which the solvent was removed by distillation under reduced pressure. Diethyl ether was added to the residue, and the resulting crystals were collected by filtration, to obtain 5.87 g (yield 88%) of diphenylmethyl 7-[2-(2-aminothiazol-4-yl)-2-(syn)-methoxyiminoacetamido]-3[(3-chloro-1,2,4-triazolyl)methyl]-Δ³-cephem-4-carboxylate having a melting point of 155°-157° C. (decomp.).

IR(KBr) cm⁻¹: νC=O 1781, 1725, 1672. NMR(CDCl₃-D₂O) ppm value: 3.20 (2H, bs, C₂-H), 3.86 (3H, s, —OCH₃), 4.99 (1H, d, J=5 Hz, C₆-H), 4.82, 5.41

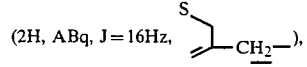

5.96 (1H, d, J=5 Hz, C₇-H), 6.62

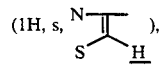

6.92 (1H, s, >CH—), 7.28

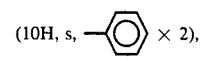

7.71

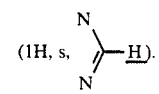 (1H, s, ).

(5) In a mixed solvent of 35 ml of trifluoroacetic acid and 10 ml of anisole was dissolved 6.65 g of diphenylmethyl 7-[2-(2-aminothiazol-4-yl)-2-(syn)methoxyiminoacetamido]-3-[(3-chloro-1,2,4-triazolyl)methyl]-Δ³-cephem-4-carboxylate, and the resulting solution was subjected to reaction at room temperature for 1 hour. After completion of the reaction, the solvent was removed by distillation under reduced pressure, and diethyl ether was added to the residue, after which the resulting crystals were collected by filtration, thoroughly washed with diethyl ether and dried to obtain 5.71 g (yield 93.2%) of trifluoroacetic acid salt of 7-[2-(2-aminothiazol-4-yl)-2-(syn)-methoxyiminoacetamido]-3-(3-chloro-1,2,4-triazolyl)methyl-Δ³-cephem-4-carboxylic acid having a melting point of 162° C. (decomp.).

The physical properties (IR and NMR data) of this compound were identical with those of the product obtained in Example 17-(2).

EXAMPLE 23

In 50 ml of anhydrous tetrahydrofuran were dissolved 2.24 g of 4-bromo-3-oxo-2-methoxyiminobutyric acid, 2.0 g of 1-oxybenztriazole and 4.62 g of diphenylmethyl 7-amino-3-[(3-chloro-1,2,4-triazolyl)methyl]-Δ³-cephem-4-carboxylate, and the solution was cooled to 5° C. Then, 2.5 g of N,N'-dicyclohexylcarbodiimide was added, and the resulting mixture was subjected to reaction at the same temperature for 30 minutes and then at room temperature for 5 hours. After completion of the reaction, the insoluble matter was removed by filtration and the solvent was removed from the filtrate by distillation under reduced pressure. To the residue was added 40 ml of ethyl acetate, and a small quantity of insoluble matter was removed by filtration, after which the ethyl acetate solution was washed successively with 5% by weight aqueous solution of sodium hydrogen carbonate and water, and dried on anhydrous magnesium sulfate. The solvent was then removed by distillation under reduced pressure. The residue thus obtained was purified by a column chromatography (Wako silica gel C-200; developing solvent, benzene:ethyl acetate=9:1) to obtain 3.65 g (yield 54.6%) of diphenylmethyl 7-(4-bromo-2-methoxyimino-3-oxobutyramido)-3-(3-chloro-1,2,4-triazolyl)methyl-Δ³-cephem-4-carboxylate having a melting point of 91°–94° C. (decomp.).

IR(KBr) cm⁻¹: $\nu_{C=O}$ 1780, 1720, 1680.

NMR(d₆-DMSO) ppm value: 3.55 (2H, bs, C₂-H), 3.84 (3H, s, —OCH₃), 4.16 (2H, s, BrCH₂—), 4.99–5.53

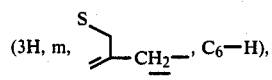

(3H, m, C₆—H), 5.87 (1H, dd, J=5 Hz, J=8 Hz, C₇-H), 7.06 (1H, s, >CH—), 7.40

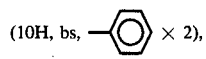

(10H, bs, —⌬ × 2), 8.04

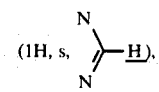

(1H, s, N⟩—H), 10.01 (1H, d, J=8 Hz, —CONH—).

In the same manner as above, the following compound was obtained:

Diphenylmethyl 7-(4-bromo-2-methoxyimino-3-oxobutyramido)-3-[2-(5-methyl-1,2,3,4-tetrazolyl)methyl]-Δ³-cephem-4-carboxylate Melting point: 80°–82° C. (decomp.)

IR(KBr) cm⁻¹: $\nu_{C=O}$ 1780, 1720, 1680.

NMR(CDCl₃) ppm value: 2.41

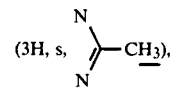

(3H, s, N⟩—CH₃), 3.16 (2H, bs, C₂-H), 4.00 (3H, s, —OCH₃), 4.25 (2H, s, BrCH₂—), 4.88 (1H, d, J=5 Hz, C₆-H), 5.38

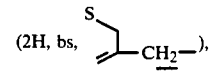

(2H, bs, S⟩—CH₂—), 5.78 (1H, dd, J=5 Hz, J=8 Hz, C₇-H), 6.81 (1H, s, >CH—), 7.18

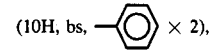

(10H, bs, —⌬ × 2), 9.10 (1H, d, J=8 Hz, —CONH—).

EXAMPLE 24

In 50 ml of anhydrous tetrahydrofuran were dissolved 1.45 g of 3-oxo-2-methoxyiminobutyric acid, 2.0 g of 1-oxybenztriazole and 4.62 g of diphenylmethyl 7-amino-3-[(3-chloro-1,2,4-triazolyl)methyl]-Δ³-cephem-4-carboxylate and the solution was cooled to 5° C. Then, 2.5 g of N,N'-dicyclohexylcarbodiimide was added thereto and the resulting mixture was subjected to reaction at the same temperature for 30 minutes and then at room temperature for 5 hours. After completion of the reaction, the insoluble matter was removed by filtration, and the solvent was removed from the filtrate by distillation under reduced pressure. To the residue was added 40 ml of ethyl acetate, and a small quantity of insoluble matter was removed by filtration, after which the filtrate was washed successively with 5% by weight aqueous solution of sodium hydrogen carbonate and water, and dried on anhydrous magnesium sulfate. The solvent was removed by distillation under reduced pressure. The residue thus obtained was purified by a column chromatography (Wako silica gel C-200; developing solvent, benzene:ethyl acetate=8:1) to obtain 3.7 g (yield 62.8%) of diphenylmethyl 7-(2-methoxyimino-3-oxobutyramido)-3-[(3-chloro-1,2,4-triazolyl)methyl]-Δ³-cephem-4-carboxylate having a melting point of 102°–103° C. (decomp.).

IR(KBr) cm⁻¹: $\nu_{C=O}$ 1775, 1740, 1670. NMR(d₆-DMSO) ppm value: 2.31 (3H, s, —COCH₃), 3.47 (2H, bs, C₂-H), 4.00 (3H, s, —OCH₃), 4.90–5.40

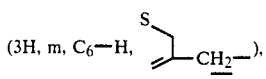

5.89 (1H, dd, J=8 Hz, J=5 Hz, C₇-H), 6.93 (1H, s, —CH<), 7.30

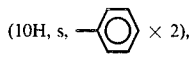

7.95

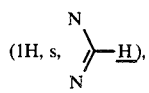

9.43 (1H, d, J=8 Hz, —CONH—).

In the same manner as above, the following compound was obtained:
Diphenylmethyl 7-(2-methoxyimino-3-oxobutyramido)-3-[2-(5-methyl-1,2,3,4-tetrazolyl)methyl]-Δ³-cephem-4-carboxylate.

Melting point: 88°–90° C. (decomp.). IR(KBr) cm⁻¹: $\nu_{C=O}$ 1775, 1720, 1685, 1670.

NMR(d₆-DMSO) ppm value: 2.27 (3H, s, —COCH₃), 2.37

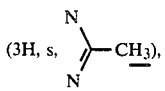

3.46 (2H, bs, C₂-H), 3.93 (3H, s, —OCH₃), 5.10 (2H, d, J=5 Hz, C₆-H), 5.42

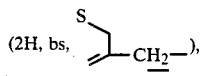

5.82 (1H, dd, J=5 Hz, J=8 Hz, C₇-H), 6.82 (1H, s, >CH—), 7.17

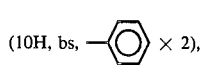

9.27 (1H, d, J=8 Hz, —CONH—).

EXAMPLE 25

(1) In 90 ml of anhydrous methylene chloride was suspended 2.96 g of 7-amino-3-[(3-chloro-1,2,4-trizaolyl)methyl]-Δ³-cephem-4-carboxylic acid and 2.02 g of triethylamine and 1.7 of diketene were added to the suspension with ice-cooling, after which the mixture was subjected to reaction at 5°–10° C. for 4 hours. After completion of the reaction, 100 ml of water was added to the reaction mixture, and the aqueous layer was separated. Then, 100 ml of ethyl acetate was added to the aqueous layer, and the pH thereof was adjusted to 1.0 with 2N hydrochloric acid. After removing a slight quantity of insoluble matter, the organic layer was separated and dried on anhydrous magnesium sulfate. With stirring, about 1.6 g of diphenyldiazomethane was slowly added thereto and the resulting mixture was subjected to reaction for about 30 minutes. After completion of the reaction, the solvent was removed by distillation under reduced pressure. Isopropyl ether was added to the residue, and the resulting crystals were collected by filtration, thoroughly washed with isopropyl ether and then dried to obtain 3.3 g (yield 60.4%) of diphenylmethyl 7-(3-oxobutyramido)-3-[(3-chloro-1,2,4-triazolyl)methyl]-Δ³-cephem-4-carboxylate having a melting point of 75°–77° C. (decomp.).

IR(KBr) cm⁻¹: $\nu_{C=O}$ 1775, 1720, 1670.

NMR(d₆-DMSO) ppm value: 2.17 (3H, s, —COCH₃), 3.48 (4H, bs, C₂-H, —COCH₂CO—), 5.00–5.40

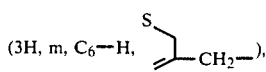

5.86 (1H, dd, J=8 Hz, J=5 Hz, C₇-H), 6.99 (1H, s, —CH<), 7.36

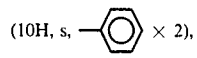

8.03

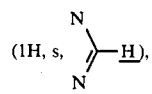

9.12 (1H, d, J=8 Hz, —CONH—).

In the same manner as above, the following compound was obtained:
Diphenylmethyl 7-(3-oxobutyramido)-3-[2-(5-methyl-1,2,3,4-tetrazolyl)methyl]-Δ³-cephem-4-carboxylate.

Melting point: 84°–86° C. (decomp.).

IR(KBr) cm⁻¹: $\nu_{C=O}$ 1780, 1720, 1670.

NMR(d₆-DMSO) ppm value: 2.06 (3H, s, —COCH ), 2.31

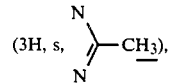

3.34 (2H, s, —COCH₂CO—), 3.46 (2H, bs, C₂-H), 5.00 (1H, d, J=5 Hz, C₆-H), 5.31

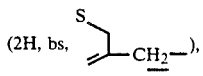

5.63 (1H, dd, J=5 Hz, J=8 Hz, C₇-H), 6.71 (1H, s, >CH—), 7.06

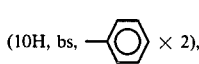

8.75 (1H, d, J=8 Hz, —CONH—).

(3) The diphenylmethyl 7-(3-oxobutyramido)-3-[(3-chloro-1,2,4-triazolyl)methyl]-Δ³-cephem-4-carboxylate obtained in above (1) was subjected to reaction and treatment in the same manner as in Example 22-(2) to obtain diphenylmethyl 7-(2-hydroxyimino-3-oxobutyramido)-[3-(3-chloro-1,2,4-triazolyl)methyl]-Δ³-cephem-4-carboxylate having a melting point of 108°–110° C. (decomp.).

IR(KBr) cm⁻¹: $\nu_{C=O}$ 1780, 1720, 1680.

NMR(d$_6$-DMSO) ppm value: 2.32 (3H, s, —COCH$_3$), 3.44 (2H, bs, C$_2$-H), 4.90–5.40

(3H, m, C$_6$—H, [thiazine-CH$_2$—]), 5.88 (1H, dd, J=8 Hz, J=5 Hz, C$_7$-H), 6.94 (1H, s, —CH<), 7.33

(10H, s, —[phenyl] × 2), 8.00

(1H, s, [triazole N=N—H]), 9.30 (1H, d, J=8 Hz, —CONH—), 12.82 (1H, s, =N—OH).

In the same manner as above, the following compound was obtained:
Diphenylmethyl 7-(2-hydroxyimino-3-oxobutyramido)-3[-2-(5-methyl-1,2,3,4-tetrazolyl)methyl]-Δ$^3$-cephem-4-carboxylate.
Melting point: 102°–105° C. (decomp.).
IR(KBr) cm$^{-1}$: ν$_{C=O}$ 1780, 1720, 1680.
NMR(d$_6$-DMSO) ppm value: 2.25 (3H, s, —COCH$_3$), 2.35

(3H, s, [tetrazole]—CH$_3$), 3.44 (2H, bs, C$_2$-H), 5.05 (1H, d, J=5 Hz, C$_6$-H), 5.37

(2H, bs, [thiazine-CH$_2$—]), 5.76 (1H, dd, J=5 Hz, J=8 Hz, C$_7$-H), 6.71 (1H, s, >CH—), 7.11

(10H, bs, —[phenyl] × 2), 9.04 (1H, d, J=8 Hz, —CONH—).

(3) The diphenylmethyl 7-(2-hydroxyimino-3-oxobutyramido)-3-[(3-chloro-1,2,4-triazolyl)methyl]-Δ$^3$-cephem-4-carboxylate and diphenylmethyl 7-(2-hydroxyimino-3-oxobutyramido)-3-[2-(5-methyl-1,2,3,4-tetrazolyl)methyl] -Δ$^3$-cephem-4-carboxylate obtained in above (2) was subjected to reaction and treatment in the same manner as in Example 22-(3) to obtain diphenylmethyl 7-(2-methoxyimino-3-oxobutyramido)-3-[(3-chloro-1,2,4-triazolyl)methyl]-Δ$^3$-cephem-4-carboxylate having a melting point of 102°–103° C. (decomp.) and diphenylmethyl 7-(2-methoxyimino-3-oxobutyramido)-3-[2-(5-methyl-1,2,3,4-tetrazolyl)methyl]-Δ$^3$-cephem-4-carboxylate having a melting point of 88°–90° C. (decomp.).

The physical properties (IR and NMR) of these compounds were identical with those of the compounds obtained in Example 24.

EXAMPLE 26

In 120 ml of dry tetrahydrofuran was dissolved 5.89 g of diphenylmethyl 7-(2-methoxyimino-3-oxobutyramido)-3-[2-(5-methyl-1,2,3,4-tetrazolyl)methyl]-Δ$^3$-cephem-4-carboxylate, and thereto was added 1.34 g of alumimum chloride. To the solution was added to 5.00 g of pyridinium hydrobromide perbromide at room temperature, and the resulting mixture was stirred at said temperature for 30 minutes. After completion of the reaction, the solvent was removed by distillation under reduced pressure, and to the residue were added 50 ml of ethyl acetate and 50 ml of water. A small amount of insoluble matter was removed by filtration, and the organic layer was separated, washed with water, and dried on anhydrous magnesium sulfate, after which the solvent was removed by distillation under reduced pressure. The residue thus obtained was purified by a column chromatography (Wako silica gel C-200; developing solvent, benzene:ethyl acetate=9:1), to obtain 4.13 g (yield 61.8%) of diphenylmethyl 7-[4-bromo-2-methoxyimino-3-oxobutyramido]-3-[2-(5-methyl-1,2,3,4-tetrazolyl)methyl]-Δ$^3$-cephem-4-carboxylate having a melting point of 80°–82° C. (decomp.).

EXAMPLE 27

By subjecting various starting compounds to the same reaction as in Example 22, the corresponding objective compounds shown in Table 19 were obtained.

The physical properties of these compounds were identical with those of the compounds produced in Example 21.

TABLE 19

Trifluoroacetic acid·H$_2$N—[thiazole]—C(=N—OCH$_3$)—CONH—[cephem]—CH$_2$R$^2$, COOH (syn isomer)

| R$^2$ | R$^2$ | R$^2$ |
|---|---|---|
| —N[tetrazole with CH$_3$]  N=N | —N[tetrazole with CH$_2$CH$_3$]  N=N | —N[tetrazole]  N=N |

TABLE 19-continued
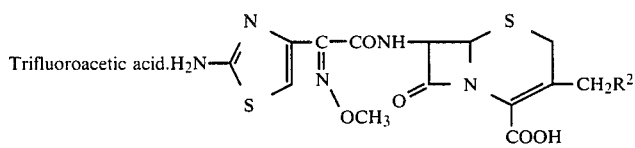
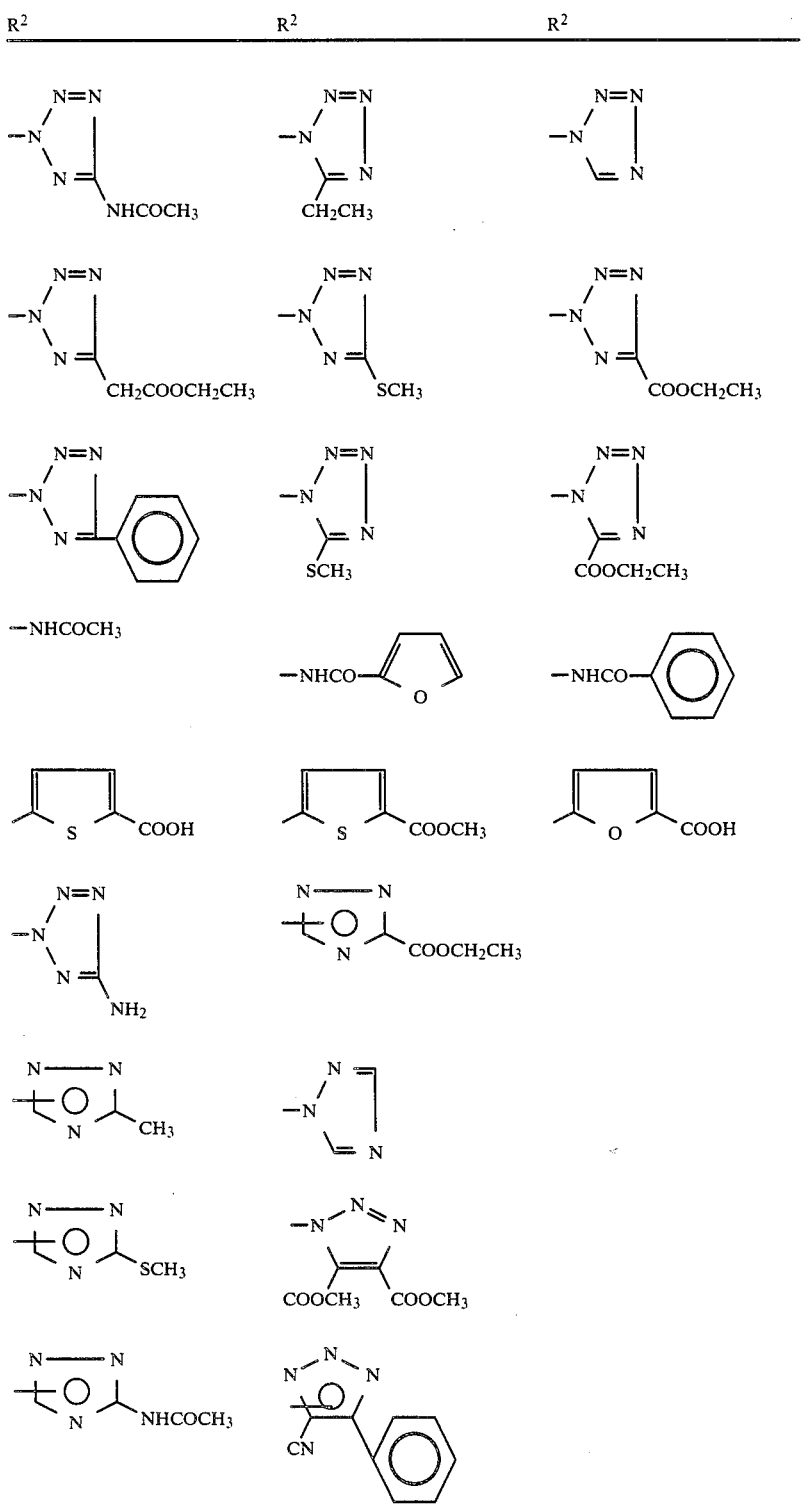

TABLE 19-continued

Trifluoroacetic acid.H₂N— [structure: aminothiazole-C(=N-OCH₃)-CONH-cephem with CH₂R² and COOH, syn isomer]

(syn isomer)

| R² | R² | R² |
|---|---|---|
| —⟨phenyl⟩—OH | —⟨phenyl⟩ | |

EXAMPLE 28

(1) In 40 ml of acetic acid was dissolved 6.25 g of diphenylmethyl 7-(4-bromo-3-oxobutyramido)-3-[2-(5-methyl-1,2,3,4-tetrazolyl)methyl]-$\Delta^3$-cephem-4-carboxylate obtained in Example 12-(1), and to the solution was dropwise added a solution of 1 g of sodium nitrite in 6 ml of water with ice-cooling over a period of 1 hour. Then, the mixture was subjected to reaction at room temperature for 2 hours. After completion of the reaction, the reaction mixture was introduced into 600 ml of water to deposit crystals, which were collected by filtration, thoroughly washed with water and dried to obtain 5.43 g (yield 83.0%) of diphenylmethyl 7-(4-bromo-2-hydroxyimino-3-oxobutyramido)-3-[2-(5-methyl-1,2,3,4-tetrazolyl)methyl]-$\Delta^3$-cephem-4-carboxylate having a melting point of 97°–100° C.

IR(KBr) cm⁻¹: $\nu_{C=O}$ 1780, 1720, 1695–1650.

NMR(CDCl₃) ppm value: 2.49

(3H, s, [N=C(CH₃)–N tetrazole methyl]), 3.23 (2H, s, C₂-H), 4.42 (2H, s, BrCH₂-), 4.92 (1H, d, J=5 Hz, C₆-H), 5.32, 5.70

(2H, ABq, J=16Hz, [S–CH₂–]), 5.78 (1H, d, J=5 Hz, C₇-H), 6.89 (1H, s, >CH—), 7.23

(10H, s, —⟨phenyl⟩ × 2), 9.10 (1H, d, J=8 Hz, —CONH—).

(2) In 35 ml of N,N-dimethylacetamide were dissolved 6.54 g of diphenylmethyl 7-(4-bromo-2-hydroxyimino-3-oxobutyramido)-3-[2-(5-methyl-1,2,3,4-tetrazolyl)methyl]-$\Delta^3$-cephem-4-carboxylate and 1 g of thiourea, and the solution was subjected to reaction at room temperature for 2 hours. After completion of the reaction, the reaction mixture was introduced into a mixed solvent of 500 ml of water and 500 ml of ethyl acetate. Then, the pH of the mixture was adjusted to 7.0 with sodium carbonate, and the organic layer was separated. The aqueous layer was additionally extracted with two portions of 200 ml of ethyl acetate. The organic layers were combined and dried on anhydrous magnesium sulfate, after which the solvent was removed by distillation under reduced pressure. The residue was purified by a column chromatography (Wako silica gel C-200; developing solvent, chloroform:methanol=20:1) to obtain 3.2 g (yield 50.7%) of diphenylmethyl 7-[2-(2-aminothiazol-4-yl)-2-(syn)-hydroxyiminoacetamido]-3-[2-(5-methyl-1,2,3,4-tetrazolyl)methyl]-$\Delta^3$-cephem-4-carboxylate having a melting point of 164° C. (decomp.).

IR(KBr) cm⁻¹: $\nu_{C=O}$ 1780, 1730, 1670.

NMR(d₆DMSO) ppm value:

2.40

(3H, s, [N=C(CH₃)–N tetrazole methyl]), 3.41 (2H, bs, C₂-H), 5.14 (1H, d, J=5 Hz, C₆-H), 5.20–6.10

(3H, m, [S–CH₂–], C₇-H), 6.63

(1H, s, [N=C(H)–S aminothiazole]), 6.90 (1H, s, >CH—), 7.28

(10H, s, —⟨phenyl⟩ × 2), 9.46 (1H, d, J=8 Hz, —CONH—).

(3) In a mixed solvent of 32 ml of trifluoroacetic acid and 10 ml of anisole was dissolved 6.31 g of diphenylmethyl 7-[2-(2-aminothiazol-4-yl)-2-(syn)-hydroxyiminoacetamido]-3-[2-(5-methyl-1,2,3,4-tetrazolyl)methyl]-$\Delta^3$-cephem-4-carboxylate, and the solution was subjected to reaction at room temperature for 1.5 hours. After completion of the reaction, the solvent was removed by distillation under reduced pressure, and diethyl ether was added to the residue. The resulting crystals were collected by filtration, thoroughly washed with diethyl ether and dried to obtain 5.33 g (yield 92.1%) of trifluoroacetic acid salt of 7-[2-(2-aminothiazol-4-yl)-2-(syn)-hydroxyiminoacetamido]-3-

[2-(5-methyl-1,2,3,4tetrazolyl)methyl]-Δ³-cephem-4-carboxylic acid having a melting point of 175° C. (decomp.).

IR(KBr) cm⁻¹: ν_{C=O} 1770, 1680–1630.
NMR(d₆-DMSO) ppm value: 2.43

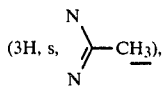

3.41 (2H, bs, C₂-H), 5.13 (1H, d, J=5 Hz, C₆-H), 5.26–5.95

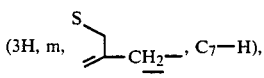

6.67

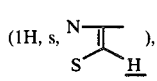

9.48 (1H, d, J=8 Hz, —CONH—).

In the same manner as above, the following compounds were obtained:

Trifluoroacetic acid salt of 7-[2-(2-aminothiazol-4-yl)-2-(syn)-hydroxyiminoacetamido]-3-benzyl-Δ³-cephem-4-carboxylic acid Melting point: 139° C. (decomp.).
IR(KBr) cm⁻¹: ν_{C=O} 1760, 1710, 1660.
NMR(d₆-DMSO) ppm value: 3.40 (2H, bs, C₂-H), 3.89

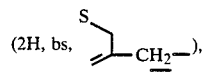

5.18 (1H, d, J=4 Hz, C₆-H), 5.50–5.84 (1H, m, C₇-H), 6.89

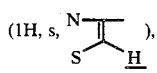

7.25

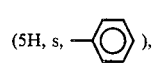

8.20–9.95 (4H, m, —N⊕H₃, —CONH—).

Trifluoroacetic acid salt of 7-[2-(2-aminothiazol-4-yl)-2-(syn)-hydroxyiminoacetamido]-3-acetamidomethyl-Δ³-cephem-4-carboxylic acid IR(KBr) cm⁻¹: ν_{C=O} 1775, 1710–1620.

(4) The trifluoroacetic acid salt of 7-[2-(2-aminothiazol-4-yl)-2-(syn)-hydroxyiminoacetamido]-3-acetamidomethyl-Δ³-cephem-4-carboxylic acid obtained in above (3) was subjected to reaction and treatment in the same manner as in Example 8-(3) to obtain the following compound:

Sodium 7-[2-(2-aminothiazol-4-yl)-2-(syn)-hydroxyiminoacetamido]-3-acetamidomethyl-Δ³-cephem-4-carboxylate Melting point: >200° C.
IR(KBr) cm⁻¹: ν_{C=O} 1750, 1680, 1665, 1605.

NMR(D₂O) ppm value: 1.98 (3H, s —COCH₃), 3.29, 3.62 (2H, ABq, J=18 Hz, C₂-H), 3.86, 4.20

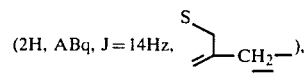

5.11 (1H, d, J=5 Hz, C₆-H, 5.76 (1H, d, J=5 Hz, C₇-H), 6.84

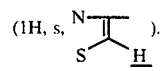

EXAMPLE 29

(1) In 13 ml of N,N-dimethylacetamide was dissolved 2.49 g of 2-(2-chloroacetamidothiazol-4-yl)glyoxylic acid, and to the solution was dropwise added 3.07 g of phosphorus oxychloride at −20° C. The resulting mixture was subjected to reaction at −20° C. to −10° C. for 1 hour, and 4.62 g of diphenylmethyl 7-amino-3-[2-(5-methyl-1,2,3,4-tetrazolyl)methyl]-Δ³-cephem-4-carboxylate was added. The resulting mixture was subjected to reaction at −20° C. to −10° C. for 30 minutes and then at room temperature for 30 minutes. After completion of the reaction, the reaction mixture was introduced into a mixed solvent of 40 ml of water and 60 ml of ethyl acetate. Then, the pH thereof was adjusted to 7.0 with sodium hydrogen carbonate, and the organic layer was separated, washed with 30 ml of water and dried on anhydrous magnesium sulfate. The solvent was removed by distillation under reduced pressure, and diethyl ether was added to the resulting residue, after which the resulting crystals were collected by filtration, to obtain 6.35 g (yield 91.6%) of diphenylmethyl 7-[2-(2-chloroacetamidothiazol-4-yl)glyoxylamido]-3-[2-(5-methyl-1,2,3,4-tetrazolyl)methyl]-Δ³-cephem-4-carboxylate having a melting point of 115°–119° C.

IR(KBr) cm⁻¹: ν_{C=O} 1780, 1720, 1670.
NMR(d₆-DMSO) ppm value: 2.46 (3H, s, —CH₃), 3.62 (2H, bs, C₂-H), 4.47 (2H, s, ClCH₂—), 5.37 (1H, d, J=5 Hz, C₆-H), 5.63

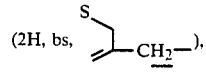

6.06 (1H, dd, J=5 Hz, J=8 Hz, C₇-H), 7.07 (1H, s, >CH—), 7.41

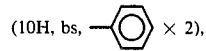

8.52

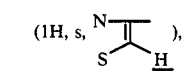

10.07 (1H, d, J=8 Hz, —CONH—).

In the same manner as above, the following compound was obtained:

Diphenylmethyl 7-[2-(2-chloroacetamidothiazol-4-yl)glyoxylamido]-3-[(3-chloro-1,2,4-triazolyl)methyl]-Δ³-cephem-4-carboxylate Melting point: 121°–123° C. (decomp.).

IR(KBr) cm$^{-1}$: $\nu_{C=O}$ 1775, 1720, 1663.

NMR(d$_6$-DMSO) ppm value: 3.52 (2H, bs, C$_2$-H), 4.43 (2H, s, ClCH$_2$—), 4.94–5.57

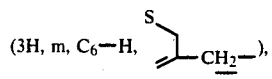 (3H, m, C$_6$—H, ), 5.98 (1H, dd, J=5 Hz J=8 Hz, C$_7$-H), 7.00 (1H, s, >CH—), 7.07–7.67

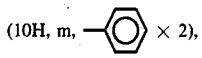 (10H, m, ×2), 7.99

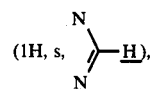 (1H, s, ), 8.42

(1H, s, <chem>N—S—H</chem>), 9.93 (1H, d, J=8 Hz, —CONH—).

(2) In 30 ml of methanol was dissolved 0.84 g of methoxyamine hydrochloride, and 0.76 g of triethylamine was added thereto, after which 3.46 g of the diphenylmethyl 7-[2-(2-chloroacetamidothiazol-4-yl)-glyoxylamido]-3-[2-(5-methyl-1,2,3,4-tetrazolyl)methyl]-Δ$^3$-cephem-4-carboxylate obtained in above (1) was added thereto. The resulting mixture was subjected to reaction at room temperature for 3 hours. After completion of the reaction, the solvent was removed by distillation under reduced pressure, and 30 ml of water and 30 ml of ethyl acetate were added to the residue, after which the organic layer was separated, washed with 20 ml of water and dried on anhydrous magnesium sulfate. The solvent was then removed by distillation under reduced pressure. Diethyl ether was added to the residue, and the resulting crystals were collected by filtration to obtain 2.80 g (yield 77.6%) of diphenylmethyl 7-[2-(2-chloroacetamidothiazol-4-yl)-2-(syn)-methoxyiminoacetamido]-3-[2-(5-methyl-1,2,3,4-tetrazolyl)methyl]-Δ$^3$-cephem-4-carboxylate having a melting point of 129°–132° C. (decomp.).

IR(KBr) cm$^{-1}$: $\nu_{C=O}$ 1780, 1720, 1675.

NMR(d$_6$-DMSO) ppm value: 2.44 (3H, s, —CH$_3$), 3.53 (2H, bs, C$_2$-H), 3.88 (3H, s, —OCH$_3$), 4.38 (2H, s, ClCH$_2$—), 5.26 (1H, d, J=5 Hz, C$_6$-H), 5.55

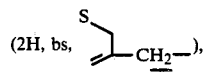 (2H, bs, ), 5.96 (1H, dd, J=5 Hz, J=8 Hz, C$_7$-H), 6.92 (1H, s, >CH—), 7.00–7.63

(11H, m, ×2, ), 9.73 (1H, d, J=8 Hz, —CONH—).

In the same manner as above, the following compound was obtained:

Diphenylmethyl 7-[2-(2-chloroacetamidothiazol-4-yl)-2-(syn)-methoxyiminoacetamido]-3-[(3-chloro-1,2,4-triazolyl)methyl]-Δ$^3$-cephem-4-carboxylate.

Melting point: 120°–124° C. (decomp.).

IR(KBr) cm$^{-1}$: $\nu_{C=O}$ 1780, 1720, 1675.

NMR(d$_6$-DMSO) ppm value: 3.50 (2H, bs, C$_2$-H), 3.90 (3H, s, —OCH$_3$), 4.41 (2H, s, ClCH$_2$—), 4.99–5.41

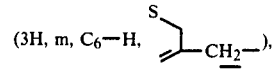 (3H, m, C$_6$—H, ), 5.98 (1H, dd, J=5 Hz, J=8 Hz, C$_7$-H), 6.96 (1H, s, >CH—), 7.03–7.67

 (11H, m, ×2, ), 7.99

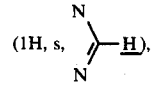 (1H, s, ), 9.73 (1H, d, J=8 Hz, —CONH—).

(3) In 10 ml of N,N-dimethylformamide was dissolved 2.0 g of the diphenylmethyl 7-[2-(2-chloroacetamidothiazol-4-yl)-2-(syn)-methoxyiminoacetamido]-3-[2-(5-methyl-1,2,3,4-tetrazolyl)methyl]-Δ$^3$-cephem-4-carboxylate obtained in above (2), and 0.27 g of thiourea was added thereto, after which the mixture was subjected to reaction at room temperature for 3 hours. After completion of the reaction, the reaction mixture was introduced into a mixed solvent of 20 ml of water and 30 ml of ethyl acetate, and the pH thereof was then adjusted to 7.0 with sodium hydrogen carbonate. The organic layer was separated, washed successively with 15 ml of water and 15 ml of saturated aqueous solution of sodium chloride and dried on anhydrous magnesium sulfate, after which the solvent was removed by distillation under reduced pressure. Diethyl ether was added to the residue, and the resulting crystals were collected by filtration, to obtain 1.45 g (yield 81.0%) of diphenylmethyl 7-[2-(2-aminothiazol-4-yl)-2-(syn)-methoxyiminoacetamido]-3-[2-(5-methyl-1,2,3,4tetrazolyl)methyl]-Δ$^3$-cephem-4-carboxylate having a melting point of 102°–105° C. (decomp.).

IR(KBr) cm$^{-1}$: $\nu_{C=O}$ 1778, 1720, 1660.

NMR(d$_6$-DMSO) ppm value: 2.43 (3H, s, —CH$_3$), 3.45 (2H, bs, C$_2$-H), 3.84 (3H, s, —OCH$_3$), 5.29 (1H, d, J=5 Hz, C$_6$-H), 5.52

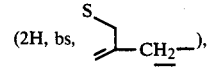 (2H, bs, ), 5.93 (1H, dd, J=5 Hz, J=8 Hz, C$_7$-H, 6.78

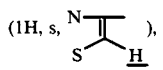 (1H, s, ), 6.91 (1H, s, >CH—), 7.32

(10H, bs, —⌬ × 2), 9.64 (1H, d, J=8 Hz, —CONH—).

In the same manner as above, the following compound was obtained:

Diphenylmethyl 7-[2-(2-aminothiazol-4-yl)-2-(syn)-methoxyiminoacetamido]-3-[(3-chloro-1,2,4-triazolyl)-methyl]-Δ³-cephem-4-carboxylate Melting point: 118°–122° C. (decomp.).

IR(KBr) cm⁻¹: $\nu_{C=O}$ 1775, 1720, 1660.

NMR(d₆-DMSO) ppm value: 3.42 (2H, bs, C₂-H), 3.84 (3H, s, —OCH₃), 4.99–5.39

(3H, m, [S/CH₂—], C₆—H), 5.92 (1H, dd, J=5 Hz, J=8 Hz, C₇-H), 6.77

(1H, s, [N/S-CH structure]), 6.97 (1H, s, >CH—), 7.34

(10H, bs, —⌬ × 2), 8.01

(1H, s, [N/N=CH-H structure]), 9.67 (1H, d, J=8 Hz, —CONH—).

(4) The compound obtained in above (3) was subjected to reaction and treatment in the same manner as in Example 17-(2) to obtain the compounds shown in Table 20.

TABLE 20

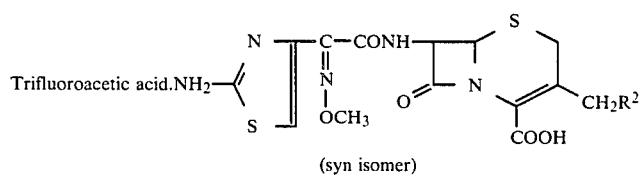

(syn isomer)

| Compound (R²) | Melting point (°C.) |
|---|---|
| —N(N=N)=N—CH₃ triazole | 123–125 (decomp.) |
| N——N oxadiazole with Cl | 162 (decomp.) |

EXAMPLE 30

By subjecting various starting compounds to the same reaction as in Example 29, the corresponding compounds shown in Table 21 were obtained.

TABLE 21

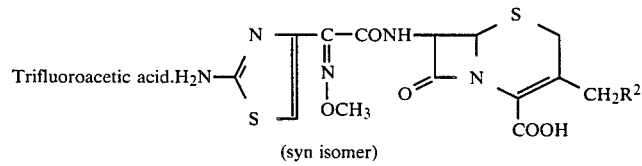

(syn isomer)

| R² | R² | R² |
|---|---|---|
| —N(N=N)=N—CH₃ | —N(N=N)=N—SCH₃ | —N(N=N)=N—COOCH₂CH₃ |

TABLE 21-continued
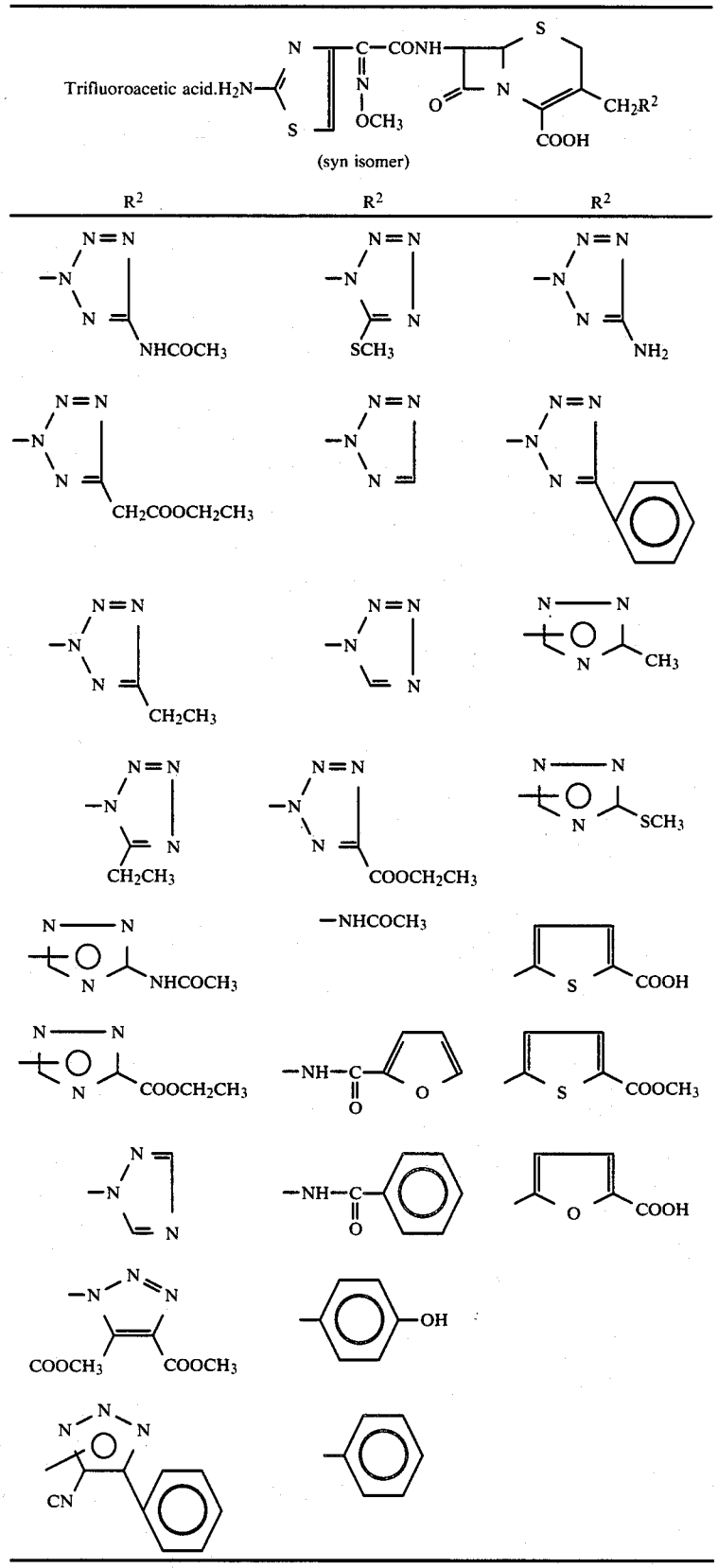
The physical properties of these compounds were identical with those of the compounds produced in Example 21.

(1) In 50 ml of anhydrous methylene chloride was dissolved 3.70 g of 2-[2-(benzyloxycarboxamido)-5-chlorothiazol-4-yl]-2-(syn)-methoxyiminoacetic acid, and 1.06 g of N-methylmorpholine was added to the solution, after which the reaction mixture was cooled to −35° C. Then, 1.12 g of ethyl chlorocarbonate was added thereto and the resulting mixture was subjected to reaction at −30° C. to −20° C. for 2 hours, after which a solution of 4.37 g of diphenylmethyl 7-amino-3-acetamidomethyl-$\Delta^3$-cephem-4-carboxylate in 50 ml of anhydrous chloroform was dropped thereinto. The resulting mixture was subjected to reaction at −20° C. to −10° C. for 1 hour and then at room temperature for 3 hours. After completion of the reaction, the solvent was removed by distillation under reduced pressure, and the residue thus obtained was dissolved in 50 ml of ethyl acetate and 40 ml of water, after which the organic layer was separated. Again, 40 ml of water was added to the organic layer and the pH thereof was adjusted to 1.5 with 2N hydrochloric acid with ice-cooling. The organic layer was separated and dried on anhydrous magnesium sulfate. The solvent was removed by distillation under reduced pressure, and diethyl ether was added to the residue. The resulting crystals were collected by filtration to obtain 6.50 g (yield 82.4%) of diphenylmethyl 7-[2-{2-(benzyloxycarboxamido)-5-chlorothiazol-4-yl}-2-(syn)-methoxyiminoacetamido]-3-acetamidomethyl-$\Delta^3$-cephem-4-carboxylate having a melting point of 132°–136° C. (decomp.).

IR(KBr) cm$^{-1}$: $\nu_{C=O}$ 1780, 1720, 1680–1640.

NMR(d$_6$-DMSO) ppm value: 1.85

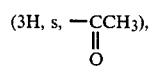

3.51 (2H, bs, C$_2$-H), 3.71–4.35

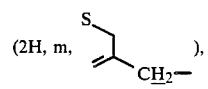

3.89 (3H, s, —OCH$_3$), 5.14 (1H, d, J=5 Hz, C$_6$-H), 5.21

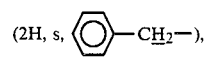

5.86 (1H, dd, J=5 Hz, J=8 Hz, C$_7$-H), 6.88 (1H, s, >C$\underline{H}$—), 6.98–7.67

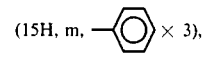

7.78–8.21 (1H, m, —NHCO—), 9.69 (1H, d, J=8 Hz, —CONH—).

(2) In 15 ml of anisole was dissolved 0.79 g of diphenylmethyl 7-[2-{2-(benzyloxycarboxamido)-5-chlorothiazol-4-yl}-2-(syn)-methoxyiminoacetamido]-3-acetamidomethyl-$\Delta^3$-cephem-4-carboxylate, and 1.33 g of aluminum chloride was added to the resulting solution with ice-cooling, after which the resulting mixture was subjected to reaction at 5°–10° C. for 2 hours. After completion of the reaction, the reaction mixture was added to 30 ml of iced water and the pH thereof was adjusted to 7.5 with sodium hydrogen carbonate, after which the insoluble matter was removed by filtration. The filtrate was washed with 30 ml of ethyl acetate, and 50 ml of methyl ethyl ketone was added thereto, after which the pH was adjusted to 2.0 with 2N hydrochloric acid. The organic layer was separated, washed with 30 ml of saturated aqueous solution of sodium chloride and dried on anhydrous magnesium sulfate. The solvent was removed by distillation under reduced pressure, and diethyl ether was added to the residue. The resulting crystals were collected by filtration, to obtain 0.37 g (yield 75.7%) of 7-[2-(2-amino-5-chloro-thiazol-4-yl)-2-(syn)-methoxyiminoacetamido]-3-acetamidomethyl-$\Delta^3$-cephem-4-carboxylic acid having a melting pint of 148°–152° C. (decomp.).

IR(KBr) cm$^{-1}$: $\nu_{C=O}$ 1770, 1710, 1680–1620.

NMR(d$_6$-DMSO) ppm value: 1.83 (3H, s, —COCH$_3$), 3.42 (2H, bs, C$_2$-H), 3.84 (3H, s, —OCH$_3$), 3.70–4.22

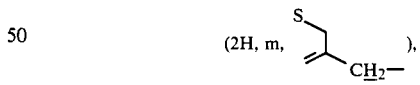

5.02 (1H, D, J=5 Hz, C$_6$-H), 5.67 (1H, d, J=5 Hz, C$_7$-H), 7.85–8.21 (1H, m, —NHCO—), 9.46 (1H, d, J=8 Hz, —CONH—).

EXAMPLE 32

(1) The same reaction and treatment as in Example 18-(1) and (2) were repeated, except that the 2-(2-tert.-amyloxycarboxamidothiazol-4-yl)-2-(syn)-methoxyiminoacetic acid was replaced with a 2-(thiazol-4-yl)-2-(syn)-methoxyiminoacetic acid. As a result, the compounds shown in Table 22 and Table 23 were obtained.

TABLE 22

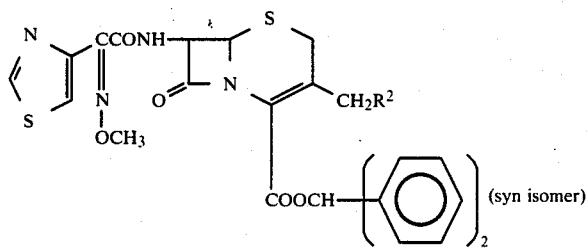
(syn isomer)

| $-R^2$ | Melting point (°C.) | IR(KBr) cm$^{-1}$: $\nu_{C=O}$ | NMR(CDCl$_3$) ppm value: |
|---|---|---|---|
| ![structure with N-N, O, N, Cl, CH] | 102–104 (decomp.) | 1785, 1730, 1680 | 3.14 (2H, bs, C$_2$—H), 3.90 (3H, s, —OCH$_3$), 4.77, 5.34 (2H, ABq, J=15Hz, —S—CH$_2$—), 4.94 (1H, d, J=5Hz, C$_6$—H), 5.88 (1H, dd, J=5Hz, J=8.5Hz, C$_7$—H), 6.82 (1H, s, >CH—), 7.18 (10H, bs, —⌬ × 2), 7.54 (1H, d, J=2Hz, N=C(S)—H), 7.59 (1H, s, N=C(N)—H), 8.11 (1H, d, J=8.5Hz, —CONH—), 8.58 (1H, d, J=2Hz, H—C(N)(S)) |
| ![tetrazole with CH$_3$] | 106–109 (decomp.) | 1780, 1730, 1630 | 2.44 (3H, s, N=C(N)—CH$_3$—), 3.20 (2H, bs, C$_2$—H), 3.98 (3H, s, —OCH$_3$), 4.97 (1H, d, J=6Hz, C$_6$—H), 5.30, 5.70 (2H, ABq, J=15Hz, —S—CH$_2$—), 5.92 (1H, dd, J=6Hz, J=8Hz, C$_7$—H), 6.89 (1H, s, >CH—), 7.25 (10H, bs, —⌬ × 2), 7.65 (1H, d, J=2Hz, N=C(S)—H), 7.74 (1H, d, J=8Hz, —CONH—), 8.67 (1H, d, J=2Hz, H—C(N)(S)) |

TABLE 23

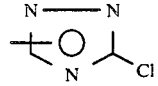

(syn isomer)

| —R² | Melting point (°C.) | IR(KBr) cm⁻¹: $\nu_{C=O}$ | NMR(d₆-DMSO) ppm value: |
|---|---|---|---|
| 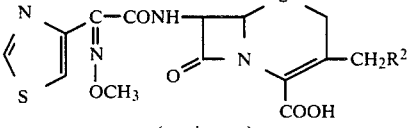 | 130–140 (decomp.) | 1780, 1715, 1670 | 3.39 (2H, bs, C₂—H), 3.83 (3H, s, —OCH₃), 4.88 (1H, d, J=5Hz, C₆—H), 5.12 (2H, bs, ), 5.79 (1H, dd, J=5Hz, J=8.5Hz, C₇—H), 7.83 (1H, d, J=2Hz, 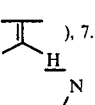), 7.93 (1H, s, 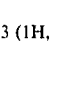), 9.02 (1H, d, J=2Hz, ), 9.56 (1H, d, J=8.5Hz, —CONH—) |
| 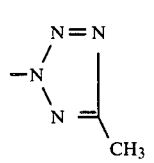 | 129–134 (decomp.) | 1780, 1720, 1675 | 2.44 (3H, s, 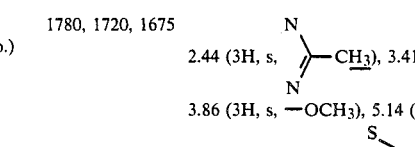), 3.41 (2H, bs, C₂—H), 3.86 (3H, s, —OCH₃), 5.14 (1H, d, J=5Hz, C₆—H), 5.60 (2H, bs, ), 5.81 (1H, dd, J=5Hz, J=8.5Hz, C₇—H), 7.86 (1H, d, J=2Hz, ), 9.07 (1H, d, J=2Hz, 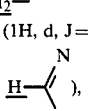), 9.63 (1H, d, J=8.5Hz, —CONH—) |

EXAMPLE 33

(1) In 30 ml of N,N-dimethylformamide was dissolved 6.13 g of 7-[2-(2-tert.-amyloxycarboxamidothiazol-4-yl)-2-(syn)-methoxyiminoacetamido]-3-[(3-chloro-1,2,4-triazolyl)]methyl-Δ³-cephem-4-carboxylic acid, and 1 g of triethylamine and 2.9 g of pivaloyloxymethyl iodide were added to the resulting solution with ice-cooling, after which the resulting mixture was subjected to reaction for 30 minutes. After completion of the reaction, the reaction mixture was introduced into a mixed solvent of 300 ml of water and 300 ml of ethyl acetate, and the pH thereof was adjusted to 7.0 with sodium hydrogen carbonate. Then, the organic layer was separated, washed successively with 100 ml of water and 100 ml of saturated aqueous solution of sodium chloride and dried on anhydrous magnesium sulfate, after which the solvent was removed by distillation under reduced pressure. Diisopropyl ether was added to the residue, and the resulting crystals were collected by filtration, thoroughly washed with diisopropyl ether and dried, to obtain 6.6 g (yield 90.8%) of pivaloyloxymethyl 7-[2-(2-tert.-amyloxycarboxamidothiazol-4-yl)-2-(syn)-methoxyiminoacetamido]-3-[(3-chloro-1,2,4-triazolyl)methyl]-Δ³-cephem-4-carboxylate.

IR(KBr) cm⁻¹: $\nu_{C=O}$ 1790, 1750, 1720, 1675.

NMR(CDCl₃) ppm value: 0.96 (3H, t, J=7 Hz, —CH₂CH₃), 1.30 (9H, s, —C(CH₃)₃), 1.57 (6H, s, 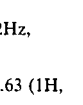), 1.91 (2H, q, J=7 Hz, —CH₂CH₃), 3.33 (2H, bs, C₂-H), 4.02 (3H, s, —OCH₃), 4.89–5.34 (3H, m, 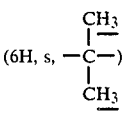, C₆—H), 5.70–6.27 (3H, m, —COOCH₂—, C₇-H), 7.14 7.90 (1H, s, 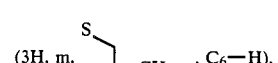), (1H, s, 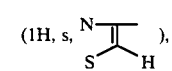), 9.31 (1H, d, J=8 Hz, —CONH—).

(2) In 33 ml of trifluoroacetic acid was dissolved 6.6 g of pivaloyloxymethyl 7-[2-(2-tert.-amyloxycarboxamidothiazol-4-yl)-2-(syn)-methoxyiminoacetamido]-3-[(3-chloro-1,2,4-triazolyl)methyl]-Δ³-cephem-4-carboxylate, and the resulting solution was subjected to reaction at room temperature for 30 minutes. After completion of the reaction, the solvent was removed by distillation under reduced pressure, and 80 ml of water and 80 ml of ethyl acetate were added to the residue, after which the pH of the resulting solution was adjusted to 7.0 with sodium hydrogen carbonate with ice-cooling. The organic layer was separated and dried on anhydrous magnesium sulfate, and a solution of dry hydrogen chloride in diethyl ether was added thereto with ice-cooling and with stirring, upon which a white colored powder was deposited. It was collected by filtration, thoroughly washed with diethyl ether and dried to obtain 5.2 g (yield 88.2%) of hydrochloride of pivaloyloxymethyl 7-[2-(2-aminothiazol-4-yl)-2-(syn)-methoxyiminoacetamido]-3-[(3-chloro-1,2,4-triazolyl)-methyl]-$\Delta^3$-cephem-4-carboxylate having a melting point of 134°–136° C. (decomp.).

IR(KBr) cm$^{-1}$: $\nu_{C=O}$ 1790, 1755, 1680.

NMR(d$_6$-DMSO) ppm value: 1.17 (9H, s, —C(CH$_3$)hd 3), 3.49 (2H, bs, C$_2$-H), 3.93 (3H, s, —OCH$_3$) 4.95–5.40

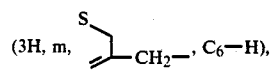 (3H, m, S/CH$_2$—, C$_6$—H), 5.60–6.02 (3H, m, —COOCH$_2$—, C$_7$-H), 6.91

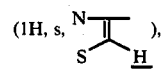 (1H, s, N/S/H), 8.00

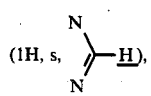 (1H, s, N/N—H), 8.83 (1H, d, J=9 Hz, —CONH—).

EXAMPLE 34

(1) In 20 ml of N,N-dimethylformamide was suspended 2.96 g of 7-amino-3-[2-(5-methyl-1,2,3,4-tetrazolyl)methyl]-$\Delta^3$-cephem-4-carboxylic acid. Then, the suspension was converted to a solution by adding 1.1 g of triethylamine with ice-cooling. Then, 2.7 g of pivaloyloxymethyl iodide was added to the solution, and the resulting mixture was subjected to reaction at 0°–5° C. for 1 hour. After completion of the reaction, the reaction mixture was introduced into a mixed solvent of 250 ml of water and 200 ml of ethyl acetate, and the pH thereof was adjusted to 7.0 with sodium hydrogen carbonate. After removing the insoluble matter, the organic layer was separated and dried on anhydrous magnesium sulfate, and then the solvent was removed by distillation under reduced pressure. After washing the residue with diethyl ether, the residue was dissolved in 30 ml of ethyl acetate, and a solution of 1 g of dry hydrogen chloride in 30 ml of diethyl ether was added to the resulting solution with ice-cooling and with stirring. The deposited crystals were collected by filtration, thoroughly washed with diethyl ether and then recrystallized from chloroform to obtain 2.72 g (yield 60.9%) of hydrochloride of pivaloyloxymethyl 7-amino-3-[2-(5-methyl-1,2,3,4-tetrazolyl)methyl]-$\Delta^3$-cephem-4-carboxylate having a melting point of 149°–151° C. (decomp.).

IR(KBr) cm$^{-1}$: $\nu_{C=O}$ 1773, 1741, 1730.

NMR(d$_6$-DMSO) ppm value: 1.18 (9H, s, —C(CH$_3$)$_3$), 2.44 (3H, s, —CH$_3$), 3.60 (2H, s, C$_2$-H), 5.23 (2H, s, C$_6$-H, C$_7$-H), 5.62

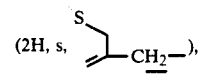 (2H, s, S/CH$_2$—), 5.78–5.92 (2H, m, —COOCH$_2$O—).

By subjecting various starting compounds to the same reaction as above, the corresponding compounds shown in Table 24 and Table 25 were obtained.

TABLE 24

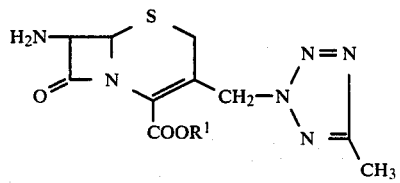

| Compound R$^1$ | Melting point (°C.) | IR(KBr) cm$^{-1}$: $\nu_{C=O}$ | NMR ( d$_6$-DMSO* / CDCl$_3$ / CD$_3$OD* ) ppm value: | Note (treatment) |
|---|---|---|---|---|
| —CHOCOCH$_2$CH$_3$ <br> \| \|\| <br> CH$_3$ O | — | 1775, 1758 | 1.28 (3H, t, J=7Hz, —CH$_2$CH$_3$), <br><br> 1.58 (3H, d, J=6Hz, \\CHCH$_3$/), <br><br> 2.02 (2H, bs, —NH$_2$), 2.51 (3H, s, —CH$_3$), 3.33 (2H, bs, C$_2$—H), <br><br> 4.20 (2H, q, J=7Hz, —CH$_2$CH$_3$), <br><br> 4.90 (2H, bs, C$_6$—H, C$_7$—H), 5.61 <br><br> (2H, bs, S/CH$_2$—), 6.69–7.06 | Column chromatography (Wako silica gel C-200; developing solvent, benzene:ethyl acetate = 3:1) |

TABLE 24-continued

Structure shown:
$H_2N$— (β-lactam ring with S), COOR$^1$, CH$_2$—N(triazole with =N—N and CH$_3$)

| Compound R$^1$ | Melting point (°C.) | IR(KBr) cm$^{-1}$: $\nu_{C=O}$ | NMR (d$_6$-DMSO* / CDCl$_3$** / CD$_3$OD***) ppm value: | Note (treatment) |
|---|---|---|---|---|
| | | | (1H, m, \CHCH$_3$/) | |
| phthalide-type structure (benzofuranone) | 98–101 | 1788, 1740 | ** 1.80 (2H, s, —NH$_2$), 2.42 (1.5H, s, —CH$_3$), 2.49 (1.5H, s, —CH$_3$), 3.27 (1H, s, C$_2$—H), 3.30 (1H, s, C$_2$—H), 4.62–4.95 (2H, m, C$_6$—H, C$_7$—H), 5.30, 5.65 (2H, ABq, J=17Hz, S\\=/CH$_2$—), 7.37 (0.5H), s, \—CH/), 7.42 (0.5H, s, \—CH/), 7.54–7.87 (4H, m, phenyl) | Column chromatography (Wako silica gel C-200; developing solvent, benzene:ethyl acetate = 3:1) |
| ****  —CHOCC(CH$_3$)$_3$   \| \|\|    CH$_3$ O | 135–137 (decomp.) | 1800, 1735 | 1.14 (9H, s, —C(CH$_3$)$_3$), 1.47 (3H, d, J=6Hz, \CH—CH$_3$/), 2.44 (3H, s, N\\=/—CH$_3$), 3.49 (2H, bs, C$_2$—H), 4.86 (1H, d, J=6Hz, C$_6$—H), 5.06 (1H, d, J=6Hz, C$_7$—H), 5.50 (2H, bs, S\\=/CH$_2$—), 6.80 (1H, q, J=6Hz, \CH—CH$_3$/), 7.03 (3H, bs, H$_3$N$^\oplus$—) | Oxalic acid was added to ethyl acetate solution to form oxalate. |
| ****  —CH$_2$OCH$_2$CH$_3$ | 125–130 (decomp.) | 1790, 1780 | * 1.18 (3H, t, J=7Hz, —CH$_2$CH$_3$), 2.47 (3H, s, —CH$_3$), 3.27 (2H, bs, C$_2$—H), 3.55 (2H, q, J=7Hz, —CH$_2$CH$_3$), 5.08–5.68 (6H, m, C$_6$—H, C$_7$—H, —COOCH$_2$O—, S\\=/CH$_2$—) | Oxalic acid was added to ethyl acetate solution to form oxalate. |
| ****  —CH$_2$OCCH$_3$   \|\|    O | 107–110 (decomp.) | 1785, 1735 | *** 2.08 (3H, s, —OCCH$_3$ \|\| O), 2.45 (3H, s, N\\=/—CH$_3$), 3.50 (2H, bs, C$_2$—H), 4.96 (1H, d, J=6Hz, C$_6$—H), 5.11 (1H, d, J=6Hz, | Oxalic acid was added to ethyl acetate solution to form oxalate. |

TABLE 24-continued

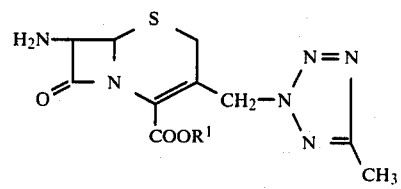

| Compound R[1] | Melting point (°C.) | IR(KBr) cm$^{-1}$: $v_{C=O}$ | NMR (d$_6$-DMSO* / CDCl$_3$ / CD$_3$OD*) ppm value: | Note (treatment) |
|---|---|---|---|---|
| | | | C$_7$—H), 5.58 (2H, bs, S⟩CH$_2$—), 5.82 (2H, s, —COOCH$_2$O—), 7.66 (3H, bs, H$_3$N$^\oplus$—) * | |
| ****  —CH$_2$OC(CH$_2$)$_3$CH$_3$  ‖  O | 117–120 (decomp.) | 1780, 1750 | 0.87 (3H, t, J=7Hz, —(CH$_2$)$_3$CH$_3$), 1.00–1.90 (4H, m, —CH$_2$CH$_2$CH$_2$CH$_3$), 2.30–2.54 (2H, m, —CH$_2$CH$_2$CH$_2$CH$_3$), 2.47 (3H, s, N⟩—CH$_3$ / N), 3.52 (2H, bs, C$_2$—H), 4.96 (1H, d, J=6Hz, C$_6$—H), 5.14 (1H, d, J=6Hz, C$_7$—H), 5.42 (2H, bs, S⟩CH$_2$—), 5.74 (2H, s, —OCH$_2$O—), 7.66 (3H, bs, H$_3$N$^\oplus$—) * | Oxalic acid was added in ethyl acetate solution to form oxalate. |
| —CHOCO(CH$_2$)$_3$CH$_3$  \|  ‖  CH$_3$ O | — | 1780, 1758 | 0.92 (3H, t, J=6Hz, —(CH$_2$)$_3$CCH$_3$), 1.12–1.70 (4H, m, —CH$_2$CH$_2$CH$_2$CH$_3$), 1.60 (3H, d, J=6Hz, ⟩CH—CH$_3$), 1.89 (2H, s, —NH$_2$), 2.52 (3H, s, N⟩—CH$_3$ / N), 3.32 (2H, bs, C$_2$—H), 4.14 (2H, t, J=6Hz, —CH$_2$CH$_2$CH$_2$CH$_3$), 4.78 (1H, d, J=5Hz, C$_6$—H), 4.91 (1H, d, J=5Hz, C$_7$—H), 5.44, 5.77 (2H, ABq, J=15Hz, S⟩CH$_2$—), 6.96 (1H, q, J=6Hz, ⟩CH—CH$_3$) ** | Column chromatography (Wako silica gel C-200; developing solvent, benzene:ethyl acetate = 5:1) |
| ****  —CH$_2$O(CH$_2$)$_3$CH$_3$ | 118–120 (decomp.) | 1800, 1700 | 0.87 (3H, t, J=7Hz, —CH$_2$CH$_2$CH$_2$CH$_3$), 1.10–1.75 (4H, m, —CH$_2$CH$_2$CH$_2$CH$_3$), 2.48 (3H, s, N⟩—CH$_3$ / N), 3.52 | Oxalic acid was added to ethyl acetate solution to form oxalate |

TABLE 24-continued

[Structure: β-lactam with H₂N-, S, N, COOR¹, CH₂-N connected to tetrazole ring with N=N and CH₃]

| Compound R¹ | Melting point (°C.) | IR(KBr) cm⁻¹: $\nu_{C=O}$ | NMR $\begin{pmatrix} d_6\text{-DMSO*} \\ CDCl_3** \\ CD_3OD*** \end{pmatrix}$ ppm value: | Note (treatment) |
|---|---|---|---|---|
| | | | (2H, bs, C₂—H), 3.64 (2H, t, J=7Hz, —C$\underline{H_2}$CH₂CH₂CH₃), 5.00 (1H, d, J=5Hz, C₆—H), 5.17 (1H, d, J=5Hz, C₇—H), 5.44 (2H, s, —OCH₂O—), 5.64 (2H, s, [S-CH₂ group]), 7.83 (3H, bs, —$\overset{\oplus}{N}H_3$) * | |
| —CHOCOC(CH₃)₃<br>   \|<br>   CH₃ O | — | 1770, 1750 | 1.55 (9H, s, —C(CH₃)₃), 1.66 (3H, d, J=6Hz, \CH—CH₃), 2.20 (2H, s, —NH₂), 2.60 (3H, s, [N-CH₃ group]), 3.44 (2H, bs, C₂—H), 4.98 (1H, d, J=5Hz, C₆—H), 5.11 (1H, d, J=5Hz, C₇—H), 5.80 (2H, bs, [S-CH₂ group]), 7.10 (1H, q, J=6Hz, \C$\underline{H}$—CH₃) ** | |

Note:
**** Oxalate

TABLE 25

[Structure: β-lactam with H₂N-, S, N, COOR¹, CH₂ connected to N—N ring with O and Cl]

| Compound R¹ | Melting point (°C.) | IR(KBr) cm⁻¹: $\nu_{C=O}$ | NMR $\begin{pmatrix} d_6\text{-DMSO*1} \\ CDCl_3*2 \end{pmatrix}$ ppm value: | Note (treatment) |
|---|---|---|---|---|
| *3<br>—CH₂OCC(CH₃)₃<br>     ‖<br>     O | 152–155 (decomp.) | 1803, 1750 | 1.13 (9H, s, —C(CH₃)₃), 3.39 (2H, bs, C₂—H), 4.90 (1H, d, J=5Hz, C₆—H), 5.10 (2H, bs, [S-CH₂ group]), 5.72 (1H, d, J=5Hz, C₇—H), 6.28 (3H, bs, $H_3\overset{\oplus}{N}$—), 7.89 (1H, s, [N-C(H)-N group]) *1 | Oxalic acid was added to ethyl acetate solution to form oxalate. |

TABLE 25-continued

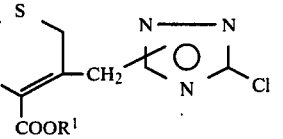

| Compound R[1] | Melting point (°C.) | IR(KBr) cm[-1]: $\nu_{C=O}$ | NMR($^{d_6\text{-DMSO}*1}_{\text{CDCl}_3*2}$) ppm value: | Note (treatment) |
|---|---|---|---|---|
| \*<br>—CHOCOCH$_2$CH$_3$<br>   ∥<br>   O<br>   CH$_3$<br>\*4 | 146–148 | 1778, 1720 | 1.27 (3H, t, J=7Hz, —CH$_2$C$\underline{\text{H}}_3$), 1.57 (3H, d, J=6Hz, \CHC$\underline{\text{H}}_3$), 3.22 (2H, bs, C$_2$—H), 4.17 (2H, q, J=7Hz, —C$\underline{\text{H}}_2$CH$_3$), 4.70 (1H, d, J=5Hz, C$_6$—H), 4.86 (1H, d, J=5Hz, C$_7$—H), 4.91, 5.51 (2H, ABq, J=15Hz, 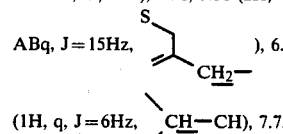), 6.85 (1H, q, J=6Hz, \C$\underline{\text{H}}$—CH$_3$/), 7.73 (1H, s, 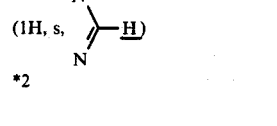)<br>\*2 | Column chromatography (Wako silica gel C-200; developing solvent, benzene:ethyl acetate = 3:1) |
| \*<br>—CHOCOCH$_2$CH$_3$<br>   ∥<br>   O<br>   CH$_3$<br>\*5 | 67–70 | 1780, 1760 | 1.32 (3H, t, J=7Hz, —CH$_2$C$\underline{\text{H}}_3$), 1.59 (3H, d, J=6Hz, \CH—C$\underline{\text{H}}_3$/), 1.86 (2H, s, —NH$_2$), 3.20 (2H, s, C$_2$—H), 4.20 (2H, q, J=7Hz, —C$\underline{\text{H}}_2$CH$_3$), 4.72 (1H, d, J=5Hz, C$_6$—H), 4.87 (1H, d, J=5Hz, C$_7$—H), 4.99, 5.52 (2H, ABq, J=15Hz, 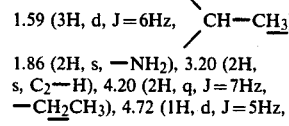), 6.95 (1H, q, J=6Hz, \C$\underline{\text{H}}$—CH$_3$/), 7.75 (1H, s, 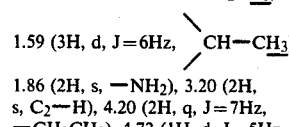) | Column chromatography (Wako silica gel C-200; developing solvent, benzene:ethyl acetate = 3:1) |
| \*3<br>—CH$_2$O(CH$_2$)CH$_3$ | 128–135 | 1773, 1720 | 0.90 (3H, t, J=7Hz, —(CH$_2$)$_3$C$\underline{\text{H}}_3$), 1.15–1.71 (4H, m, —CH$_2$C$\underline{\text{H}}_2$C$\underline{\text{H}}_2$CH$_3$), 3.30–3.65 (4H, m, C$_2$—H, —C$\underline{\text{H}}_2$CH$_2$CH$_2$CH$_3$), 4.95–5.40 (6H, m, —OCH$_2$O—, C$_6$—H, C$_7$—H, 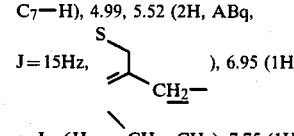), 8.01 (1H, s, 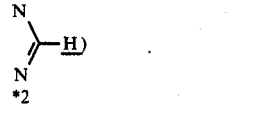), 8.84 (3H, bs, —$\overset{\oplus}{\text{N}}$H$_3$)\* | Oxalic acid was added to ethyl acetate solution to form oxalate. |

Note:
\*Optical isomer
\*3 Oxalate
\*4 Upper component
\*5 Lower component

EXAMPLE 35

To a mixed solvent of 8 ml of anhydrous methylene chloride and 2.2 ml of N,N-dimethylacetamide was added 3.7 g of phosphorus oxychloride at 0°–5° C., and the resulting mixture was subjected to reaction at that temperature for 30 minutes. Then, the reaction mixture was cooled to −15° C. to −10° C., and 2.4 g of 2-(2-aminothiazol-4-yl)-2-(syn)-methoxyiminoacetic acid was added thereto, and the resulting mixture was subjected to reaction at that temperature for 20 minutes. Then, a solution of 4.47 g of hydrochloride of pivaloyloxymethyl 7-amino-3-[2-(5-methyl-1,2,3,4-tetrazolyl)-methyl]-Δ³-cephem-4-carboxylate and 1.01 g of triethylamine in 20 ml of anhydrous methylene chloride was dropped into the above-mentioned reaction mixture at −10° C. After the dropping, the mixture was subjected to reaction at −10° C. for 30 minutes, at 0° C. for 30 minutes and then at room temperature for 30 minutes. After completion of the reaction, the solvent was removed by distillation under reduced pressure, and 50 ml of water and 50 ml of ethyl acetate were added to the residue, after which the pH thereof was adjusted to 7.0 with sodium hydrogen carbonate. The organic layer was separated, washed successively with 30 ml of water and 30 ml of saturated aqueous solution of sodium chloride and dried on anhydrous magnesium sulfate. The solvent was removed by distillation under reduced pressure, and diethyl ether was added to the residue. The resulting crystals were collected by filtration to obtain 5.1 g (yield 86%) of pivaloyloxymethyl 7-[2-(2-aminothiazol-4-yl)-2-(syn)-methoxyiminoacetamido]-3-[2-(5-methyl-1,2,3,4-tetrazolyl)methyl-Δ³-cephem-4-carboxylate having a melting point of 127°–128° C. (decomp.)

IR(KBr) cm⁻¹: $\nu_{C=O}$ 1780, 1743, 1675.

EXAMPLE 36

By subjecting various starting compounds to the same reaction as in Example 33 or Example 35, the corresponding compounds shown in Table 26, Table 27 and Table 28 were obtained.

TABLE 26

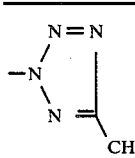

| Compound R² | Melting point (°C.) | IR(KBr) cm⁻¹: $\nu_{C=O}$ | NMR(d₆-DMSO) ppm value |
|---|---|---|---|
|  | 144–148 * (decomp.) | 1790, 1750, 1675 | 1.17 (9H, s, —C(CH₃)₃), 2.46 (3H, s, 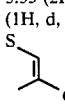), 3.55 (2H, bs, C₂—H), 3.96 (3H, s, —OCH₃), 5.19 (1H, d, J=5Hz, C₆—H), 5.39–6.00 (5H, m, 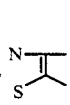, C₇—H, —OCH₂O—), 6.96 (1H, s, 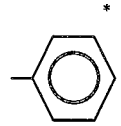), 9.84 (1H, d, J=8Hz, —CONH—) |
| 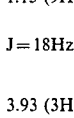 | 119–123 * (decomp.) | 1780, 1740, 1670 | 1.15 (9H, s, —C(CH₃)₃), 3.18, 3.60 (2H, ABq, J=18Hz, C₂—H), 3.58–4.22 (2H, m, 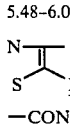), 3.93 (3H, s, —OCH₃), 5.17 (1H, d, J=5Hz, C₆—H), 5.48–6.02 (3H, m, —OCH₂O—, C₇—H), 6.92 (1H, s, 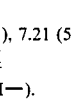), 7.21 (5H, bs, 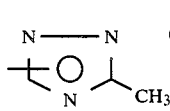), 9.85 (1H, d, J=8Hz, —CONH—). |
| 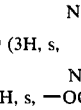 | 144–146 (decomp.) | 1780, 1745, 1660 | 1.16 (9H, s, —C(CH₃)₃), 2.39 (3H, s, 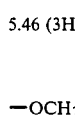), 3.56 (2H, bs, C₂—H), 3.88 (3H, s, —OCH₃), 4.85–5.46 (3H, m, 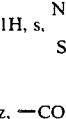, C₆—H), 5.52–6.01 (3H, m, —OCH₂O—, C₇—H), 6.86 (1H, s, 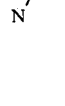), 7.80 (1H, s, —N=CH—N—), 9.74 (1H, d, J=8Hz, —CONH—) |

TABLE 26-continued

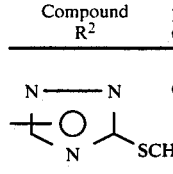

| Compound $R^2$ | Melting point (°C.) | IR(KBr) cm$^{-1}$: $\nu_{C=O}$ | NMR(d$_6$-DMSO) ppm value |
|---|---|---|---|
|  | 135–137 (decomp.) | 1785, 1745, 1672 | 1.17 (9H, s, —C(CH$_3$)$_3$), 2.49 (3H, s, —SCH$_3$), 3.52 (2H, bs, C$_2$—H), 3.93 (3H, s, —OCH$_3$), 4.87–5.38 (3H, m, , C$_6$—H), 5.50–6.05 (3H, m, —OCH$_2$O—, C$_7$—H), 6.92 (1H, s, 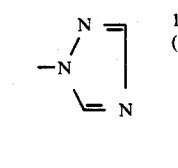), 8.50 (1H, s, ), 9.80 (1H, d, J=8Hz, —CONH—) |
| —NHCOCH$_3$ | 133–135 (decomp.) | 1780, 1740, 1680~1620 | 1.16 (9H, s, —C(CH$_3$)$_3$), 1.81 (3H, s, —COCH$_3$), 3.46 (2H, bs, C$_2$—H), 3.61–4.18 (2H, m, 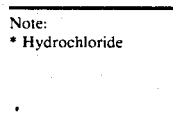), 3.80 (3H, s, —OCH$_3$), 5.05 (1H, d, J=5Hz, C$_6$—H), 5.48–6.00 (3H, m, —COOCH$_2$—, C$_7$—H), 6.66 (1H, s, 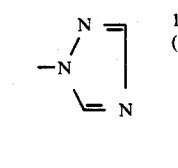), 7.12 (2H, bs, —NH$_2$), 7.78–8.09 (1H, m, —NHCO—), 9.45 (1H, d, J=8Hz, —CONH—) |
|  | 130–132 (decomp.) | 1780, 1745, 1665 | 1.21 (9H, s, —C(CH$_3$)$_3$), 3.50 (2H, bs, C$_2$—H), 3.90 (3H, s, —OCH$_3$), 4.88–5.30 (3H, m, , C$_6$—H), 5.64–6.04 (3H, m, —COOCH$_2$—, C$_7$—H), 6.72 (1H, s, 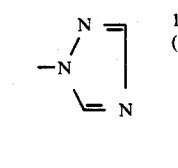), 7.83 (1H, s, ), 8.37 (1H, s, ), 9.46 (1H, d, J=8Hz, —CONH—) |

Note:
* Hydrochloride

TABLE 27

| R$^1$ | Melting point (°C.) | IR(KBr) cm$^{-1}$: $\nu_{C=O}$ | NMR(d$_6$-DMSO) ppm value: |
|---|---|---|---|
| *—CH$_3$ | 154 (decomp.) | 1785, 1730, 1655 | 2.48 (3H, s, ), 3.53 (2H, bs, C$_2$—H), 3.81 (3H, s, —COOCH$_3$), 3.96 (3H, s, —OCH$_3$), 5.23 (1H, d, J=5Hz, C$_6$—H), 5.61 (2H, bs, ), 5.83 (1H, |

TABLE 27-continued

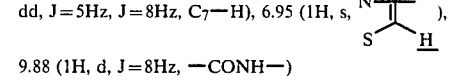 (syn isomer)

| R[1] | Melting point (°C.) | IR(KBr) cm$^{-1}$: $\nu_{C=O}$ | NMR(d$_6$-DMSO) ppm value: |
|---|---|---|---|
| | | | dd, J=5Hz, J=8Hz, C$_7$—H), 6.95 (1H, s, 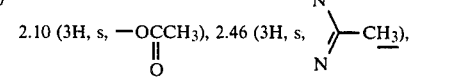), 9.88 (1H, d, J=8Hz, —CONH—) |
| —CH$_2$OCCH$_3$ ‖ O | 121–124 (decomp.) | 1780, 1745, 1670 | 2.10 (3H, s, —OCCH$_3$), 2.46 (3H, s, 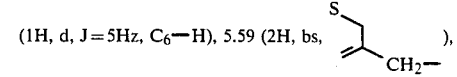), ‖ O 3.52 (2H, bs, C$_2$—H), 3.82 (3H, s, —OCH$_3$), 5.19 (1H, d, J=5Hz, C$_6$—H), 5.59 (2H, bs, 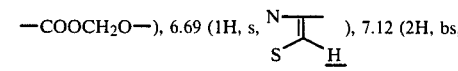), 5.78 (1H, dd, J=5Hz, J=8Hz, C$_7$—H), 5.83 (2H, s, —COOCH$_2$O—), 6.69 (1H, s, 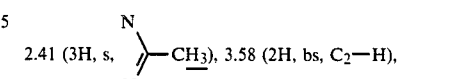), 7.12 (2H, bs, —NH$_2$), 9.55 (1H, d, J=8Hz, —CONH—) |
| 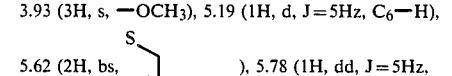 | 166–168 (decomp.) | 1775, 1745, 1665 | 2.41 (3H, s, 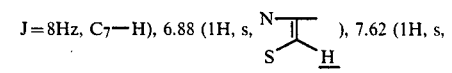), 3.58 (2H, bs, C$_2$—H), 3.93 (3H, s, —OCH$_3$), 5.19 (1H, d, J=5Hz, C$_6$—H), 5.62 (2H, bs, 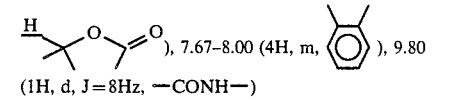), 5.78 (1H, dd, J=5Hz, J=8Hz, C$_7$—H), 6.88 (1H, s, 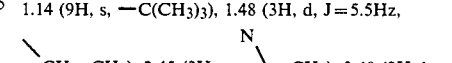), 7.62 (1H, s, 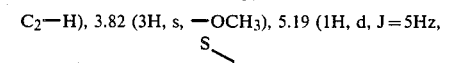), 7.67–8.00 (4H, m, 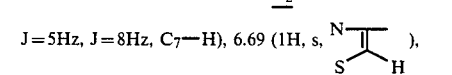), 9.80 (1H, d, J=8Hz, —CONH—) |
| —CHOCC(CH$_3$)$_3$ \| ‖ CH$_3$ O | 127–130 (decomp.) | 1780, 1740, 1675 | 1.14 (9H, s, —C(CH$_3$)$_3$), 1.48 (3H, d, J=5.5Hz, 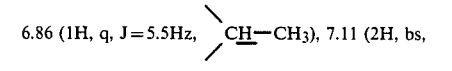CH—CH$_3$), 2.45 (3H, s, 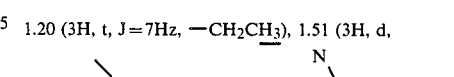—CH$_3$), 3.48 (2H, bs, C$_2$—H), 3.82 (3H, s, —OCH$_3$), 5.19 (1H, d, J=5Hz, C$_6$—H), 5.54 (2H, bs, ), 5.83 (1H, dd, J=5Hz, J=8Hz, C$_7$—H), 6.69 (1H, s, ), 6.86 (1H, q, J=5.5Hz, CH—CH$_3$), 7.11 (2H, bs, —NH$_2$), 9.56 (1H, d, J=8Hz, —CONH—) |
| —CHOCOCH$_2$CH$_3$ \| ‖ CH$_3$ O | 130–136 (decomp.) | 1780, 1775, 1665 | 1.20 (3H, t, J=7Hz, —CH$_2$CH$_3$), 1.51 (3H, d, J=6Hz, CH—CH$_3$), 2.45 (3H, s, —CH$_3$), 3.55 (2H, bs, C$_2$—H), 3.85 (3H, s, —OCH$_3$), 4.16 (2H, q, J=7Hz, —CH$_2$CH$_3$), 5.20 (1H, d, J=5Hz, C$_6$—H), |

TABLE 27-continued

[Structure: $H_2N$-thiazole-C(=N-OCH$_3$)-CONH-β-lactam-CH$_2$-N(N=N)-N=C(CH$_3$)- with COOR$^1$ (syn isomer)]

| R$^1$ | Melting point (°C.) | IR(KBr) cm$^{-1}$: $\nu_{C=O}$ | NMR(d$_6$-DMSO) ppm value: |
|---|---|---|---|
| | | | 5.55 (2H, bs, —S-CH$_2$—), 5.81 (1H, dd, J=5Hz, J=8Hz, C$_7$—H), 6.72 (1H, s, thiazole-H), 6.81 (1H, q, J=6Hz, CH—CH$_3$), 9.60 (1H, d, J=8Hz, —CONH—) |
| —CH$_2$O(CH$_2$)$_3$CH$_3$ | 148–152 (decomp.) | 1785, 1730, 1675 | 0.88 (3H, t, J=7Hz, —(CH$_2$)$_3$CH$_3$), 1.05–1.75 (4H, m, —CH$_2$CH$_2$CH$_2$CH$_3$), 2.45 (3H, s, N=C(CH$_3$)—N), 3.45 (2H, t, J=7Hz, —CH$_2$CH$_2$CH$_2$CH$_3$), 3.55 (2H, bs, C$_2$—H), 3.87 (3H, s, —OCH$_3$), 5.23 (1H, d, J=5Hz, C$_6$—H), 5.43 (2H, s, —COOCH$_2$O—), 5.62 (2H, bs, —S-CH$_2$—), 5.86 (1H, dd, J=5Hz, J=8Hz, C$_7$—H), 6.74 (1H, s, thiazole-H), 9.63 (1H, d, J=8Hz, —CONH—) |
| —CH$_2$OC(=O)(CH$_2$)$_3$CH$_3$ | 107–108 | 1780, 1760, 1670 | 0.87 (3H, t, J=7Hz, —(CH$_2$)$_3$CH$_3$), 1.0–1.7 (4H, m, —CH$_2$CH$_2$CH$_2$CH$_3$), 2.25–2.55 (2H, m, —CH$_2$CH$_2$CH$_2$CH$_3$), 2.45 (3H, s, N=C(CH$_3$)—N), 3.33 (2H, bs, C$_2$—H), 3.85 (3H, s, —OCH$_3$), 5.20 (1H, d, J=5Hz, C$_6$—H), 5.58 (2H, bs, —S-CH$_2$—), 5.88 (2H, s, —OCH$_2$O—), 5.73–5.97 (1H, m, C$_7$—H), 6.70 (1H, s, thiazole-H), 7.18 (2H, bs, —NH$_2$), 9.60 (1H, d, J=9Hz, —CONH—) |
| —CH(CH$_3$)OCO(CH$_2$)$_3$CH$_3$ | 125–130 (decomp.) | 1780, 1760, 1667 | 0.87 (3H, t, J=6Hz, —(CH$_2$)$_3$CH$_3$), 1.15–1.70 (4H, m, —CH$_2$CH$_2$CH$_2$CH$_3$), 1.53 (3H, d, J=6Hz, CH—CH$_3$), 2.46 (3H, s, N=C(CH$_3$)—N), 3.54 (2H, bs, C$_2$—H), 3.86 (3H, s, —OCH$_3$), 4.11 (2H, t, J=6Hz, —CH$_2$CH$_2$CH$_2$CH$_3$), 5.23 (1H, d, J=5Hz, C$_6$—H), 5.59 (2H, bs, —S-CH$_2$—), 5.85 (1H, dd, J=5Hz, J=8Hz, C$_7$—H), 6.76 (1H, s, thiazole-H), |

TABLE 27-continued

[Structure: H₂N-(thiazole)-C(=N-OCH₃)-CONH-(β-lactam-S)-CH₂-N(triazole with N=N)-C(CH₃) with COOR¹ (syn isomer)]

| R¹ | Melting point (°C.) | IR(KBr) cm⁻¹: $\nu_{C=O}$ | NMR(d₆-DMSO) ppm value: |
|---|---|---|---|
| —CHOCOC(CH₃)₃<br>   \|   \|\|<br>  CH₃ O | 128–135 | 1780, 1755, 1665 | 6.81 (1H, q, J=6Hz, >CH—CH₃), 9.65 (1H, d, J=8Hz, —CONH—)<br>1.41 (9H, s, —C(CH₃)₃), 1.51 (3H, d, J=7Hz, >CH—CH₃), 2.50 (3H, s, (N=N ring)—CH₃), 3.56 (2H, bs, C₂—H), 3.92 (3H, s, —OCH₃), 5.29 (1H, d, J=5Hz, C₆—H), 5.63 (2H, bs, S=CH₂—), 5.92 (1H, dd, J=5Hz, J=8Hz, C₇—H), 6.84 (1H, s, thiazole-H), 6.91 (1H, q, J=7Hz, >CH—CH₃), 9.75 (1H, d, J=8Hz, —NHCO—) |

Note:
*Hydrochloride

TABLE 28

[Structure: H₂N-(thiazole)-C(=N-OCH₃)-CONH-(β-lactam-S)-CH₂-(isoxazoline ring with Cl) with COOR¹ (syn isomer)]

| R¹ | Melting point (°C.) | IR(KBr) cm⁻¹: $\nu_{C=O}$ | NMR(d₆-DMSO) ppm value: |
|---|---|---|---|
| —CH₂O(CH₂)₃CH₃ | 125–130 | 1780, 1722, 1670 | 0.87 (3H, t, J=7Hz, —(CH₂)₃CH₃), 1.15–1.58 (4H, m, —CH₂CH₂CH₂CH₃), 3.45 (2H, bs, C₂—H), 3.48 (2H, t, J=7Hz, —CH₂CH₂CH₂CH₃), 3.83 (3H, s, —OCH₃), 5.10 (1H, d, J=5Hz, C₆—H), 5.25 (1H, dd, J=5Hz, J=8Hz, C₇—H), 5.30 (2H, s, —COOCH₂O—), 5.41 (2H, bs, S=CH₂—), 6.71 (1H, s, thiazole-H), 7.18 (2H, bs, —NH₂), 8.01 (1H, s, N=CH), 9.57 (1H, d, J=8Hz, —CONH—) |
| *<br>—CHOCOCH₂CH₃<br>   \|   \|\|<br>  CH₃ O<br>*1 | 133–135 | 1778, 1755, 1670 | 1.23 (3H, t, J=7Hz, —CH₂CH₃), 1.52 (3H, d, J=5Hz, >CH—CH₃), 3.49 (2H, bs, C₂—H), 3.84 (3H, s, —OCH₃), 4.19 (2H, q, J=7Hz, —CH₂CH₃), 4.95–5.52 |

TABLE 28-continued

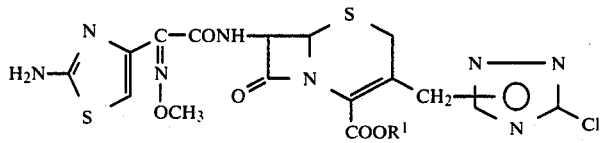

(syn isomer)

| $R^1$ | Melting point (°C.) | IR(KBr) cm$^{-1}$: $\nu_{C=O}$ | NMR(d$_6$-DMSO) ppm value: |
|---|---|---|---|

(3H, m, C$_6$—H, [structure]), 5.81 (1H, dd, J=5Hz,

J=8Hz, C$_7$—H), 6.71 (1H, s, [structure]), 6.76 (1H, q

J=5Hz, CH—CH$_3$), 7.16 (1H, bs, —NH$_2$), 8.04 (1H, s, [structure]—H), 9.60 (1H, d, J=8Hz, —CONH—)

Note:
*Optical isomer
*1 The upper component obtained in Table 24 was used as the starting compound.

EXAMPLE 37

Reaction and treatment were carried out in the same manner as in Example 33-(1) to obtain the compound shown in Table 29.

TABLE 29

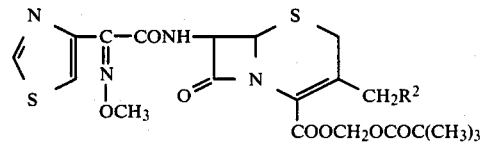

(syn isomer)

| —R$^2$ | Melting point (°C.) | IR(KBr) cm$^{-1}$: $\nu_{C=O}$ | NMR(CDCl$_3$) ppm value: |
|---|---|---|---|
| [oxadiazole-Cl structure] | 65–81 (decomp.) | 1785, 1750, 1675 | 1.20 (9H, s, —C(CH$_3$)$_3$), 3.25 (2H, bs, C$_2$—H), 3.98 (3H, s, —OCH$_3$), 5.00, 5.45 (2H, ABq, J=15Hz, [structure]), 5.03 (1H, d, J=5Hz, C$_6$—H), 5.84 (2H, s, —OCH$_2$O—), 5.91 (1H, dd, J=5Hz, J=8Hz, C$_7$—H), 7.68 (1H, d, J=2Hz, [structure]), 7.75 (1H, s, [structure]—H), 7.93 (1H, d, J=8Hz, —CONH—), 8.77 (1H, d, J=2Hz, H—[structure]) |
| [triazole-CH$_3$ structure] | 71–81 (decomp.) | 1785, 1745, 1675 | 1.20 (9H, s, —C(CH$_3$)$_3$), 2.47 (3H, s, [structure]—CH$_3$), 3.30 (2H, bs, C$_2$—H), 3.98 (3H, s, —OCH$_3$), 5.04 (1H, d, J=5Hz, C$_6$—H), 5.39, 5.76 (2H, ABq, J=15Hz, [structure]), 5.85 (2H, s, —OCH$_2$O—), 5.94 (1H, dd, J=5Hz, J=8Hz, C$_7$—H), 7.69 (1H, d, |

TABLE 29-continued

[Structure: cephem with 2-aminothiazol-4-yl methoxyimino group (syn isomer), pivaloyloxymethyl ester, —CH$_2$R$^2$ at C-3]

(syn isomer)

| —R$^2$ | Melting point (°C.) | IR(KBr) cm$^{-1}$: $\nu_{C=O}$ | NMR(CDCl$_3$) ppm value: |
|---|---|---|---|

J=2Hz, [thiazole-H], 7.91 (1H, d, J=8Hz, —CONH—), 8.77 (1H, d, J=2Hz, H—[thiazole])

EXAMPLE 38

A solution of 2.5 g of mesitylenesulfonic acid dihydrate in 20 ml of ethyl acetate was added to a solution of 5.93 g of pivaloyloxymethyl 7-[2-(2-aminothiazol-4-yl)-2-(syn)-methoxyiminoacetamido]-3-[2-(5-methyl-1,2,3,4-tetrazolyl)methyl]-Δ$^3$-cephem-4-carboxylate in 50 ml of ethyl acetate. The deposited crystals were collected by filtration, washed with ethyl acetate and dried to obtain 7.39 g (yield 93.2%) of mesitylenesulfonic acid salt of pivaloyloxymethyl 7-[2-(2-aminothiazol-4-yl)-2-(syn)-methoxyiminoacetamido]-3-[2-(5-methyl-1,2,3,4-tetrazolyl)methyl]-Δ$^3$-cephem-4-carboxylate having a melting point of 218°-220° C. (decomp.).

IR(KBr) cm$^{-1}$: $\nu_{C=O}$ 1782, 1745, 1680.

NMR(d$_6$-DMSO) ppm value:

1.15 (9H, s, —C(CH$_3$)$_3$), 2.14 (3H, s, CH$_3$—[mesityl]—), 2.43 (3H, s, [tetrazolyl]—CH$_3$), 2.53 (6H, s, —[mesityl with 2 CH$_3$]—), 3.52 (2H, bs, C$_2$—H), 3.93 (3H, s, —OCH$_3$),
5.20 (1H, d, J=5Hz, C$_6$—H), 5.56 (2H, bs,

[S—C(=)—CH$_2$—]), 5.78 (1H, dd, J=5Hz, J=8Hz, C$_7$—H), 5.85 (2H, s, —COOCH$_2$O—), 6.50 (3H, bs, H$_3$N$\oplus$—), 6.75 (2H, s, [mesityl-H]—SO$_3$—), 6.93 (1H, s, [thiazole-H]), 9.81 (1H, d, J=8Hz, —CONH—).

EXAMPLE 39

Using pivaloyloxymethyl 7-amino-3-[2-(5-methyl-1,2,3,4-tetrazolyl)methyl]-Δ$^3$-cephem-4-carboxylate, reaction and treatment were carried out in the same manner as in Example 12-(1) and Example 28-(1) and (2) to obtain pivaloyloxymethyl 7-[2-(2-aminothiazol-4-yl)-2-(syn)-hydroxyiminoacetamido]-3-[2-(5-methyl-1,2,3,4-tetrazolyl)methyl]-Δ$^3$-cephem-4-carboxylate.

Further, this compound was treated in ethyl acetate with a solution of dry hydrogen chloride in diethyl ether to obtain hydrochloride of pivaloyloxymethyl 7-[2-(2-aminothiazol-4-yl)-2-(syn)-hydroxyiminoacetamido]-3-[2-(5-methyl-1,2,3,4-tetrazolyl)methyl]-Δ$^3$-cephem-4-carboxylate having a melting point of 142°-145° C. (decomp.)

IR(KBr) cm$^{-1}$: $\nu_{C=O}$ 1785, 1750, 1675.

NMR(d$_6$-DMSO) ppm value: 1.20 (9H, s, —C(CH$_3$)$_3$), 2.49

(3H, s, [tetrazolyl]—CH$_3$), 3.55 (2H, bs, C$_2$—H), 5.26 (1H, d, J=5 Hz, C$_6$—H), 5.63

(2H, bs, [S—C(=)—CH$_2$—]), 5.78-5.95 (3H, m, C$_7$—H, —COOCH$_2$O—), 6.84

(1H, s, [thiazole-H]), 9.76 (1H, d, J=7 Hz, —CONH—).

PREPARATION EXAMPLE 1

According to the formulation shown below, the main ingredient was previously mixed and triturated with lactose. To the mixture was added an aqueous solution of hydroxypropyl cellulose. The resulting mixture was kneaded, dried and pulverized to obtain powder. The powder was blended with magnesium stearate previously triturated with starch, and then the resulting mixture was tabletted.

| Formulation | |
|---|---|
| Hydrochloride of pivaloyloxymethyl | 130 mg |

-continued

| Formulation | |
|---|---|
| 7-[2-(2-aminothiazol-4-yl)-2-(syn)-methoxyiminoacetamido]-3-[2-(5-methyl-1,2,3,4-tetrazolyl)methyl]-$\Delta^3$-cephem-4-carboxylate | |
| Lactose | 20 mg |
| Starch | 44 mg |
| Hydroxypropyl cellulose | 5.4 mg |
| Magnesium stearate | 0.6 mg |
| | 200 mg/tablet |

By using other compounds in place of the aboved compound, tablets can be obtained similarly.

PREPARATION EXAMPLE 2

According to the formulation mentioned below, a portion of starch and magnesium stearate were mixed and triturated, and the trituration thus obtained was mixed with the residual part of starch, hydroxypropyl cellulose and the main ingredient. The mixture thus obtained was formed into capsules according to a conventional capsule packing process:

| Formulation | |
|---|---|
| Hydrochloride of pivaloyloxymethyl 7-[2-(2-aminothiazol-4-yl)-2-(syn)-methoxyiminoacetamido]-3-[2-(5-methyl-1,2,3,4-tetrazolyl)methyl]-$\Delta^3$-cephem-4-carboxylate | 136 mg |
| Starch | 54 mg |
| Hydroxypropyl cellulose | 6 mg |
| Magnesium stearate | 4 mg |
| | 200 mg/capsule |

By using other compounds in place of the above-mentioned compound, capsule preparations can be obtained similarly.

PREPARATION EXAMPLE 3

According to the formulation shown below, the main ingredient was previously mixed and triturated with lactose. To the mixture was added an aqueous solution of hydroxypropyl cellulose. The resulting mixture was kneaded, dried and pulverized to obtain powder. The powder was blended with magnesium stearate previously triturated with starch, and then the resulting mixture was tabletted.

| Formulation | |
|---|---|
| Mesitylenesulfonic acid salt of pivaloyloxymethyl 7-[2-(2-aminothiazol-4-yl)-2-(syn)-methoxyiminoacetamido]-3-[2-(5-methyl-1,2,3,4-tetrazolyl)methyl]-$\Delta^3$-cephem-4-carboxylate | 130 mg |
| Lactose | 20 mg |
| Starch | 44 mg |
| Hydroxypropyl cellulose | 5.4 mg |
| Magnesium stearate | 0.6 mg |
| | 200 mg/tablet |

By using other compounds in place of the above-mentioned compound, tablets can be obtained similarly.

PREPARATION EXAMPLE 4

According to the formulation mentioned below, a portion of starch and magnesium stearate were mixed and triturated, and the trituration thus obtained was mixed with the residual part of starch, hydroxypropyl cellulose and the main ingredient. The mixture thus obtained was formed into capsules according to a conventional capsule packing process:

| Formulation | |
|---|---|
| Mesitylenesulfonic acid salt of pivaloyloxymethyl 7-[2-(2-aminothiazol-4-yl)-2-(syn)-methoxyiminoacetamido]-3-[2-(5-methyl-1,2,3,4-tetrazolyl)methyl]-$\Delta^3$-cephem-4-carboxylate | 136 mg |
| Starch | 54 mg |
| Hydroxypropyl cellulose | 6 mg |
| Magnesium stearate | 4 mg |
| | 200 mg/capsule |

By using other compounds in place of the above-mentioned compound, capsule preparations can be obtained similarly.

PREPARATION EXAMPLE 5

A mixture of sodium hydrogen carbonate with 7-[2-(2-aminothiazol-4-yl)-2-(syn)-methoxyiminoacetamido]-3-[2-(5-methyl-1,2,3,4-tetrazolyl)methyl]-$\Delta^3$-cephem-4-carboxylic acid was treated in a conventional manner to obtain a freeze-dried and sterilized sodium salt. One gram (potency) of the sodium salt was dissolved in 20 ml of physiological saline solution to obtain an injection.

PREPARATION EXAMPLE 6

One gram (potency) of the freeze-dried product obtained in Preparation Example 5 was dissolved in 4 ml of 0.5% (W/V) aqueous lidocaine hydrochloride solution to obtain a dilutable injection.

PREPARATION EXAMPLE 7

One gram (potency) of the freeze-dried product obtained in Preparation Example 5 was dissolved into 20 ml of 5% glucose solution to obtain an injection.

Moreover, the other compounds (free carboxylic acids) of this invention represented by the formula [I] can also be formed into the corresponding freeze-dried products (sodium salts) or injections by processing them in the same manner as in Preparation Examples 5–7.

What is claimed is:

1. 7-(Substituted or unsubstituted amino)-3-substituted methyl-$\Delta^3$-cephem-4-carboxylic acid represented by the following formula or a salt thereof:

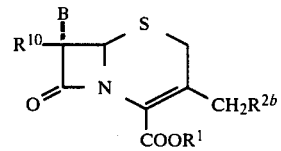

wherein $R^1$ represents a hydrogen atom or a carboxyl-protecting group; $R^{2b}$ represents a 2-(1,2,3,4-tetrazolyl) group, attached to the exomethylene group at the 3-position of the cephem ring through a carbon-nitrogen bond, which may be substituted by one substitutent selected from the group consisting of halogen, $C_{1-14}$alkyl, benzyl, phenethyl, 4-methylbenzyl, naphthylmethyl, phenyl, naphthyl, indanyl, $C_{2-10}$alkenyl, hydroxyl, protected hydroxyl, oxo, $C_{1-14}$alkylthio, nitro, cyano, amino, protected amino, $C_{1-14}$alkylamino, di-$C_{1-}$ 14alkylamino, $C_{1-12}$acyl, $C_{1-12}$acyl-$C_{1-14}$alkyl, carboxyl, protected carboxyl, carbamoyl, amino-$C_{1-14}$alkyl, N-$C_{1-14}$ alkylamino-$C_{1-14}$alkyl, N,N-di-$C_{1-14}$alkylamino-$C_{1-14}$alkyl, hydroxy-$C_{1-14}$alkyl, hydroxyimino-$C_{1-14}$alkyl, $C_{1-14}$alkoxy-$C_{1-14}$alkyl, carboxy-$C_{1-14}$alkyl, $C_{1-14}$alkoxy-$C_{1-14}$alkyl, benzyloxycarbonyl-$C_{1-14}$alkyl, phenethyloxycarbonyl-$C_{1-14}$alkyl, 4-methylbenzyloxycarbonyl-$C_{1-14}$alkyl, naphthylmethyloxycarbonyl-$C_{1-14}$alkyl, sulfo-$C_{1-14}$alkyl, sulfo, sulfamoyl-$C_{1-14}$alkyl, sulfamoyl, carbamoyl-$C_{1-14}$alkyl, carbamoyl-$C_{2-10}$alkenyl and N-hydroxycarbamoyl-$C_{1-14}$alkyl; $R^{10}$ represents an amino group or a protected amino group represented by the formula,

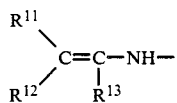

or by the formula,

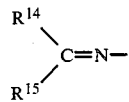

in which $R^{11}$, $R^{12}$, $R^{13}$, $R^{14}$ and $R^{15}$, which may be identical or different, are hydrogen atoms or $C_{1-14}$alkyl, $C_{2-10}$alkenyl, $C_{3-7}$cycloalkyl, $C_{5-7}$cycloalkenyl, phenyl, naphthyl, indanyl, benzyl, phenethyl, 4-methylbenzyl, naphthylmethyl, furyl, thienyl, pyrrolyl, pyrazolyl, imidazolyl, thiazolyl, isothiazolyl, oxazolyl, isoxazolyl, thiadiazolyl, oxadiazolyl, thiatriazolyl, oxatriazolyl, triazolyl, tetrazolyl, pyridyl, 3-(2-methyl-4-pyrrolinyl), 3-(4-pyrrolinyl), N-(methylpiperidinyl), quinolyl, phenazinyl, 1,3-benzodioxolanyl, benzofuryl, benzothienyl, benzoxazolyl, benzthiazolyl, coumarinyl or acyl groups, which acyl can be derived from formic acid, acetic acid, propionic acid, butanoic acid, isobutanonic acid, pentanoic acid, methoxyacetic acid, methylthioacetic acid, acrylic acid, crotonic acid, cyclohexanoic acid, cyclopentaneacetic acid, cyclohexaneacetic acid, cyclohexanepropionic acid or cyclohexadieneacetic acid; and B represents a hydrogen atom or a $C_{1-5}$alkoxy group.

2. 7-(Substituted or unsubstituted amino)-3-substituted methyl-$\Delta^3$-cephem-4-carboxylic acid or a salt thereof according to claim 1, wherein B is a hydrogen atom.

3. 7-(Substituted or unsubstituted amino)-3-substituted methyl-$\Delta^3$-cephem-4-carboxylic acid or a salt thereof according to claim 2, wherein $R^{2b}$ is a 2-(1,2,3,4-tetrazolyl) group which may optionally be substituted by one substituent selected from the group consisting of halogen, $C_{1-14}$alkyl, hydroxyl, protected hydroxyl, benzyl, phenethyl, 4-methylbenzyl, naphthylmethyl, $C_{1-14}$alkythio, cyano, amino, protected amino, carboxyl, protected carboxyl, $C_{1-14}$alkoxy-$C_{1-14}$alkyl, amino-$C_{1-14}$alkyl, N-$C_{1-14}$alkylamino-$C_{1-14}$alkyl, $C_{1-12}$acyl, phenyl, naphthyl, indanyl and $C_{1-14}$alkoxycarbonyl-$C_{1-14}$alkyl.

4. 7-(Substituted or unsubstituted amino)-3-substituted methyl-$\Delta^3$-cephem-4-carboxylic acid or a salt thereof according to claim 3, wherein $R^{10}$ is an amino group.

5. 7-(Substituted or unsubstituted amino)-3-substituted methyl-$\Delta^3$-cephem-4-carboxylic acid or a salt thereof according to claim 4, wherein $R^{2b}$ is 2-(5-methyl-1,2,3,4-tetrazolyl), 2-(5-acetamido-1,2,3,4-tetrazolyl), 2-(5-ethoxycarbonylmethyl-1,2,3,4-tetrazolyl), 2-(5-phenyl-1,2,3,4-tetrazolyl), 2-(1,2,3,4-tetrazolyl), 2-(5-bromo-1,2,3,4-tetrazolyl), 2-(5-methylthio-1,2,3,4-tetrazolyl), 2-(5-amino-1,2,3,4-tetrazolyl), 2-(5-ethyl-1,2,3,4-tetrazolyl) or 2-(5-ethoxycarbonyl-1,2,3,4-tetrazolyl).

* * * * *

UNITED STATES PATENT AND TRADEMARK OFFICE
CERTIFICATE OF CORRECTION

PATENT NO. : 4,673,738

DATED : June 16, 1987

INVENTOR(S) : Hiroshi Sadaki, et al.

It is certified that error appears in the above-identified patent and that said Letters Patent is hereby corrected as shown below:

On the Title Page, Item [73],
the assignee should be corrected to read -- Toyama Chemical Co., Ltd. --.

Signed and Sealed this

Fifth Day of September, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,673,738

DATED : June 16, 1987

INVENTOR(S) : Hiroshi SADAKI, et al.

It is certified that error appears in the above-identified patent and that said Letters Patent is hereby corrected as shown below:

Column 1, line 21, change "therepeutic" to --therapeutic--;
         line 24, change "teterocyclic" to --heterocyclic--;
         line 45, after "cephalosporins", insert --being--.

Column 2, line 10, after "may", insert --optionally--;
         line 21, change "bolt" to --bond--;
         line 41, change "akenyl" to --alkenyl--.

Column 3, line 46, change "lower-akyl-substituted" to
         --lower-alkyl-substituted--;
         line 54, change "substitutents" to --substituents--.

Column 4, line 17, change "Alicylic" to --Alicyclic--;
         line 48, change "unsunstituted" to --unsubstituted--;
         lines 55-56, change "1,3,-dioxol" to --1,3-dioxol--.

Column 5, lines 1-3, change "propoxycarbonylmethyl, isopropoxy-carbonylmethyl, n-butyloxycarbonylmethyl, tert.-butyloxycarbonylmethyl" to --propoxycarbonylmethyl, isopropoxycarbonyloxymethyl, n-butyloxycarbonyloxymethyl, tert.-butyloxycarbonyloxymethyl, 1--;
         lines 9-10, change "phihalididenealkyl groups" to --phthalidylidene-alkyl groups--;
         line 36, after "may", insert --optionally--;
         line 52, change "specfically" to --specifically--;
         line 55, change "methoxybenzylocycarbonyl" to --methoxybenzyloxycarbonyl--;

UNITED STATES PATENT AND TRADEMARK OFFICE
CERTIFICATE OF CORRECTION

PATENT NO. : 4,673,738
DATED : June 16, 1987
INVENTOR(S) : Hiroshi SADAKI, et al.

It is certified that error appears in the above-identified patent and that said Letters Patent is hereby corrected as shown below:

Column 6, lines 22-23, change "2-ethoxycarbonylcylcohexylidene" to --2-ethoxycarbonylcyclohexylidene--;
  line 48, after "may", insert --optionally--;
  line 57, change "substitutents" to --substituents--;
  line 67, change "hdyroxyl" to --hydroxyl--.

Column 7, line 30, after "may", insert --optionally--;
  line 30, change "substitued" to --substituted--;
  line 42, after "may", insert --optionally--;
  line 51, after "may", insert --optionally--.

Column 12, item (3), change "introvenously" to --intravenously--.

Column 13, line 30, change "orallyl" to --orally--.

Column 15, Formula (II), change "Y" to --Z--;

Formula (II), under Formula (II), insert --or salt thereof--.

Column 16, Formula (IVa), change "R$^{16}$H$_2$COCCONH" to --R$^{16}$CH$_2$COCCONH--.

Delete Formula (Ie) in its entirety and replace with new formula

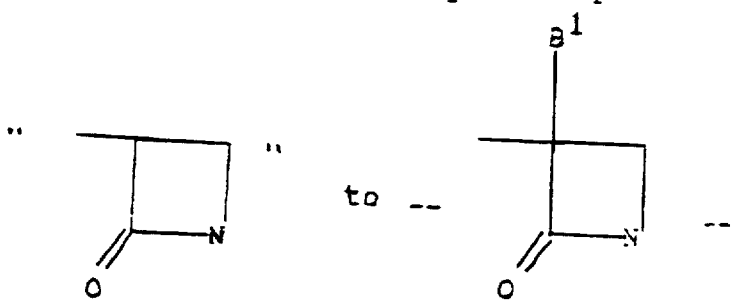

UNITED STATES PATENT AND TRADEMARK OFFICE
CERTIFICATE OF CORRECTION

PATENT NO. : 4,673,738

DATED : June 16, 1987

INVENTOR(S) : Hiroshi SADAKI, et al.

It is certified that error appears in the above-identified patent and that said Letters Patent is hereby corrected as shown below:

Column 17, line 41, change "Y" to --Z--.

Column 20, line 47, change "7-substituted or unsubstituted amino" to --7-(substituted or unsubstituted) amino--;
lines 55-56, change "heretocyclic" to --heterocyclic--.

Column 21, line 39, change "substitutens" to --substitutents--;
line 67, change "at" to --as--.

Column 22, line 48, change "ketote" to --ketone--.

Column 24, lines 41-42, change "N,N'-dicylcohexyl" to --N,N'-dicyclohexyl--;
line 53, change "trihloride" to --trichloride--;
line 59, change "agnet" to --agent--.

Column 25, line 9, change "hydrogen carbonates" to --hydrogencarbonates--;
line 24, change "[XIII]" to --[IV]--.

Column 26, line 2, change "[VII]" to --[X]--.

Column 27, lines 44-45, change "hydrogen carbonate" to --hydrogencarbonate--;
line 46, change "hydorgen carbonate" to --hydrogencarbonate--.

UNITED STATES PATENT AND TRADEMARK OFFICE
CERTIFICATE OF CORRECTION

PATENT NO. : 4,673,738

DATED : June 16, 1987

INVENTOR(S) : Hiroshi SADAKI, et al.

It is certified that error appears in the above-identified patent and that said Letters Patent is hereby corrected as shown below:

Column 28, line 62, after "such" delete "a".

Column 30, line 22, change "hydrogen carbonate" to --hydrogencarbonate--;
  line 33, change "(2H, Abq, J=14 cps," to --(2H, ABq, J=14 Hz--;
  line 39, change "-COOH<)," to -- -CH<),--;
  Table 4, in the formula, change "$CH_2NHCOR^{10}$" to --$CH_2NHCOR^9$--.

Column 33, line 43, move the title "TABLE 5" underneath the formulas and centered.

Column 34, lines 38-54, delete "TABLE 5-continuted" in its entirety.

Column 35, line 21, change "solcent" to --solvent--;
  line 26, change "hydrogen carbonate" to --hydrogencarbonate--.

Column 36, line 56, change "solutoin" to --solution--;
  line 57, change "rrom" to --room--.

Column 41, Table 7, fourth column, change "7.23 (15Hz, s," to --7.23 (15H, s,--.

UNITED STATES PATENT AND TRADEMARK OFFICE
CERTIFICATE OF CORRECTION

PATENT NO.  : 4,673,738

DATED       : June 16, 1987

INVENTOR(S) : Hiroshi SADAKI, et al.

It is certified that error appears in the above-identified patent and that said Letters Patent is hereby corrected as shown below:

Column 52, Table 8, column 5, at bottom of page, change "-CH$_2$ x 2)" to -- -CH$_3$ x 2)--.

Column 59, line 49, change "hydrogen carbonate" to --hydrogencarbonate--.

Column 60, line 49, change "hydrogen carbonate" to --hydrogencarbonate--.

Column 61, line 18, change "C$_2$-H)" to -- -C$_2$-H)--;
line 45, change "5-methyl-1,2,3-tetrazolyl)" to --5-methyl-1,2,3,4-tetrazolyl--.

Column 62, line 50, change "homogenerous" to --homogeneous--;
line 60, change "hydrogen carbonate" to --hydrogencarbonate--.

Column 64, line 22, change "dimethylformamide" to --N,N-dimethylformamide--;
line 29, change "hydrogen carbonate" to --hydrogencarbonate--.

Column 71, Table 13, second column, change "1144-146" to --144-146--.

UNITED STATES PATENT AND TRADEMARK OFFICE
CERTIFICATE OF CORRECTION

PATENT NO. : 4,673,738

DATED : June 16, 1987

INVENTOR(S) : Hiroshi SADAKI, et al.

It is certified that error appears in the above-identified patent and that said Letters Patent is hereby corrected as shown below:

Column 73, Table 13, column one at bottom of page, delete formula in its entirety and replace with new formula

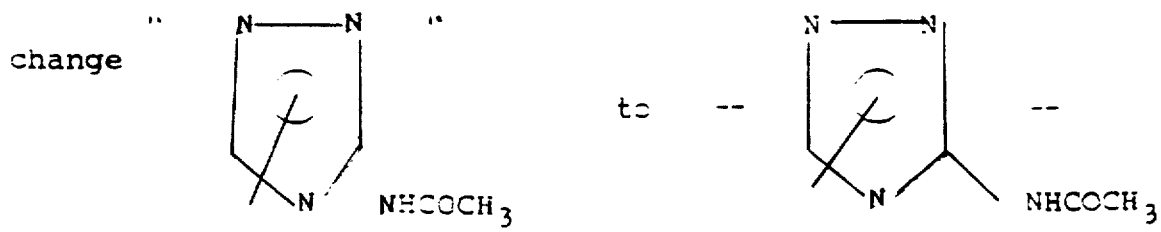

Column 81, line 44, change "(3)", to --(2)--;
    line 55, change "hydrogen carbonate" to --hydrogencarbonate--.

Column 82, line 40, change "hydrogen carbonate" to --hydrogencarbonate--;
    lines 53-54, change "hydrogen carbonate" to --hydrogencarbonate--.

Column 84, last formula on page, change "OCH$_2$O," to -- -OCH$_2$O,--.

Column 87, line 55, change "hydrogen carbonate" to --hydrogencarbonate--.

UNITED STATES PATENT AND TRADEMARK OFFICE
CERTIFICATE OF CORRECTION

PATENT NO. : 4,673,738

DATED : June 16, 1987

INVENTOR(S) : Hiroshi SADAKI, et al.

It is certified that error appears in the above-identified patent and that said Letters Patent is hereby corrected as shown below:

Column 89, line 37, change "pivaloyoxymethyl" to
--pivaloyloxymethyl--;
line 68, change "hydrogen carbonate" to
--hydrogencarbonate--.

Column 92, line 29, change "hydrogen carbonate" to
--hydrogencarbonate--.

Column 94, line 2, change "hydrogen carbonate" to
--hydrogencarbonate--.

Column 96, line 14, change "hydrogen carbonate" to
--hydrogencarbonate--.

Column 97, Table 16, at the begtinning of top formula, change
"$R^5$" to --$R^4$--.

Column 108, line 28, change "hydrogen carbonate" to
--hydrogencarbonate--.

Column 109, line 15, change "-3-(3-chloro-1,2,4-triazolyl)
methyl)-" to -- 3-[(3-chloro-1,2,4-triazolyl)
methyl];
lines 39-40, change "hydrogen carbonate" to
--hydrogencarbonate--.

Column 110, line 55, change "hydrogen carbonate" to
--hydrogencarbonate--.

Column 112, line 60, change "(3)" to --(2)--.

UNITED STATES PATENT AND TRADEMARK OFFICE
CERTIFICATE OF CORRECTION

PATENT NO. : 4,673,738

DATED : June 16, 1987

INVENTOR(S) : Hiroshi SADAKI, et al.

It is certified that error appears in the above-identified patent and that said Letters Patent is hereby corrected as shown below:

Column 114, line 25, change "alumimum" to --aluminum--.

Column 120, line 30, change "hydrogen carbonate" to --hydrogencarbonate--.

Column 122, lines 41-42, change "hydrogen carbonate" to --hydrogencarbonate--.

Column 127, line 1, insert the heading --Example 31--.

Column 128, line 24, change "hydrogen carbonate" to --hydrogencarbonate--;
line 41, change "pint" to --point--;
line 60, delete "(1)".

Column 131, line 45, change "1,2,4-triazolyl)]methyl" to --1,2,4-triazolyl)methyl]--;
line 53, change "hydrogen carbonate" to --hydrogencarbonate--.

Column 133, line 6, change "hydrogen carbonate" to --hydrogencarbonate--.

Column 134, line 1, delete "(1)";
lines 13-14, change "hydrogen carbonate" to --hydrogencarbonate--.

UNITED STATES PATENT AND TRADEMARK OFFICE
CERTIFICATE OF CORRECTION

PATENT NO. : 4,673,738
DATED : June 16, 1987
INVENTOR(S) : Hiroshi SADAKI, et al.

It is certified that error appears in the above-indentified patent and that said Letters Patent is hereby corrected as shown below:

Column 144, line 3, change "hydrogen carbonate" to
--hydrogencarbonate--;
line 12, change "1,2,3,4-tetrazolyl)methyl" to
--1,2,3,4-tetrazolyl)methyl]--.

Column 158, line 23, change "hydrogen carbonate" to
--hydrogencarbonate--.

Signed and Sealed this

Sixth Day of December, 1994

Attest:

BRUCE LEHMAN

Attesting Officer  *Commissioner of Patents and Trademarks*